US012009078B2

(12) United States Patent (10) Patent No.: US 12,009,078 B2
Pulitzer et al. (45) Date of Patent: Jun. 11, 2024

(54) SYSTEM AND METHOD FOR MEDICAL ESCALATION AND INTERVENTION THAT IS A DIRECT RESULT OF A REMOTE DIAGNOSTIC TEST

(71) Applicant: RELIANT IMMUNE DIAGNOSTICS, INC, Austin, TX (US)

(72) Inventors: Jovan Hutton Pulitzer, Frisco, TX (US); Henry Joseph Legere, III, Austin, TX (US)

(73) Assignee: Reliant Immune Diagnostics, Inc., Austin, TX (US)

( * ) Notice: Subject to any disclaimer, the term of this patent is extended or adjusted under 35 U.S.C. 154(b) by 332 days.

(21) Appl. No.: 16/137,150

(22) Filed: Sep. 20, 2018

(65) Prior Publication Data

US 2019/0096516 A1 Mar. 28, 2019

Related U.S. Application Data

(63) Continuation-in-part of application No. 15/804,990, filed on Nov. 6, 2017, now Pat. No. 11,693,002, (Continued)

(51) Int. Cl.
*G16H 80/00* (2018.01)
*G01N 33/543* (2006.01)
(Continued)

(52) U.S. Cl.
CPC ....... *G16H 20/10* (2018.01); *G01N 33/54388* (2021.08); *G01N 33/54389* (2021.08);
(Continued)

(58) Field of Classification Search
None
See application file for complete search history.

(56) References Cited

U.S. PATENT DOCUMENTS 4,861,711 A 8/1989 Friesen et al.
5,081,013 A 1/1992 Rovelli et al.
(Continued)

FOREIGN PATENT DOCUMENTS

CN 105954512 A 9/2016
EP 2404673 A1 1/2012
(Continued)

OTHER PUBLICATIONS

Jianjun Li et al. Application of Microfluidic Devices to Proteomics Research. Journal: Molecular & Cellular Proteomics Jan. 3, 2002. 1:157-168. Canada.
(Continued)

*Primary Examiner* — Rebecca M Giere

(57) ABSTRACT

A method for initiating a telemedicine conference on a mobile device is provided. The method comprises receiving diagnostic test results in response to a diagnostic test, determining if the diagnostic test results include a positive result, storing the diagnostic test results on a server disposed on a network, presenting, if the diagnostic test results are positive, a telemedicine initiation option on a screen of the mobile device, determining whether the telemedicine initiation option is selected, sending the diagnostic test results from the server to the telemedicine provider, sending additional medical history information to the telemedicine provider, and initiating a telemedicine conference with the telemedicine provider. Some of these aspects also provide healthcare providers the ability to electronically send prescriptions and provide users the ability to use a mobile application to send prescriptions to pharmacies to be filled.

9 Claims, 34 Drawing Sheets

Related U.S. Application Data which is a continuation-in-part of application No. 15/295,398, filed on Oct. 17, 2016, now Pat. No. 9,857,373.

(60) Provisional application No. 62/566,593, filed on Oct. 2, 2017, provisional application No. 62/419,382, filed on Nov. 8, 2016.

(51) Int. Cl.
    *G16H 10/40*      (2018.01)
    *G16H 20/10*      (2018.01)
    *G16H 30/40*      (2018.01)

(52) U.S. Cl.
    CPC ....... *G01N 33/54391* (2021.08); *G16H 10/40* (2018.01); *G16H 30/40* (2018.01); *G16H 80/00* (2018.01); *G01N 2333/08* (2013.01); *G01N 2333/59* (2013.01)

(56) References Cited

U.S. PATENT DOCUMENTS

| | | | |
|---|---|---|---|
| 5,468,648 | A | 11/1995 | Chandler |
| 5,567,594 | A | 10/1996 | Calenoff |
| 5,587,061 | A | 12/1996 | Chen |
| 5,709,788 | A | 1/1998 | Chen |
| 5,904,826 | A | 5/1999 | Chen |
| 6,149,865 | A | 11/2000 | Hsu |
| 7,090,802 | B1 | 8/2006 | Wang |
| 7,235,098 | B2 | 6/2007 | Palmaz |
| 7,989,217 | B2 | 8/2011 | Yee et al. |
| 8,308,452 | B2 | 11/2012 | Amirouche et al. |
| 8,506,901 | B2 | 8/2013 | Chen et al. |
| 8,508,757 | B1 | 8/2013 | Koehl |
| 8,655,009 | B2 | 2/2014 | Chen et al. |
| 8,807,169 | B2 | 8/2014 | Amirouche et al. |
| 8,877,140 | B2 | 11/2014 | Chen et al. |
| 8,911,679 | B2 | 12/2014 | Chen et al. |
| 9,285,323 | B2 | 3/2016 | Burg et al. |
| 9,390,237 | B2 | 6/2016 | Myers et al. |
| 9,523,358 | B2 | 12/2016 | Amirouche et al. |
| 9,569,858 | B2 | 2/2017 | Babcock et al. |
| 9,607,380 | B2 | 3/2017 | Burg et al. |
| 9,726,161 | B2 | 8/2017 | Kim et al. |
| 9,857,372 | B1 | 1/2018 | Pulitzer et al. |
| 9,857,373 | B1 | 1/2018 | Pulitzer et al. |
| 10,473,659 | B2 | 11/2019 | Pulitzer et al. |
| 2002/0134682 | A1 | 9/2002 | Chen |
| 2003/0003522 | A1 | 1/2003 | Goldman |
| 2003/0172009 | A1 | 9/2003 | Katou et al. |
| 2003/0207458 | A1 | 11/2003 | Sookbumroong |
| 2004/0018576 | A1 | 1/2004 | DeMatteo et al. |
| 2004/0023412 | A1 | 2/2004 | Carlsson et al. |
| 2005/0266582 | A1 | 12/2005 | Modlin et al. |
| 2006/0008920 | A1 | 1/2006 | Wong et al. |
| 2006/0014302 | A1 | 1/2006 | Martinez |
| 2006/0166374 | A1 | 7/2006 | Hubscher |
| 2006/0222567 | A1 | 10/2006 | Kloepfer et al. |
| 2006/0245933 | A1 | 11/2006 | Balch |
| 2007/0092407 | A1 | 4/2007 | Xiao et al. |
| 2008/0070599 | A1 | 3/2008 | Apodaca |
| 2008/0118397 | A1 | 5/2008 | Slowey |
| 2009/0106331 | A1 | 4/2009 | Fridman et al. |
| 2009/0298191 | A1 | 12/2009 | Whitesides et al. |
| 2010/0125186 | A1 | 5/2010 | Abuachi |
| 2010/0317033 | A1 | 12/2010 | Abdel |
| 2011/0076691 | A1 | 3/2011 | Rundström et al. |
| 2011/0077971 | A1 | 3/2011 | Surwit |
| 2011/0257022 | A1* | 10/2011 | Hess .................... G01N 33/728 506/7 |
| 2012/0053843 | A1 | 3/2012 | Tubb |
| 2012/0082598 | A1 | 4/2012 | Baydoun |
| 2012/0284046 | A1 | 11/2012 | Baym et al. |
| 2013/0090938 | A1 | 4/2013 | Fishman et al. |
| 2013/0161190 | A1 | 6/2013 | Ewart et al. |
| 2013/0189794 | A1 | 7/2013 | Emeric et al. |
| 2013/0203043 | A1 | 8/2013 | Ozcan et al. |
| 2013/0222634 | A1 | 8/2013 | Setlur et al. |
| 2013/0273528 | A1 | 10/2013 | Ehrenkranz |
| 2014/0051173 | A1 | 2/2014 | Barstis et al. |
| 2014/0072189 | A1* | 3/2014 | Jena .................... A61B 5/1455 382/128 |
| 2014/0089006 | A1 | 3/2014 | Abreu |
| 2014/0121487 | A1* | 5/2014 | Faybishenko ..... A61F 13/15723 600/365 |
| 2014/0170679 | A1 | 6/2014 | Aitchison |
| 2014/0335527 | A1 | 11/2014 | Goel |
| 2015/0025808 | A1 | 1/2015 | Aguiar |
| 2015/0056719 | A1 | 2/2015 | Karlovac |
| 2015/0099656 | A1* | 4/2015 | Manuguerra ....... G01N 33/6845 506/9 |
| 2015/0161330 | A1* | 6/2015 | Joao .................... G16H 80/00 705/3 |
| 2015/0186518 | A1 | 7/2015 | Kusumoto et al. |
| 2015/0308961 | A1 | 10/2015 | Burg et al. |
| 2015/0330985 | A1 | 11/2015 | St-Pierre |
| 2015/0359458 | A1* | 12/2015 | Erickson ............. A61B 5/6898 455/557 |
| 2016/0057413 | A1 | 2/2016 | Zhou et al. |
| 2016/0077091 | A1 | 3/2016 | Tyrrell et al. |
| 2016/0080548 | A1 | 3/2016 | Erickson et al. |
| 2016/0117463 | A1 | 4/2016 | Nemiroski et al. |
| 2016/0144358 | A1 | 5/2016 | Patel |
| 2016/0187263 | A1 | 6/2016 | Brown |
| 2016/0223536 | A1 | 8/2016 | Johnson et al. |
| 2016/0225165 | A1 | 8/2016 | Russell et al. |
| 2016/0260215 | A1 | 9/2016 | Burg et al. |
| 2016/0274104 | A1 | 9/2016 | Aminoff et al. |
| 2016/0349185 | A1 | 12/2016 | Park et al. |
| 2017/0002432 | A1 | 1/2017 | Apte et al. |
| 2017/0011192 | A1 | 1/2017 | Arshad et al. |
| 2017/0032092 | A1 | 2/2017 | Mink et al. |
| 2017/0059566 | A1 | 3/2017 | Reed et al. |
| 2017/0061074 | A1 | 3/2017 | Singh et al. |
| 2017/0089893 | A1 | 3/2017 | Legere, III |
| 2017/0091388 | A1 | 3/2017 | Zolla et al. |
| 2017/0212124 | A1 | 7/2017 | Thalhammer et al. |
| 2017/0328892 | A1 | 11/2017 | Crisanti et al. |
| 2018/0117272 | A1 | 5/2018 | Fu et al. |
| 2019/0187140 | A1 | 6/2019 | Kamei et al. |

FOREIGN PATENT DOCUMENTS

| | | |
|---|---|---|
| EP | 2844748 A1 | 3/2015 |
| FR | 3010188 A1 | 3/2015 |
| WO | 2010118124 A2 | 10/2010 |
| WO | 2013158504 A1 | 10/2013 |
| WO | 2014113770 A1 | 7/2014 |
| WO | 2014080212 A3 | 8/2014 |
| WO | 2015016960 A1 | 2/2015 |
| WO | 2015022318 A1 | 2/2015 |
| WO | 2015054546 A1 | 4/2015 |
| WO | 2015143309 A1 | 9/2015 |
| WO | 2016079219 A1 | 5/2016 |

OTHER PUBLICATIONS

Pegah N. Abadian et al. Accepted Manuscript. Book: Analytical Methods. 22pgs. Boston, MA.

Kling A. et. al. Electrochemical microfluidic platform for simultaneous multianalyte detection. Article, 2015, 916-919, Europe.

Andre Kling et al. Multianalyte Antibiotic Detection on an Electrochemical Microfluidic Platform. Article. Jul. 19, 2016, 10036-10043, Germany.

Mercier Marco. Microfluidic Continuous Flow Cell Counting and Concentration. Article. 10pgs.

Meichei Wang Kadlec et. al. A Cell Phone-Based Microphotometric System for Rapid Antimicrobial Susceptibility Testing. Journal. 2014, vol. 19 (3) 258-266. Tucson, AZ.

(56) References Cited

OTHER PUBLICATIONS

Hongying Zhu et. al. Cost-effective and compact wide-field fluorescent imaging on a cell-phone. Article. Jan. 21, 2011. 315-322, 11(2). California.
Moffitt Jeffrey R. et. al. The single-cell chemostat: an agarose-based, microfluidic device for high-throughput, single-cell studies of bacteria and bacterial communities. Article. Oct. 24, 2017. 21pgs. 12(8).
Temiz Yuksel et al. Microelectronic Engineering. Article. 2015. 156-175. Published by Elsevier B.V. Switzerland.
Vasdekis Andreas et al. Review of methods to probe single cell metabolism and bioenergetics, Journal, Jan. 20151. 115-135. Published by Elsevier.
Wang Shuqi et al. Portable microfluidic chip for detection of *Escherichia coli* produce and blood. International Journal of Nanomedicine. May 27, 2012. 2012:7 2591-2600. MA.
Hoylandm James Donaldson. Microfluidic chip and connector. Nov. 11, 2012, 16pgs. Europe.
Baltekin Ozden et al. Antibiotic susceptibility testing in less than 30 min using direct single-cell imaging. Aug. 22, 2017. 9170-9175 vol. 114-34.
Ashraf Muhammad Waseem. Micro Electromechanical Systems (MEMS) Based Microfluidic Devices for Biomedical Applications. Journal : Molecular Sciences. Jun. 7, 2011. 3648-3704.
Radenovic Aleksandra. Advanced Bioengineering Methods Laboratory Microfluidics Lab on Chip. 27pgs.
U. Hassan et al, A microfluidic biochip for complete blood cell counts at the point-of-care, Dec. 2015, 201-213, 3(4).
Kling Andre et al, Multianalyte Antibiotic Detection on an Electrochemical Microfluidic Platform, 1-3 pgs. Germany.
Au K. Anthony et al, Microvalves and Micropumps for BioMEMS, May 24, 2011, 179-220.
Sticker Drago et al, Multi-layered, membrane-integrated microfluidics based on replica molding of a thiol-ene epoxy thermoset for . . . Article, Nov. 2015, 4542-4554,.
Shaegh et al, Plug-and-play microvalve and micropump for rapid integration with microfluidic chips, Article, Apr. 22, 2015, 557-564, Massachusetts, Springer Berlin Heidelberg.
Schafer Dawn et al, Microfluidic cell counter with embedded optical fibers fabricated by femtosecond laser ablation and anodic bonding, Article, Apr. 13, 2009, 17(8), 6068-6073, Colorado.
Hassan U. et al, A microfluidic biochip for complete blood cell counts at the point-of-care, Dec. 2015, 201-213. 3(4).
Marrs et al., Zika Virus and Pregnancy: A Review of the Literature and Clinical Considerations, Jun. 2016, Am. J. Perinatal., vol. 33 , Issue 7, pp. 625-639. (Year: 2016).
Rabe et al., Interim Guidance for Interpretaiton of Zika Virus Antibody Test Results, MMWR, 65(21 ), Jun. 2016, pp. 1-6. (Year:2016).
Brown, M. C. et al. (2009). Lateral Flow Immunoassay. Tse, H. Y., Wong, R. C. (Eds.). New York, NY: Humana Press.
Baltekin, O., et al. (Aug. 22, 2017). Antibiotic susceptibility testing in less than 30 min using direct single-cell imaging. Proceedings of the National Academy of Sciences. 114(34).
Mudanyali, O. et al. Integrated Rapid-Diagnostic-Test Reader Platform on a Cellphone. Lab on a Chip, vol. 12, No. 15. Aug. 7, 2012; pp. 7, 12.
FisherSCI. Anti-Zika virus ELISA (IgM) test instruction. Sep. 2, 2016.
Acharya, D. et al. An ultrasensitive electrogenerated chemiluminescence-based immunoassay for specific detection of Zika virus. Scientific Reports 6, Article No. 32227. Aug. 2016.
International Search Report and Written Opinion of the International Searching Authority from PCT/US17/57037, dated Dec. 28, 2017.
International Search Report and Written Opinion of the International Searching Authority from PCT/US17/57039, dated Dec. 26, 2017.
International Search Report and Written Opinion of the International Searching Authority from PCT/US17/57041, dated Dec. 14, 2017.
International Search Report and Written Opinion of the International Searching Authority from PCT/US17/60252, dated Jan. 12, 2018.
International Search Report and Written Opinion of the International Searching Authority from PCT/US17/66528, dated Mar. 7, 2018.
Centers for Disease Control and Prevention ("Interim Guidelines for Pregnant Women During a Zika Virus Outbreak—United States, 2016" Morbidity and Mortality Weekly Report (MMWR), 65(2);30-33, posted online Jan. 19, 2016, retrieved from https://www.cdc.gov/mmwr/volumes/65/wr/mm6502e1 .htm on Aug. 5, 2019, 6 pages.
Lanciotti et al: "Genetic and Serologic Properties of Zika Virus Associated with an Epidemic, Yap State, Micronesia, 2007" Emerging Infectious Diseases, www.cdc.gov/eid, vol. 14, No. 8, Aug. 2008, pp. 1232-1239, DOI: 10.3201/eid1408.080287.

\* cited by examiner

| TEST RATING | HEALTH RISK | MEDICAL INTERVENTION TYPE |
|---|---|---|
| 76+ | DEADLY | EMERGENCY |
| 51-75 | DANGEROUS | URGENT |
| 26-50 | ELEVATED | NONE |
| 0-25 | NORMAL | NONE |

SYSTEM AND METHOD FOR MEDICAL ESCALATION AND INTERVENTION THAT IS A DIRECT RESULT OF A REMOTE DIAGNOSTIC TEST

CROSS-REFERENCE TO RELATED APPLICATIONS

This application is a continuation-in-part of U.S. patent application Ser. No. 15/804,990, filed on Nov. 6, 2017, which is a continuation-in-part of U.S. patent application Ser. No. 15/295,398, filed on Oct. 17, 2016, which issued as U.S. Pat. No. 9,857,373 on Jan. 2, 2018. U.S. patent application Ser. No. 15/804,990 also claims the benefit of U.S. Provisional Application No. 62/419,382, filed on Nov. 8, 2016. This application also claims the benefit of U.S. Provisional Application No. 62/566,593, filed on Oct. 2, 2017. The contents of application Ser. Nos. 15/804,990, 62/419,382, and 62/566,593, and the contents of U.S. Pat. No. 9,857,373, are incorporated by reference herein in their entireties.

TECHNICAL FIELD

The following disclosure is related to a system and method for filling prescriptions with the use of a telemedicine mobile application.

BACKGROUND

Telemedicine is the use of telecommunication and information technology to provide clinical health care from a distance. It helps eliminate distance barriers and can improve access to medical services that would often not be consistently available in distant rural communities. It is also used to save lives in critical care and emergency situations. Although there were distant precursors to telemedicine, it is essentially a product of 20th century telecommunication and information technologies. These technologies permit communications between patient and medical staff with both convenience and fidelity, as well as the transmission of medical, imaging and health informatics data from one site to another. These telemedicine technologies provide convenient ways to obtain care from a healthcare provider, and thus, it is also desirable to have a convenient way to fill any prescriptions deemed necessary by the healthcare provider.

SUMMARY

A method for initiating a telemedicine conference on a mobile device is provided. The method comprises receiving diagnostic test results in response to a diagnostic test, determining if the diagnostic test results include a positive result, storing the diagnostic test results on a server disposed on a network, presenting, if the diagnostic test results are positive, a telemedicine initiation option on a screen of the mobile device, determining whether the telemedicine initiation option is selected, sending the diagnostic test results from the server to the telemedicine provider, sending additional medical history information to the telemedicine provider, and initiating a telemedicine conference with the telemedicine provider. Some of these aspects also provide healthcare providers the ability to electronically send prescriptions and provide users the ability to use a mobile application to send prescriptions to pharmacies to be filled.

BRIEF DESCRIPTION OF THE DRAWINGS

For a more complete understanding, reference is now made to the following description taken in conjunction with the accompanying Drawings in which.

DETAILED DESCRIPTION

Figure 1:
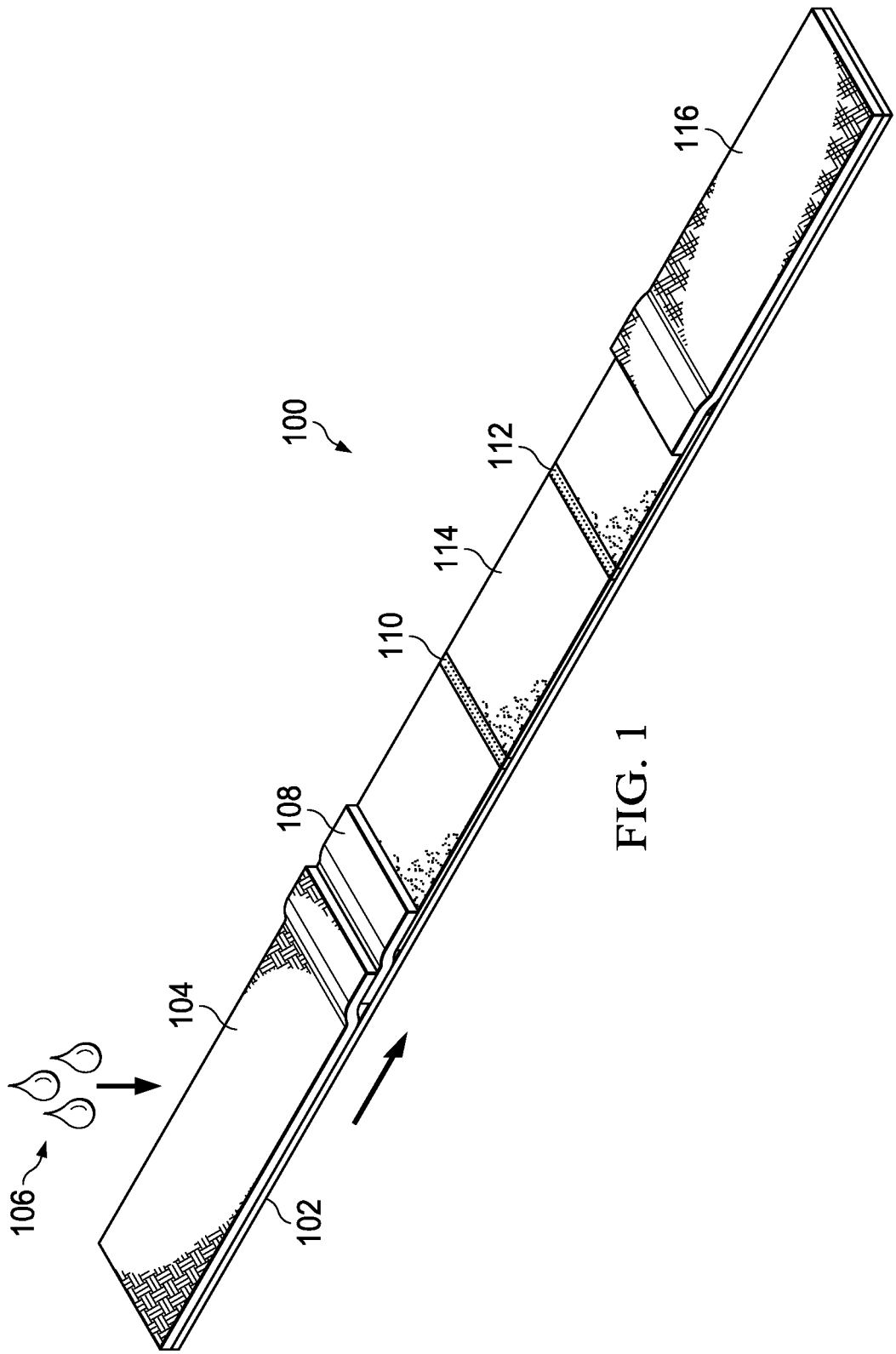
FIG. 1 illustrates a diagrammatic representation of one embodiment of a immunoassay test strip.

Referring now to the drawings, wherein like reference numbers are used herein to designate like elements throughout, the various views and embodiments of an arbovirus indicative birth defect risk test are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated one embodiment of an immunoassay test strip 100. The test strip 100 is typically housed in a testing device configured to collect a biologic analyte 106 from a user and to direct to the biologic analyte 106 onto the testing strip 100. However, it will be understood that the biologic may be applied onto a strip 100 without the strip 100 needing to be within a testing device. The test strip 100 includes a backing 102. The test strip 100 is made up of multiple sections disposed on the backing 102. A sample pad 104 is disposed on one end of the strip 100, for collecting the biologic analyte 106. The biologic analyte 106 may be any biologic needed for use in the immunoassay, such as urine, blood, saliva, stool, sweat, or other biologics to be used as an analyte. Various methods may be used to acquire the needed biologic, and such may be provided to the user packaged with the test, such as swabs, vials, containers, dilutants and other solutions, or any other equipment required. In the case of a blood analyte, a few drops of blood may be obtained from a finger stick using a finger prick device. Such a blood analyte may be blood mixed with an adequate amount of buffered solution to create the sample analyte 106 or a blood sample that is not diluted or otherwise manipulated, in which case the blood only is the analyte 106.

The biologic analyte 106, after coming into contact with the sample pad 104, begins to migrate across the strip 100 by capillary action, coming into contact with other sections of the strip 100. A particle conjugate pad 108 is disposed between the sample pad 104 and a test line 110. The conjugate pad 108 may contain various reagents associated with a particular antigen, such as a virus, allergen, or bacteria, the reagents being items such antibodies, enzymes, or other reagents needed to diagnose the particular condition. The reagent in the conjugate pad 108 may be conjugated with particles of materials such as colloid gold or colored latex beads. As the analyte 106 migrates through the conjugate pad 108, antibodies present in the sample analyte 106 complex with the reagents in the conjugate pad 108, thereby creating an immune complex that will migrate to the test zone or test line 110.

The test line 110 (T) may be precoated with the relevant antigen in question, i.e., a virus, allergen, or bacteria, for the detection of antibodies associated with the particular antigen. The immune complex created when the analyte 106 passes through the conjugate pad 108 is captured onto the antigen contained on the test line 110. This may create a qualitative response on the strip where the test line 110 is located, such as a colored response. In some embodiments, the test line 110 may not be a line, but may be other shapes or symbols, such as a plus sign. If no antigen-anti-antigen complexes are present in the analyte, no reaction occurs in the test line 110 and a qualitative response will not occur.

After passing through the test line 110, the analyte migrates further along the strip to reach a control line 112, where excess anti-antibody-colloidal gold or latex conjugates get bound. A qualitative response may be shown at the control line 112, indicating that the sample has adequately migrated across the testing membrane or substrate as intended. It will be understood that the control line 112 is not necessarily needed to perform the test, and may be eliminated entirely, but the control line 112 does provide a comparative example for a user reading the test. For example, the control line 112, in embodiments where a colored qualitative response is provided, may appear as an overly saturated color, such as a dark or bright saturated red, once the sample reaches the control line 112. This saturated color may be used as a comparison against the qualitative response shown on the test line 110. For example, if the qualitative response shown on the test line 110 is a much lighter red than that on the test line 110, it may be that very little reaction occurred at the test line. Of course, if no response is shown at all at the test line 110, no reaction has occurred. If the qualitative response at the test line 110 is of a similar saturation to the control line 112, a strong reaction is indicated.

The strip 100 may not be a continuous substrate. Rather, the various sections of the strip 100 may be separate from each other, but all adhered to the backing 102. As shown in FIG. 1, the sample pad 104 and the conjugate pad 108 are separate structures from each other. The test line 110 or zone and the control line 112 or zone are both disposed as part of a nitrocellulose membrane strip 114. The nitrocellulose membrane strip 114 is also adhered to the backing 102, but separate from the sample pad 104 and the conjugate pad 108. As shown in FIG. 1, the end of the sample pad 104 adjacent to the conjugate pad 108 may overlap the conjugate pad 108, with that end of the sample pad 104 lying over the adjacent end of the conjugate pad 108. Similarly, the end of the conjugate pad adjacent to the nitrocellulose membrane strip 114 may lie over the end of the nitrocellulose membrane adjacent to the conjugate pad. This allows for the analyte 106 to be more easily deposited onto each section of the strip 100 as it migrates across the strip 100. After the analyte 106 migrates across the nitrocellulose membrane strip 114, and thus across the test line 110 and the control line 112, the analyte 106 comes into contact with a wick 116 for absorbtion and collection of the analyte 106. The end of the wick 116 adjacent to the nitrocellulose membrane strip 114 may lie over that adjacent end of the nitrocellulose membrane strip 114, as shown in FIG. 1.

Several Flow Immune Assays have been directed toward identifying proteins, molecules of interest, and even immunoglobulins IgG, IgA, and IgM. IgE is an antibody (immunoglobulin E) that is normally present in the blood freely circulating until it moves into the tissue where it is bound to mast cells through the receptor FcERI (F-C-epsilon-R-one) otherwise known as the high affinity IgE receptor. There is a small amount of IgE bound to IgE receptors (high and low affinity receptors) on basophils, eosinophils, and other cells in the blood and tissues.

Many assay systems are geared toward the detection of infectious proteins. All of the aforementioned tests use a non-human antibody—usually IgG type—e.g., goat IgG antibody directed against a protein of interest to detect the protein of interest from the sample (blood, urine, saliva, sweat, etc.). This antibody complexes with protein of interest and forms a complex that travels across the membrane until it reaches the test zone. In the test zone there is an IgG type antibody directed against IgG from that species of animal. As further described herein, the present detecting apparatus and method use human (patient/consumer-derived) antibodies from the sample and the test zone that contains a humanized antibody directed against the protein of interest that is preconjugated to a detecting substance that results in a visual change.

Summary of Target Antigen:
The target antigens may be proteins, glycoproteins, lipoproteins or other molecular substances capable of eliciting an immune reaction and/or being bound by human specific IgE (sIgE).

Immune Assay to Detect Specific IgE:
In the detecting apparatus and method of using the same, the antigens are proteins conjugated to a noble metal, for example, gold, or latex conjugated to antigen in the test zone, for the purpose of detecting the presence of specific IgE (e.g., anti-peanut IgE in a blood sample from a finger prick). For example, an IgG class antibody (IgG1, IgG2, IgG3, or IgG4) or fragments of those classes of antibodies (fab fragments) whose origin may be any animal species (goat, rat, human, etc.) capable of detecting human IgE (anti-IgE IgG)—a suitable commercially available humanized antibody, such as omaluzimab may be used—may be used to form immune complexes of IgG-anti-IgE-sIgE that will migrate to the test zone having selected specific IgE that can bind to the conjugated antigen.

Immune Assay to Detect Total IgE (Not Concerned About Specific IgE):
Another embodiment includes using an IgG class antibody (IgG1, IgG2, IgG3, or IgG4) or fragments of those classes of antibodies (fab fragments) whose origin may be any animal species (goat, rat, human, etc.) capable of detecting human IgE (anti-IgE IgG)—a suitable commercially available humanized antibody that is preconjugated to a detecting molecule that results in a color change when bound to IgE as the target antigen in the test zone.

Figure 2:
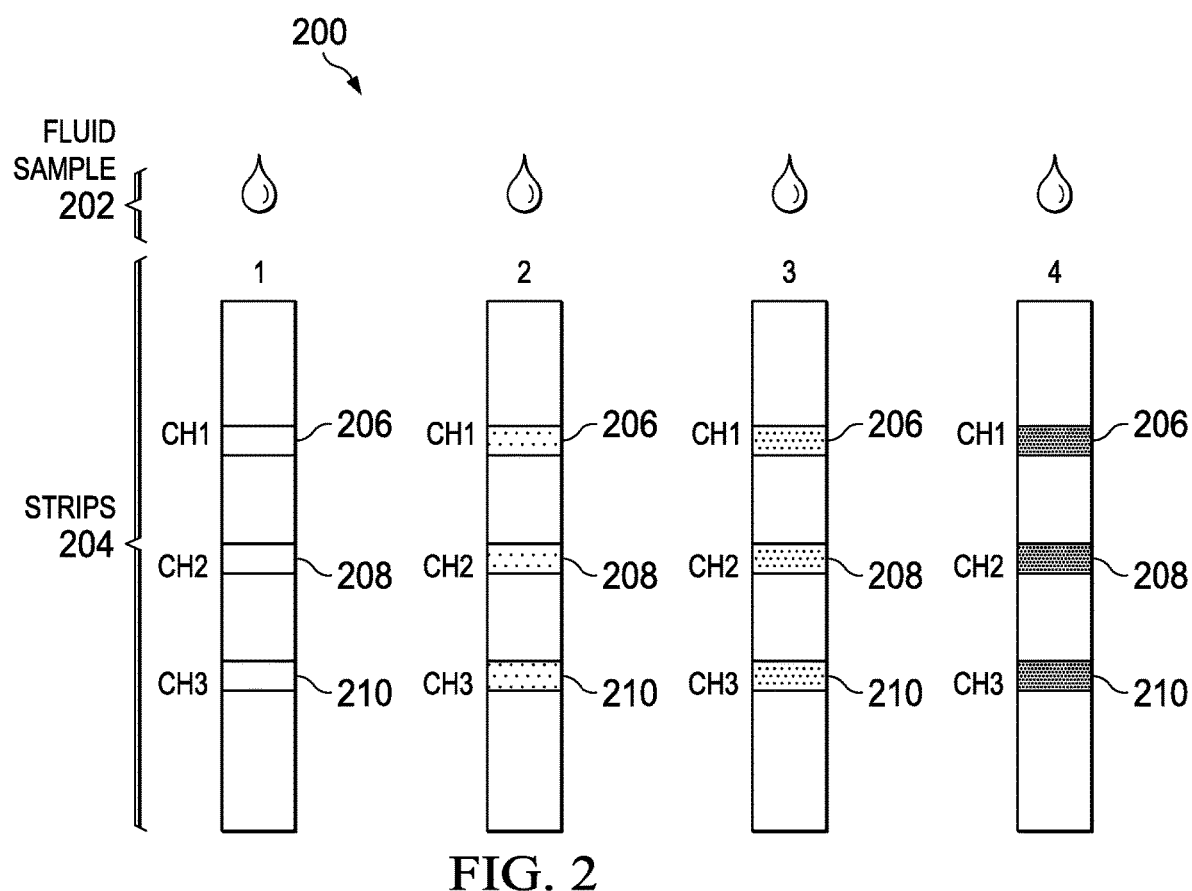
FIG. 2 illustrates a diagrammatic representation of one embodiment of an immunoassay test wherein an analyte is tested across a plurality of test strips.

Referring now to FIG. 2, there is illustrated one embodiment of an immunoassay test 200 wherein an analyte 202 is tested across a plurality of test strips 204. The plurality of test strips 204 may each be configured for testing for a particular antigen. For instance, one strip may be for testing for the presence of streptococcal bacteria (strep throat), one strip may be for testing for a peanut allergy, one strip may be for testing for the Zika virus, etc. Additionally, each strip may also test for multiple antigens. For example, as shown in FIG. 2, multiple testing panels or lines maybe be incorporated. Each line may be for a particular antigen. As shown in FIG. 2, multiple test lines 206, 208, and 208 may be disposed along the plurality of strips 204. A strip testing for allergens may have a panel for testing for peanut allergies shown at test line 206 (CH1), for cat allergies shown at test line 208 (CH2), or grass allergies shown at test line 210 (CH3).

Other examples of configurations for the testing panels can be, but are not limited to: 1) Food 5: Peanut, milk, soy, wheat, egg; 2) Nut and seed panel: almond, cashew, hazelnut, peanut, pecan, walnut, sesame seed, sunflower seed; 3) seafood: crab, lobster, shrimp, salmon, tuna; 4) Pets: cat, dog; 5) Indoor allergens: dust mites, mold mix (alternaria, aspergillus, penicillium, cladosporium), cat, dog; and 6) seasonal allergens: grass (Bermuda, bahia, Johnson, rye, timothy), trees (oak, elm, cedar, mesquite, pine, etc.), weeds (pigweed, ragweed, sage, Russian thistle).

With respect to other non-allergen antigens, the panels may be for testing for strep, Zika, flu, anthrax, cold viruses, cancer, HPV, Lyme disease, mononucleosis (mono), and other illnesses, and/or other conditions such as pregnancy (hCG detection) and disease risks. Some embodiments may allow for the testing of various arboviruses (arthropod-borne viruses). Arboviruses are viruses that are transmitted by arthropods, with mosquitos being a common vector for the virus. Vectors are organisms that transfer the virus from a host that carries the virus. Thus, in the case of mosquitos, a mosquito that feeds on a host that is infected with a virus may infect others when that mosquito again feeds on an uninfected host. Well-known arboviruses include Dengue virus, Japanese encephalitis virus, Rift Valley fever virus, West Nile virus, yellow fever virus, chikungunya, and Zika virus. Urine, blood, and saliva and other biologics may be used for arboviruses testing.

Certain antigens or medical conditions may be logically paired together. For instance, a testing device may include both a strip for detection of pregnancy and a strip for the detection of the zika virus, as the Zika virus has been known to cause birth defects in infants born to pregnant women that are infected with Zika. Thus, combining these two tests into a single testing device or kit would alert a woman to a potential Zika infection proximate in time to the time she also discovers she is pregnant, allowing the woman to seek medical attention immediately. This is a substantial improvement over past Zika testing, where a woman may be required to wait weeks before results are returned from a lab after having the biologic collected by her physician. In many cases, this may lead to a woman having passed a state-mandated cutoff point for abortions, such as 24 weeks in some states. Combining a Zika test with a pregnancy test and physically linking the two tests, and thus allowing for a woman to determine a Zika risk at the time of taking a pregnancy test, in which a pregnancy test may be taken as soon as six days after conception, allows for that woman to take action much sooner than the state mandated cutoff and waiting for lab results would allow.

Various testing devices that include the test strip 100 or strips may be used, such as a slide that supports the test strip 100, a cassette based diagnostic test, a dipstick, or combinations thereof. The test results in various embodiments may be in the form of a visual qualitative reading test, a visual semiquantitative format, a reader quantitative assay format, and/or combinations thereof. Additionally, an electronic implementation may be used where the result is displayed digitally on a screen disposed within the apparatus, and visible to the user.

The apparatus and method of detection may be a "one-step" approach from sample to reading without sample dilution or other sample manipulation. The sample may be diluted or endure other sample manipulation, for example the blood sample is diluted with a buffer.

Figure 3:
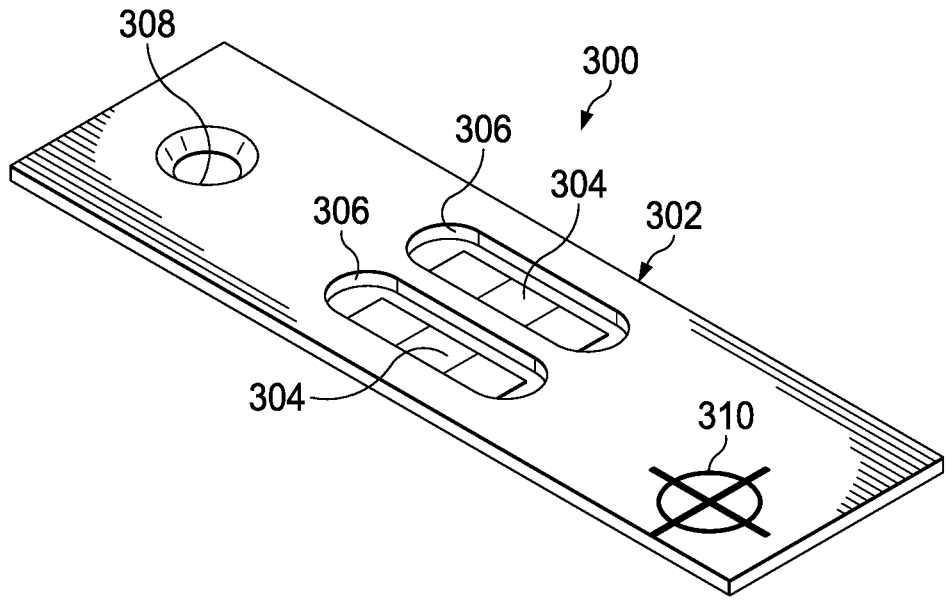
FIG. 3 illustrates a diagrammatic representation of one embodiment of a testing device.

Referring now to FIG. 3, there is illustrated a diagrammatic representation of one embodiment of a testing device 300. The testing device 300 includes a housing 302 that forms the body of the testing device. The housing 302 may be made of plastic, metal, or any material durable enough for shipping and subsequent handling by a user. The housing 302 may be hollow so that a plurality of test strips 304 may be housed within and so that a biologic may be deposited within the housing 302. The testing device 300 may further have a plurality of windows 306, each window being associated with one of the plurality of test strips 304, and allowing for a user to view at least the section of the nitrocellulose membrane strip 114 where the test line 110 and control line 112 are located. The plurality of windows 306 may be open, or covered with plastic, glass, or other materials that allow for viewing the plurality of strips 304. A sample well 308 may be disposed on a surface of the housing 302 to allow a user to deposit a biologic into the housing 302. The sample well 308 would be disposed over or near the sample pad 104 of the test strip or strips 100. In the embodiment shown in FIG. 3, a single sample well 308 is included for collection of a single type of biologic for testing, with each of the plurality of strips 304 being suited for testing for antigens using that particular biologic sample type. For example, if the testing device 300 is a combined pregnancy and Zika test, having both a pregnancy strip and a Zika strip, a urine sample may be deposited into the sample well 308, causing the urine sample to come into contact with the sample pad 104 on both the pregnancy strip and the Zika strip. It will be understood that both of these tests may also be performed with a blood sample.

The testing device 300 may also have disposed on the surface of the housing a crosshair symbol 310, used as an alignment target. This symbol may be a graphic printed or adhered to the testing device 300. The crosshair symbol 310 is used to align the testing device 300 for the taking of an image of the testing device 300 using a camera on a mobile device, for use in a mobile device application described herein. In other embodiments, the crosshair symbol 310 may be other types of symbols, such as a simple shape (circle, square, etc.), other images (such as a medical cross symbol, an arrow, etc.), or any other type of image.

Figure 4:
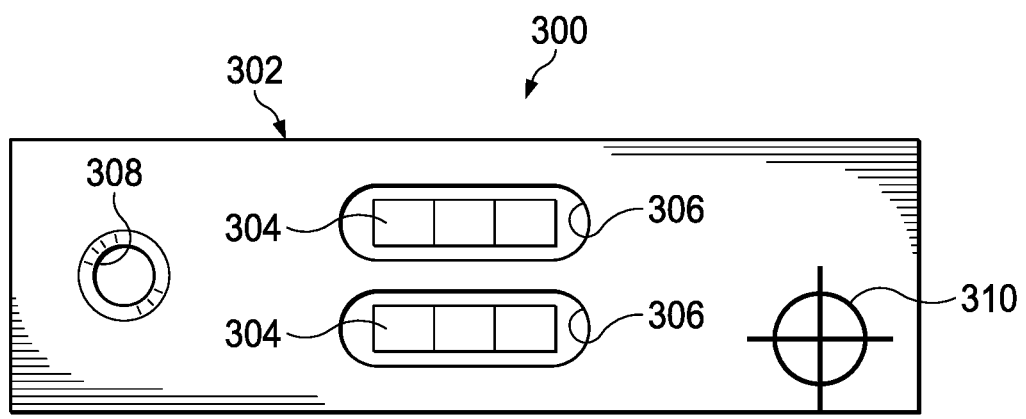
FIG. 4 illustrates a top view of the testing device of FIG. 3.

Referring now to FIG. 4, there is illustrated a top view of the testing device 300. There is again shown the housing 302, the plurality of test strips 304, the plurality of windows 306, the sample well 308, and the crosshair symbol 310.

Figure 5:
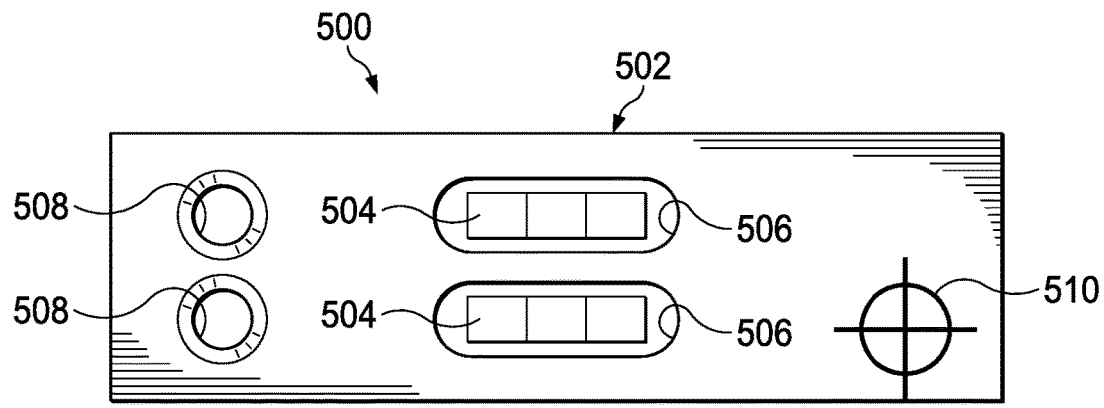
FIG. 5 illustrates a top view of one embodiment of a testing device.

Referring now to FIG. 5, there is illustrated a top view of one embodiment of a testing device 500. The testing device 500 includes a housing 502 having a plurality of test strips 504 within the housing 502 and a plurality of windows 506 for display of the plurality of strips 504. The housing 502 also includes a plurality of sample wells 508 disposed on one side of the testing device 500. Each of the plurality of sample wells 508 is associated with one of the plurality of test strips 504 and each of the plurality of sample wells 508 may be disposed over one of the sample pads 104 on the associated one of the plurality of test strips 504. This allows for a biologic to be deposited into each of the plurality of sample wells 508, with each well 508 serving to transfer the biologic to the test strip underneath the sample well. The testing device 500 further includes a crosshair 510. The crosshair symbol 510 is used to align the testing device 500 for the taking of an image of the testing device 500 using a camera on a mobile device, for use in a mobile device application described herein.

Figure 6:
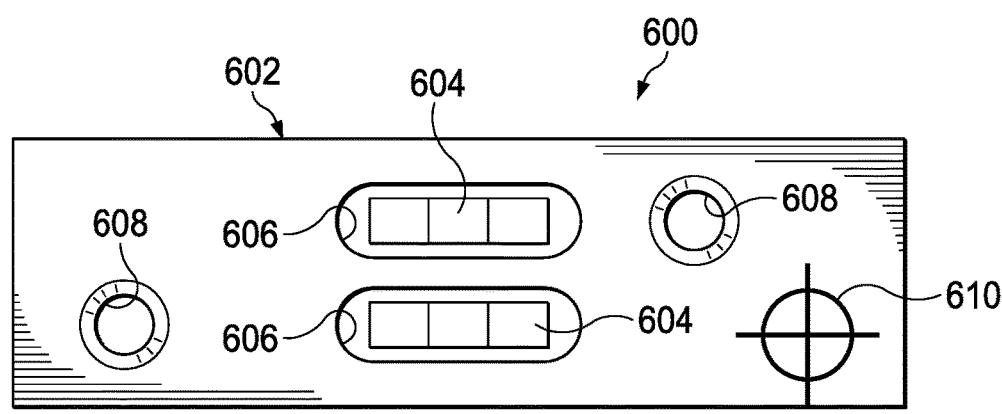
FIG. 6 illustrates a top view of another embodiment of a testing device.

Referring now to FIG. 6, there is illustrated a top view of another embodiment of a testing device 600. The testing device 600 includes a housing 602 having a plurality of test strips 604 within the housing 602 and a plurality of windows 606 for display of the plurality of strips 604. The housing 602 also includes a plurality of sample wells 608. In this embodiment, the sample wells are located on different ends of the housing 602. In the case of a two test strip device, the sample wells 608 are disposed on opposite ends of the testing device 600. The strips 604 would be arranged within the housing in such a way as to allow the sample pad 104 on each of the strip to be disposed underneath one of the sample wells 608. This is useful for testing devices that require different biological samples. For example, if the testing device 600 required a urine sample for one strip and a blood sample for the other strip, having the wells 608 disposed on opposite sides of the testing device would reduce the likelihood that a urine sample, for instance, might be inadvertently deposited into the well designated for the blood sample. In embodiments where there are more than two strips, and more than two wells, the well positions may alternate between the two sides of the testing device. For instance, a first well for a first strip might be disposed on the left side of the testing device, a second well for a second strip might be disposed on the right side of the testing device, a third well for a third strip might be disposed on the left side of the testing device, a fourth well for a fourth strip might be disposed on the right side of the testing device, and so on. The testing device 600 further includes a crosshair 610. The crosshair symbol 610 is used to align the testing device 600 for the taking of an image of the testing device 600 using a camera on a mobile device, for use in a mobile device application described herein.

The diagnostic test can, for example, be produced in a various formats for different users, such as, but not limited to, consumer/in-home use where the test is purchased through retail channels which will allow individuals to get an immediate, cost-effective test result that can lead to specific avoidance and treatment through follow-up with a medical professional.

The diagnostic test can be provided to and used by hospitals and clinics to provide rapid, on-site test results that are required to prescribe certain medications, such as omaluzimab, by their FDA labels.

This diagnostic assay can be modified to detect the presence of specific IgE in pets.

It is also noted that housing 602 is designed such that both strips 604 are disposed in physical proximity thereto and in the same actual housing. In this manner, both sets are linked physically to each other such that they cannot be separated and can be associated with a single individual and the actual test cannot be separated. As such, when a patient applies the specimens to the two areas 608 and the test results are exhibited, there is a high probability that two tests were performed at the same time associated with the same patient. Additionally, and electronic chip (not shown) can be embedded within the housing 602 such that the housing 602 can be registered to a specific patient and associated with the medical records of that patient.

Figure 7:
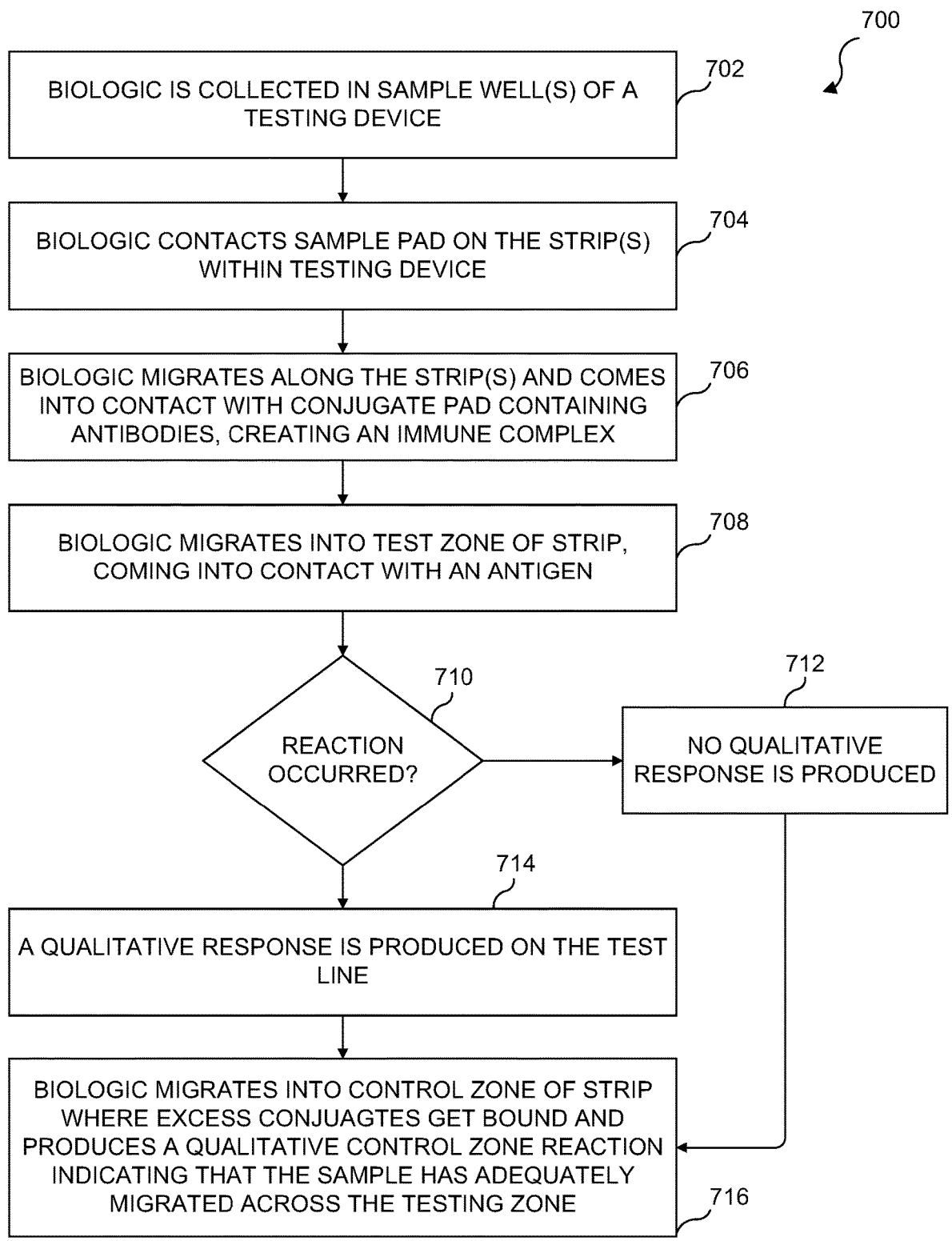
FIG. 7 illustrates a flowchart of one embodiment of a testing device use method.

Referring now to FIG. 7, there is illustrated a flowchart of one embodiment of a testing device use method 700. The method 700 begins at step 702 where a biologic is collected in a sample well or wells of a testing device. The biologic collected may be a non-diluted or non-manipulated biologic, such as blood, urine, or saliva from the user of the test. Diluted or manipulated biologics may be used instead, as required by the specific test. For example, if a viral test requires the biologic to be added to a solution, the biologic could be added to a solution that has previously been placed in a sterilized vial provided with the testing device. After the required amount of time has passed, the solution containing the biologic could be deposited into the well or wells. At step 704, the biologic contacts a sample pad disposed on a strip or strips within the testing device. At step 706, the biologic migrates along the strip or strips to come into contact with a conjugate pad containing antibodies. Antibodies present in the biologic will complex with the antibodies in the conjugate pad to create an immune complex. At step 708, the biologic migrates into a test zone of the strip or strips, coming into contact with an antigen. The antibodies in the conjugate pad serve to provide a means of detection, such as a colored response, if the immune complex binds with the antigen present in the test zone of the strip. At decision block 710, binding of the antibodies with the antigen may or may not occur depending on if antibodies associated with the antigen are present in the biologic or not. If a binding between the antibodies and the antigen does not occur the process moves to step 712 where no qualitative response is produced on the test line. If a binding does occur, at step 714 a qualitative response is produced on the test line. Whether a binding occurs or not, and whether a qualitative response is produced or not, the process moves to step 716 where the biologic migrates into a control zone of the strip or strips where excess conjugates get bound and produces a qualitative control zone reaction indicating that the sample has adequately migrated across the testing zone.

It will be understood by one skilled in the art that the antibodies and antigens applied to the testing strip may be altered depending on the type of condition being tested. For example, in the case of testing for medical conditions that do not involve an illness or infection, like pregnancy, and thus the sample biologic does not contain antibodies associated with the condition, antibodies that react to markers being tested for may be applied to the testing strip instead of an antigen. For instance, pregnancy test requires testing for the presence of hCG. Since hCG is a hormone and not an antibody produced in response to an infection, the testing strip may have antibodies that will react to the presence of hCG applied to the testing zone or line of the testing strip, as well as to the conjugate pad. Similarly, some tests might require antibodies be applied to the testing strip to detect antigens present in the sample, rather than antibodies.

Figure 8A:
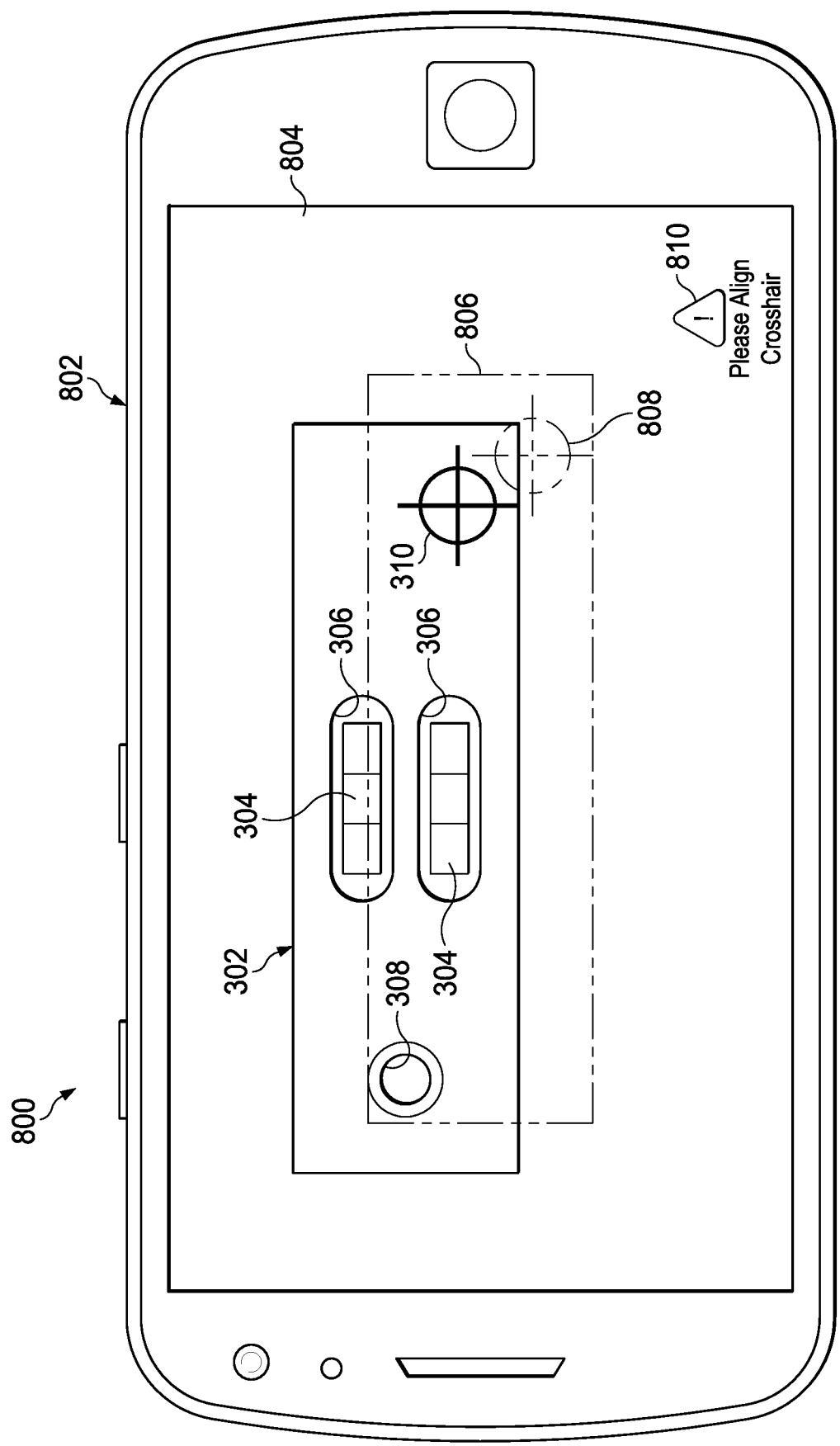
FIG. 8A illustrates a diagrammatic representation of one embodiment of a process for a mobile device application for testing device image capture and image processing, wherein an image alignment indicator is not aligned with the subject of the image.
Figure 8B:
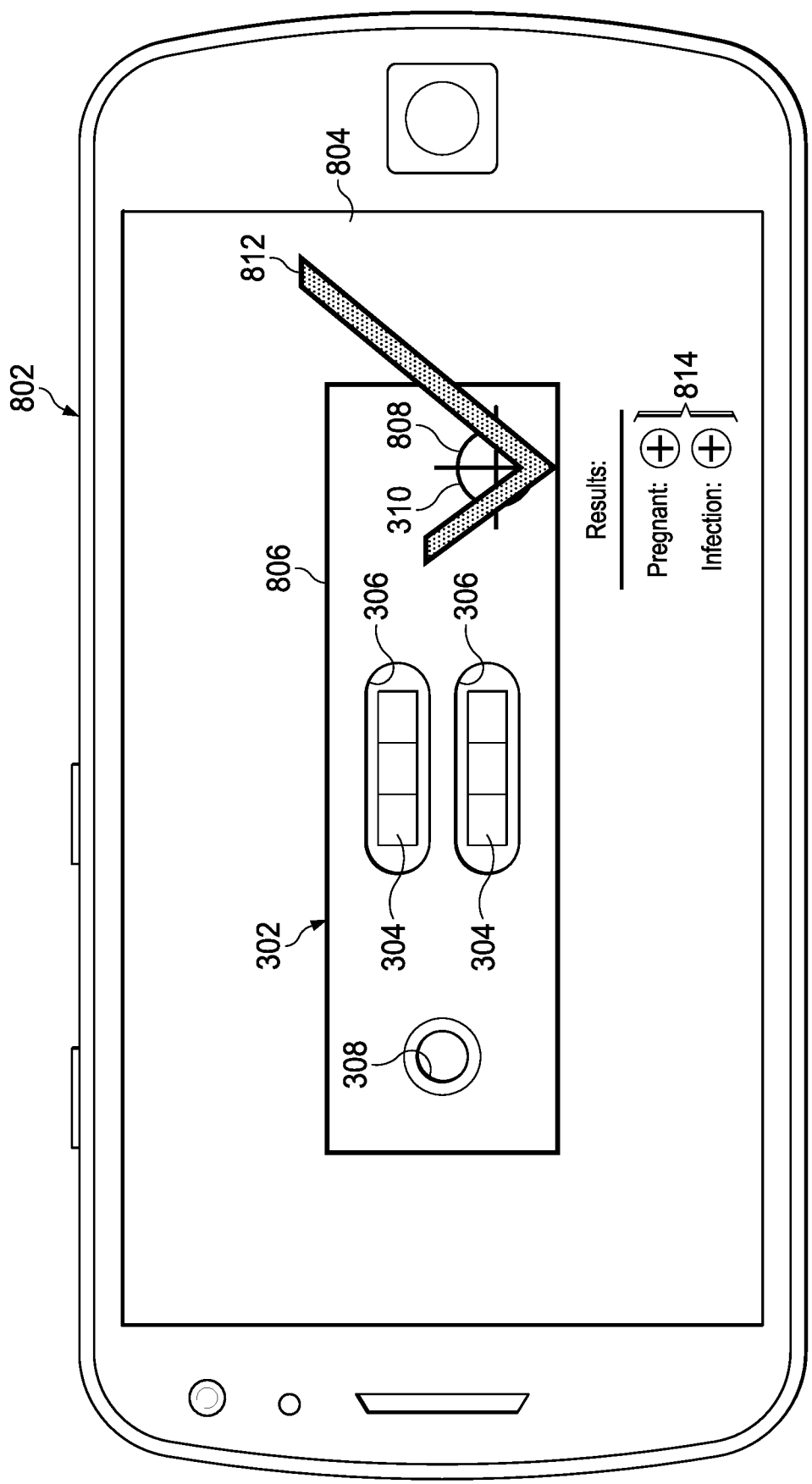
FIG. 8B illustrates a diagrammatic representation of one embodiment of a process for a mobile device application for testing device image capture and image processing, wherein an image alignment indicator is aligned with the subject of the image.

Referring now to FIGS. 8A and 8B, there is illustrated a diagrammatic view of one embodiment of a process 800 for a mobile device application for testing device image capture and image processing. The mobile device application allows for an image of a testing device, such as testing device 300, to be captured using a camera installed on a mobile device 802 having a screen 804. While the mobile device 802 displays on the screen 804 the scene captured by the camera, the mobile device application also displays a graphic on the screen 804 in the form of a boxed outline 806, the size of the outline 806 corresponding to the size of the testing device 300. Also displayed on the screen of the mobile device 802 within or near the outline is a crosshair graphic 808. A user of the mobile device 802 attempts to align the outline 806 with the borders of the testing device 300 and also attempts to align the crosshair graphic 808 with the crosshair 310 on the testing device 300. While alignment has not yet been achieved, a misalignment warning 810 may appear on the screen of the mobile device 802, indicating to the user that alignment has not yet been achieved. Such is shown in FIG. 8A.

In FIG. 8B, there is shown the result of a successful alignment of the outline 806 with the testing device 300 and successful alignment of the crosshair graphic 808 with the crosshair 310 on the testing device 300. As shown in FIG. 8B, once aligned, a success indicator 812 may appear, such as a check mark or other positive status symbol, on the aligned image. Successful alignment causes the camera on the mobile device 802 to capture the current image of the testing device 300. Other checks may occur, including ensuring that the image is focused before the image is saved. This image is then processed to determine a result based on the severity of the reaction occurring on the test strip. The mobile device application performs an analysis of the test line captured in the image, counting the number of colored pixels, as well as determining the intensity of the color. The mobile device may then compare this number and color intensity to that in the control line, providing a mathematical evaluation of the test line. Utilizing unique wavelengths of light for illumination in conjunction with either CMOS or CCD detection technology, a signal rich image is produced of the test lines to detect the colloid gold or latex particles. This provides an advantage because a user simply looking at the two lines may not know what the test line indicates, such as when the colored line does appears on the strip, but it is a faded line, rather than a dark line. Based on this analysis, the mobile device application may provide a results indicator 814.

The results indicator 814 may be a qualitative result or a quantitative result. For example, and as shown in FIG. 8B, a qualitative result for the results indicator 814 may indicate, in the case of a testing device for testing pregnancy as well as an infection, a plus sign next to a line reading "pregnant:" and a plus sign next to a line reading "infection:" to indicate that the user is both pregnant and infected with the bacteria or virus being tested, such as the Zika virus. For a quantitative result, the results might provide a numeric rating. For instance, a rating system between 1-100 may be used. If the results provide a low rating to the user, such as a rating of 10, this indicates a low risk of infection, although medical attention may be sought by the user anyway. For example, if the user is pregnant, and also receives a 10 rating for Zika, this may indicate that Zika was detected in low amounts. However, the user may still seek medical attention or further testing from her doctor because Zika has been known to cause birth defects. If the rating is a high rating, such as 95, this indicates that an infection has most likely occurred and medical attention should be sought immediately.

This same quantitative rating system may be applied to any test (viral infections, bacterial infections, pregnancy, and other health conditions), as the quantitative test can be performed using the software described herein to accurately test bound antibody concentrations on the test strip. In some embodiments, a combined qualitative and quantitative result may be presented, such as both a rating and a plus or minus sign being presented, or other types of quantitative and qualitative indications. Additionally, various combinations of tests may be provided for in the testing device, such as pregnancy/Zika, pregnancy/flu, pregnancy/strep/Zika, etc.

Figure 9:
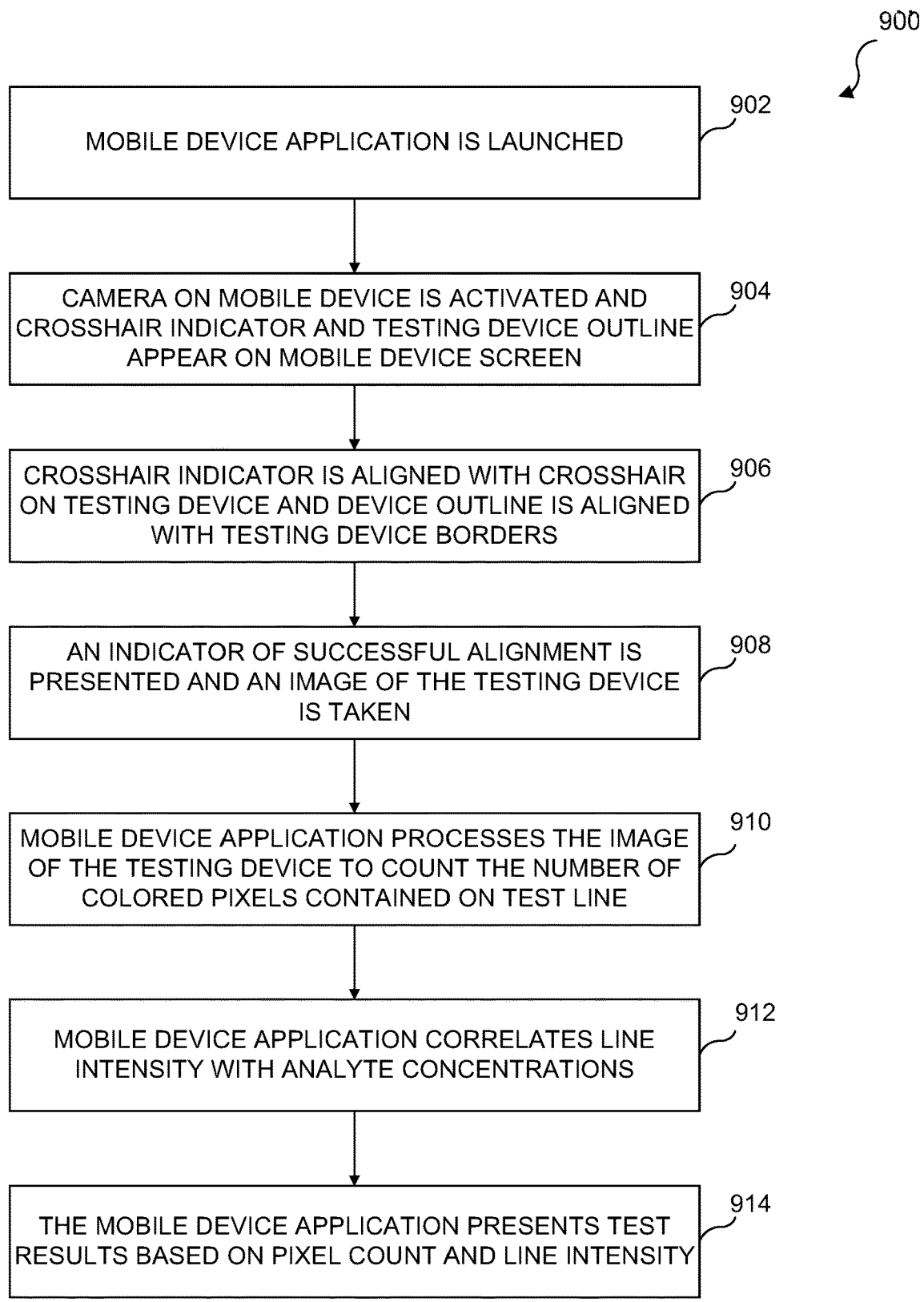
FIG. 9 illustrates a flowchart of one embodiment of an image analysis process using a mobile device.

Referring now to FIG. 9, there is illustrated a flowchart of one embodiment of an image analysis process 900 using a mobile device. At step 902 a mobile device application is launched. At step 904 a camera on the mobile device is activated and a crosshair indicator and a testing device outline appear on the mobile device screen. At step 906 the crosshair indicator presented on the screen of the mobile device is aligned with a crosshair icon on the testing device and the device outline presented on the screen of the mobile device is aligned with the borders of a testing device. At step 908, an indicator of successful alignment is presented on the screen and an image of the testing device is taken by the mobile device camera. At step 910, the mobile device application processes the image of the testing device to determine test line strength by counting the number of colored pixels contained in the test line. At step 912, the mobile device application correlates line intensity with analyte concentrations to further determine test line strength. At step 914, the mobile device application presents the test results based on pixel count and line intensity, providing either a qualitative or quantitative result.

In some embodiments, the number of pixels indicating bound antibodies on the strip may be measured against that in the control line to compare line intensity between the two lines, with the control line acting as an example of a strong reaction, indicating a strong infection, and determining how close the test line intensity is to the control line. This would lead to a logical quantitative result. For instance, if the test line is determined to have a pixel count and line intensity that is 25% of the pixel count and line intensity of the control line, a rating of 25 may be given. If a qualitative result is to be provided, a rating of 25 may give a qualitative result that is negative, or it could be positive depending on the type of condition being tested and known actual infection results where a rating of 25 occurred for that condition.

In some embodiments, the test line may not be compared with the control line to determine a result. Rather, the mobile device application may have access to a database having data on numerous past tests for the same condition. This data may instead be used as the control. This allows the application on the mobile device to retrieve data on past tests and compare the test line data of the current test to past tests. Overall data for past tests may be provided and compared against, such as providing an average or a curve of past tests, or individual tests rated as having accurate results may be compared against.

In addition to a status result of an infection or other medical condition being provided to the user, other indicators of health may also be tested and results thereon provided. This provides for potential early identification of pregnancy and risk of morbidity, allowing for medical attention to be sought much more quickly. Indicators of health may be detected from biologics, such as urine and blood. Urine, for example, allows for the detection of glucose levels, proteins, bacteria, and infectious markers. In the case of glucose, glucose is usually not found in urine, but, if it is, that is an indicator of extremely high levels of glucose in the body, where the kidneys release excess glucose into urine. This is often a sign of diabetes. Protein in the urine may indicate a malfunctioning of the kidneys, which could be the result of high blood pressure. Similarly, if blood is detected in urine, it could be a sign of a problem with the kidneys or the bladder. Blood, for example, allows for the detection of glucose, inflammation, hormones, genetic defect risks, and metabolic endocrine disorders.

Figure 10:
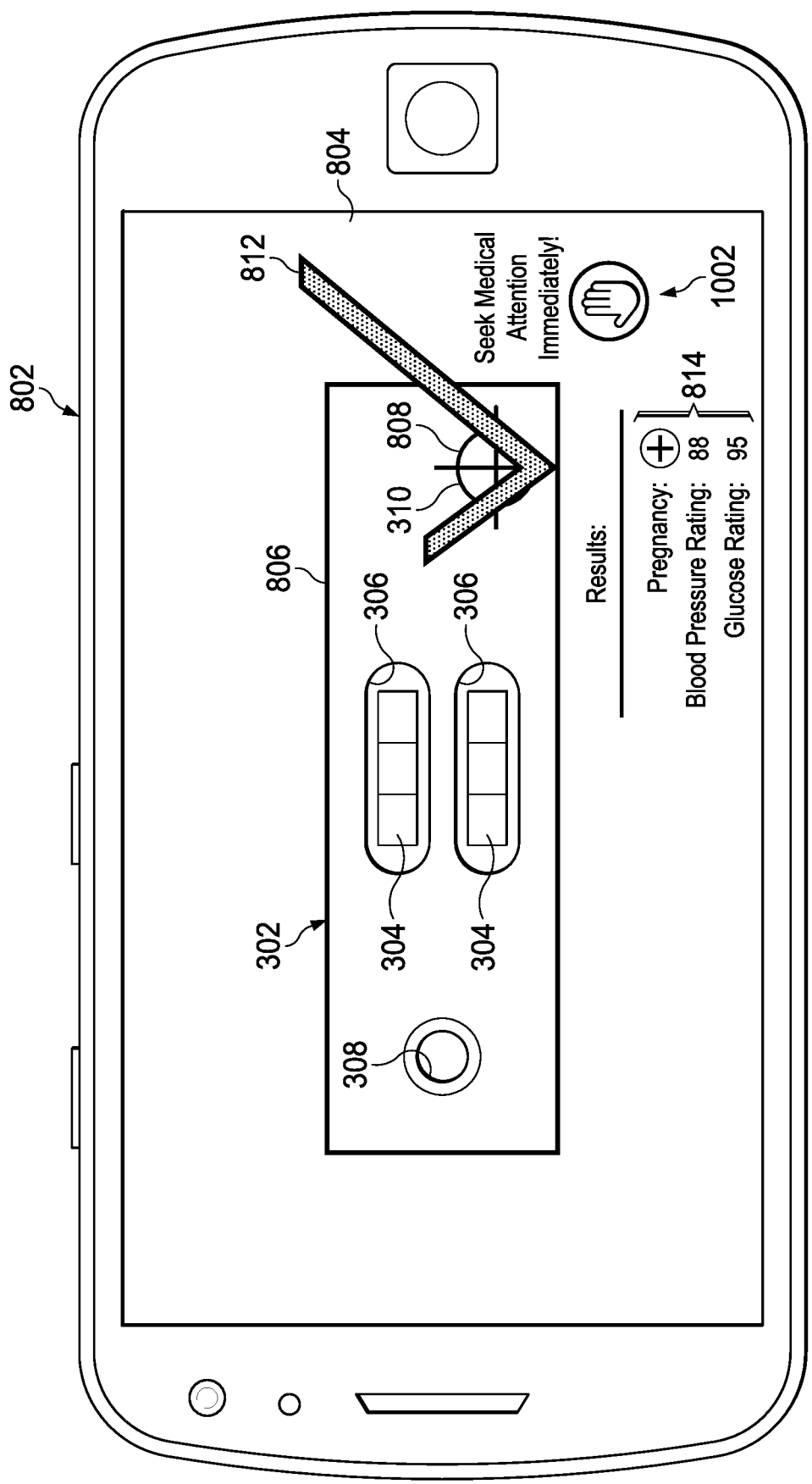
FIG. 10 illustrates a diagrammatic representation of another embodiment of a process for a mobile device application for testing device image capture and image processing, wherein an image alignment indicator is aligned with the subject of the image.

Referring now to FIG. 10, there is illustrated another embodiment of a successful alignment of the outline 806 with the testing device 300 and successful alignment of the crosshair graphic 808 with the crosshair 310 on the testing device 300, wherein quantitative results for health risk indicators are provided. In this embodiment, the results indicator 814 provides a qualitative result for pregnancy, and quantitative results for other health risk indicators. In the embodiment shown in FIG. 10, the health risk indicators being tested are markers for blood pressure and for glucose levels. For blood pressure, this is a test for markers in the blood that can be associated with high blood pressure. These could be test for such things as low levels of vitamin D and the such. Studies have shown that patients suffering from essential hypertension will be under oxidative stress and Malondialdehyde (MDA) is the principal and most studied product of polyunsaturated fatty acid pre-oxidation. This can show an indirect correlation with anti-oxidants, particularly with superoxide dismutases (SODs) (r=0.573) and catalase (r=0.633) representative anti-oxidant are involved in reducing the stress of a patient's biological system during hypertension. Another marker for hypertension is buildup of uric acid, where in uric acid is a marker for xanthine oxidase-associated oxidants and that the latter could be driving the hypertensive response. Additional markers are cortisol, a hormone. The test strips 604 can test for the different biological markers.

The results indicator 814 provides numeric ratings, in this case, 1-100, with the blood pressure rating being 88 and the glucose rating being 95. This indicates that both blood pressure and glucose are extremely high. Due to this, an additional alert indicator 1002 is presented to the user on the screen of the mobile device, alerting the user to seek medical attention immediately. This is to ensure that the health of both the pregnant woman and the fetus can be checked as close to the time of pregnancy detection as possible and medical attention received if needed.

Figure 11:
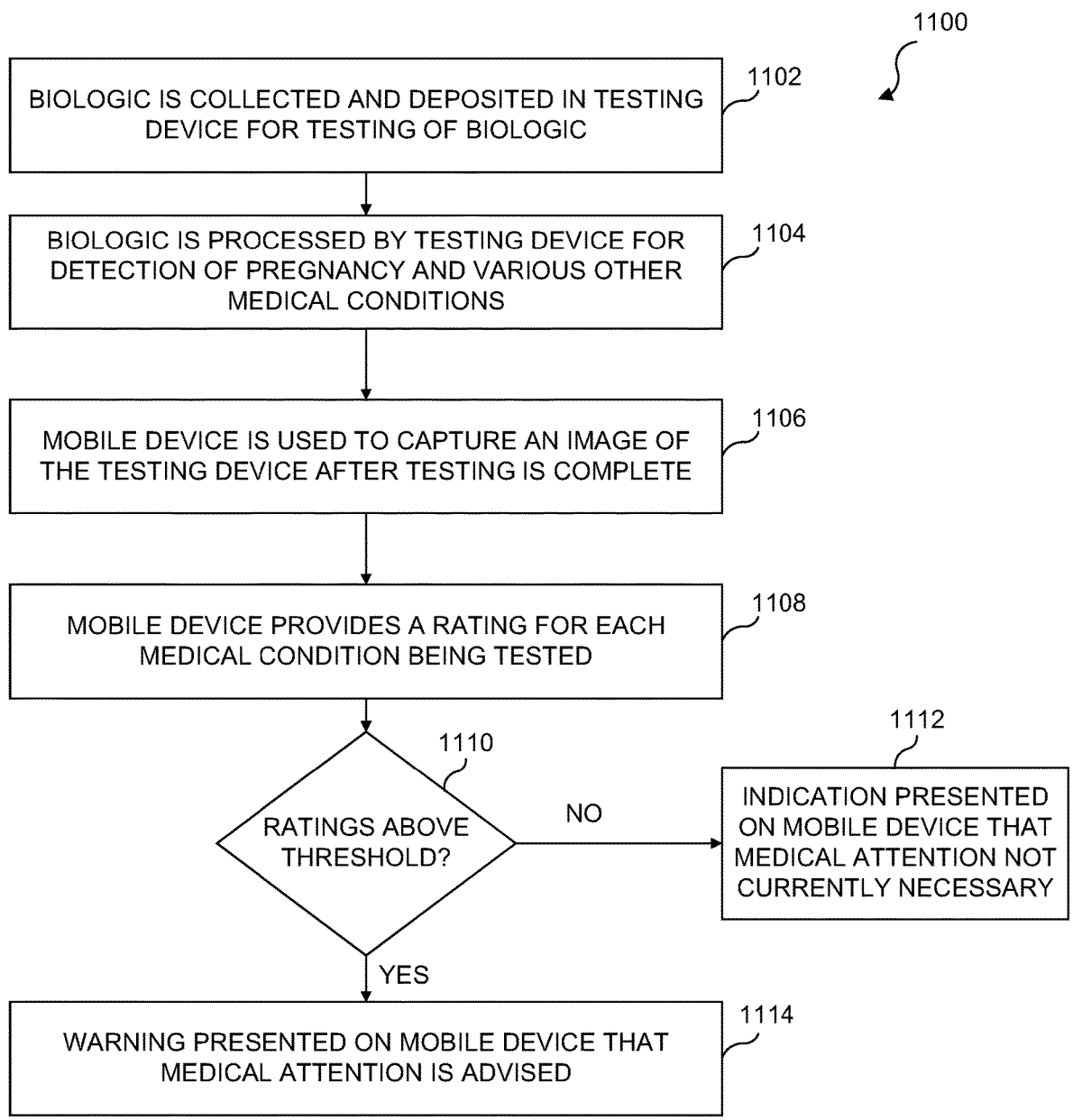
FIG. 11 illustrates one embodiment of a consumer driven biologic and disease data collection system.

Referring now to FIG. 11, there is provided a flowchart of one embodiment of a pregnancy disease risk assessment process 1100. The process 1100 begins at step 1102 where a biologic is collected and deposited in a testing device for testing of the biologic. At step 1104, the biologic is processed by the testing device for detection of pregnancy and various other medical conditions. These medical conditions may be high blood pressure, diabetes, bacterial or viral infections, inflammation, an increase in hormone levels, genetic disease markers, and/or metabolic disorders. At step 1106, a mobile device is used to capture an image of the testing device after testing is complete. In some embodiments, test results may be immediate. In other embodiments, and depending on the medical conditions being tested, the test may take a certain amount of time to complete. In this case, the user of the test would be alerted to this fact in instructions provided with the testing device. Additionally, a visual indicator on the testing device may alert the user that a test is now complete. At step 1108, the mobile device provides a rating for each medical condition being tested, such as that described with respect to FIG. 10 herein.

At decision block 1110, it is determined whether the ratings for each condition exceed a certain threshold for that condition. If not, the process 1100 moves to step 1112, where an indication is presented to the user via the mobile device screen that medical attention is not currently advised or necessary. If at step 1110 it is determined that at least one of the medical conditions being tested rises above a certain threshold, the process 1100 moves to step 1114 where a warning is presented to the user via the mobile device screen that medical attention is advised. The thresholds for medical conditions may not trigger a warning even if a rating exceeds a threshold, if, in the event of multiple tests being performed, the combined test results do not warrant immediate medical attention. For example, if a user is testing for a cold virus, blood pressure, and glucose, and only the cold virus rating is above the threshold, there may not be a warning provided to the user. Additionally, ratings may be weighted or aggregated based on the medical conditions being tested. For example, if blood pressure, inflammation, and glucose are being tested for, and they all are given only moderate ratings that do not rise above the threshold for any condition individually, an warning to seek medical attention may still be provided due to the combination of conditions taken together.

Figure 12:
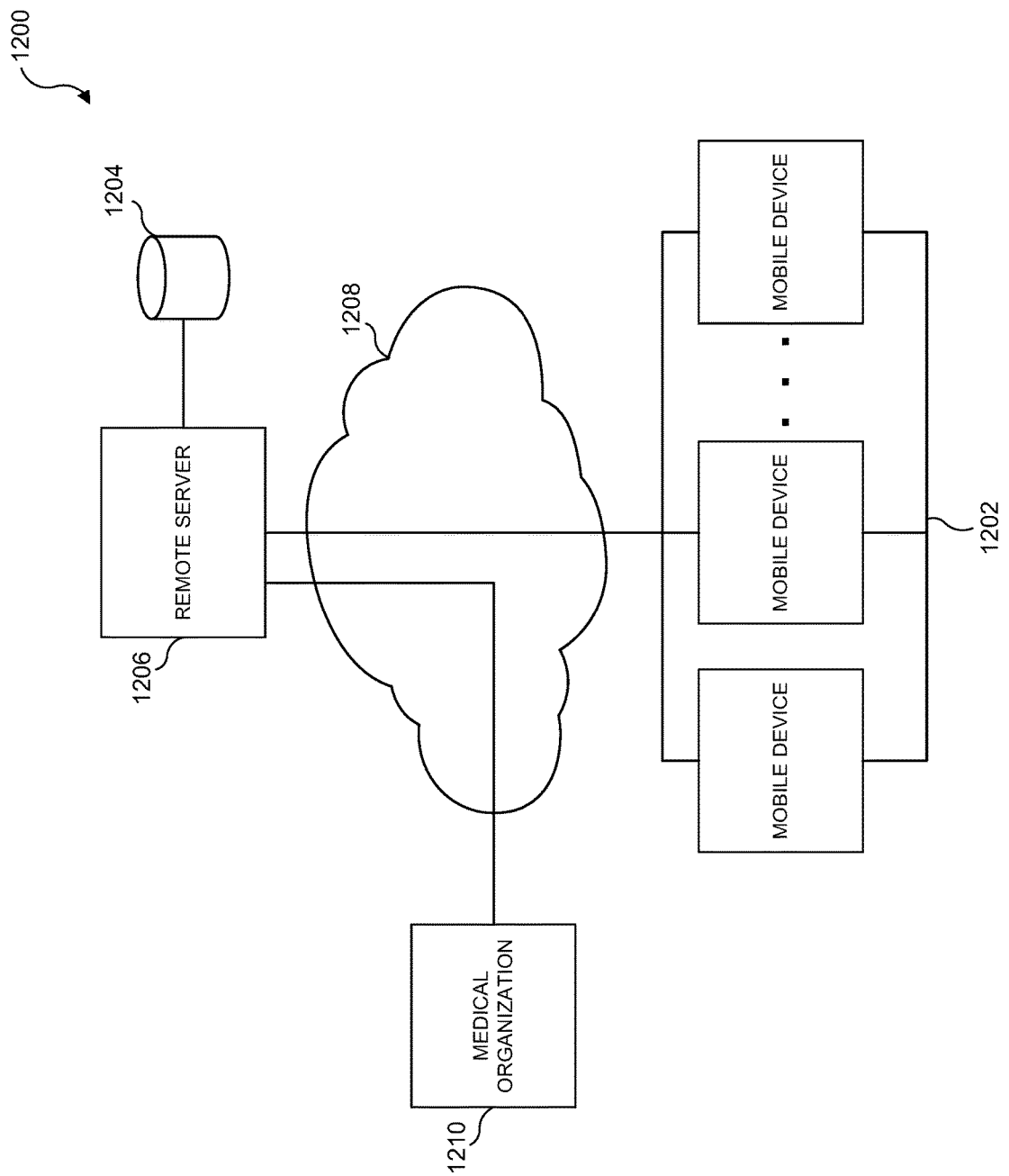
FIG. 12 illustrates one embodiment of a consumer driven biologic and disease data collection system.

Referring now to FIG. 12, there is illustrated one embodiment of a consumer driven biologic and disease data collection system 1200. Data collected from users performing the tests disclosed herein effectively can provide a wealth of information. As tests are performed data may be passed by a plurality of mobile devices 1202 being used by users performing tests to a database 1204, the database being at a remote server 1206, over a network 1208. The user is sourcing a biologic from user's own body. This is done at home, not in a lab, hospital, or clinic. Each particular test would expect a certain type of biologic to be provided. For instance, for a pregnancy test, a urine sample is provided and tested for pregnancy markers. For a stool test, the stool might be dissolved in a vial with a solution provided with the testing device/kit, and tested for various disease or infectious markers. Data and results from the tests may be stored on the database 1204 at the remote server 1206. As described herein, this data may be used as a control for testing analysis for users of the plurality of mobile devices 1202. This data may also be used to provide data sets for biologics to a medical organization 1210. The medical organization 1210 may be doctor's offices, researchers, hospitals, testing labs, and other individuals or organizations that have an interest in the health and analysis of users taking the test and of their biologic samples. In this way, data can be gathered from a variety of biologics tested for a variety of different medical conditions and characteristics.

Figure 13:
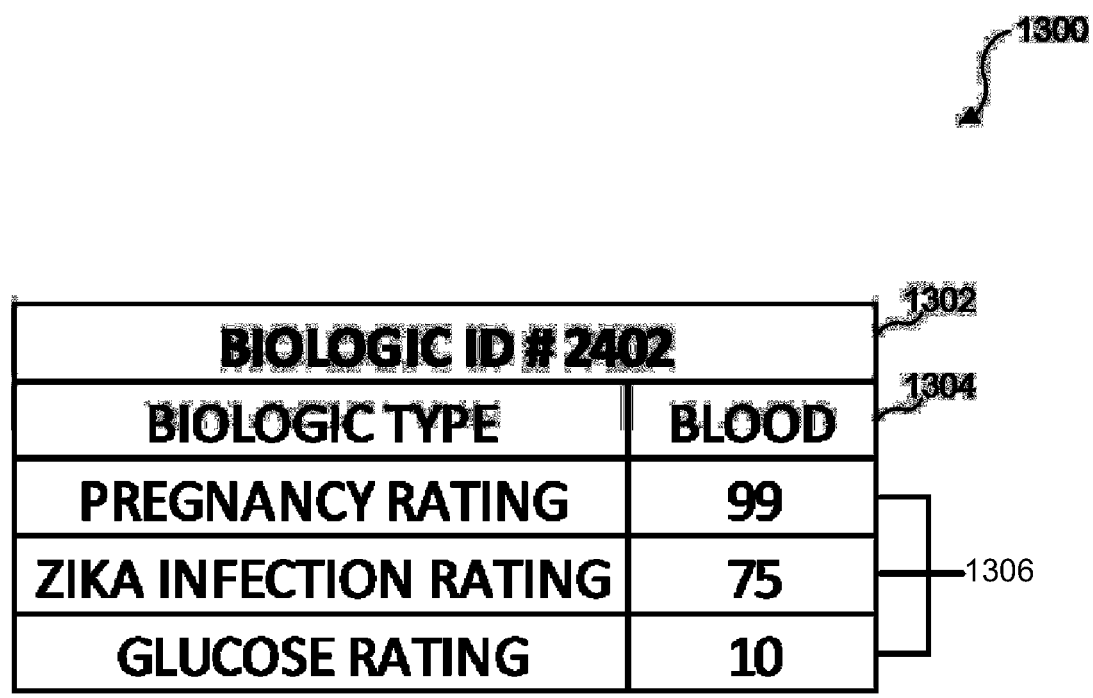
FIG. 13 illustrates an example of a unique biologic ID database table.

Referring now to FIG. 13, there is illustrated an example of a unique biologic ID database table 1300. The table 1300 is illustrative of the type of data stored in association with data for a biologic transmitted by the plurality of mobile devices 1202 for storage on the database 1204. A biologic ID header 1302 is provided that shows that the biologic sample has been given a unique ID. All data concerning the biologic may be stored in association with the unique biologic ID. The table 1300 also includes a biologic type entry 1306. This designates what type of biologic that the biologic associated with the unique ID is, such as blood, urine, stool, saliva, sweat, or other biologics. The table 1300 also provides a plurality of test ratings 1304, for various tests performed on the biologic. In the example shown in FIG. 13, a blood biologic is provided having an assigned ID of 2402, and having been testing for pregnancy markers, the Zika virus, and for glucose levels. The rating for pregnancy was a 99 rating, the rating for a Zika infection was a 75, and the rating for glucose levels was a 10. This would indicate that the test subject has an extremely high likelihood of both a pregnancy and a Zika infection, which would have resulted in a warning to seek medical attention at the conclusion of the tests. Other information may also be stored in the database in relation to the biologic, including other condition ratings, time and date each test was performed, user information such as ethnicity, gender, and age, and status indicators such as whether a test subject visited a physician as a result of the tests. The database 1204 thus provides the test subject with a growing collection of information that may be accessed by the test subject. This allows the test subject to present the test results to her physician for medical attention or additional testing, and allows for others who may access the database, such as disease researchers, to have access to data on various biologic samples and their markers.

Figure 14:
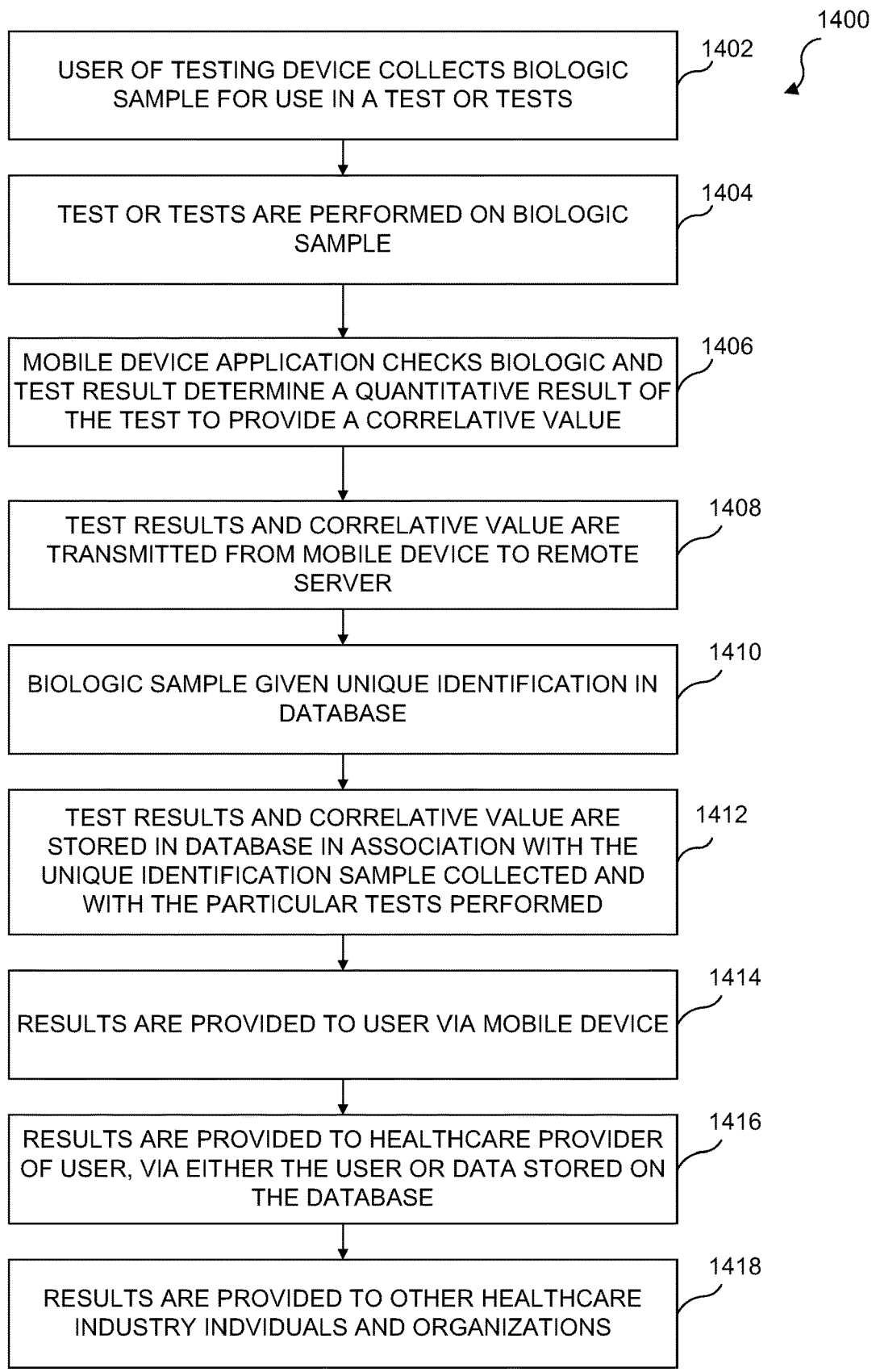
FIG. 14 illustrates a flowchart of one embodiment of a biologic data collection and dissemination process.

Referring now to FIG. 14, there is illustrated a flowchart of one embodiment of a biologic data collection and dissemination process 1400. The process 1400 begins at step 1402 where a user of a testing device collects a biologic sample for use in a test or a series of tests. At step 1404, the test or series of tests are performed on the biologic sample. At step 1406, a mobile device application checks the biologic sample the testing device result to determine a quantitative result of the test to provide a correlative value for the condition being tested in the biologic sample. At step 1408, the test results and correlative values, or multiple values if multiple tests on the biologic sample were conducted, are transmitted to the remote server 1206. At step 1410, the biologic sample is given a unique identification number in the database 1204. At step 1412, the test results and correlative value or values are stored in the database 1204 in association with the unique identification number given to the biologic sample collected and in association with the particular tests performed. This way, the particular biologic sample may have various characteristics stored and retrieved in association with the biologic sample, and the test results may also be retrieved when data on a particular test is needed on a cross-section of users.

At step 1414, the results are provided to the user on the user's mobile device. At step 1416, the results are provided to the user's healthcare provider. The healthcare provider may receive the test results due to a visit from the user, the user bringing the results of the test with her on her mobile device, or the healthcare provider may receive the results from the database 1204 if the healthcare provider has permission to access the database 1204, or if access is granted in anticipation of the user's appointment with the healthcare provider. At step 1418, the test results are also provided to other healthcare industry individuals and organizations, including medical researchers, hospitals, and others.

Figure 15:
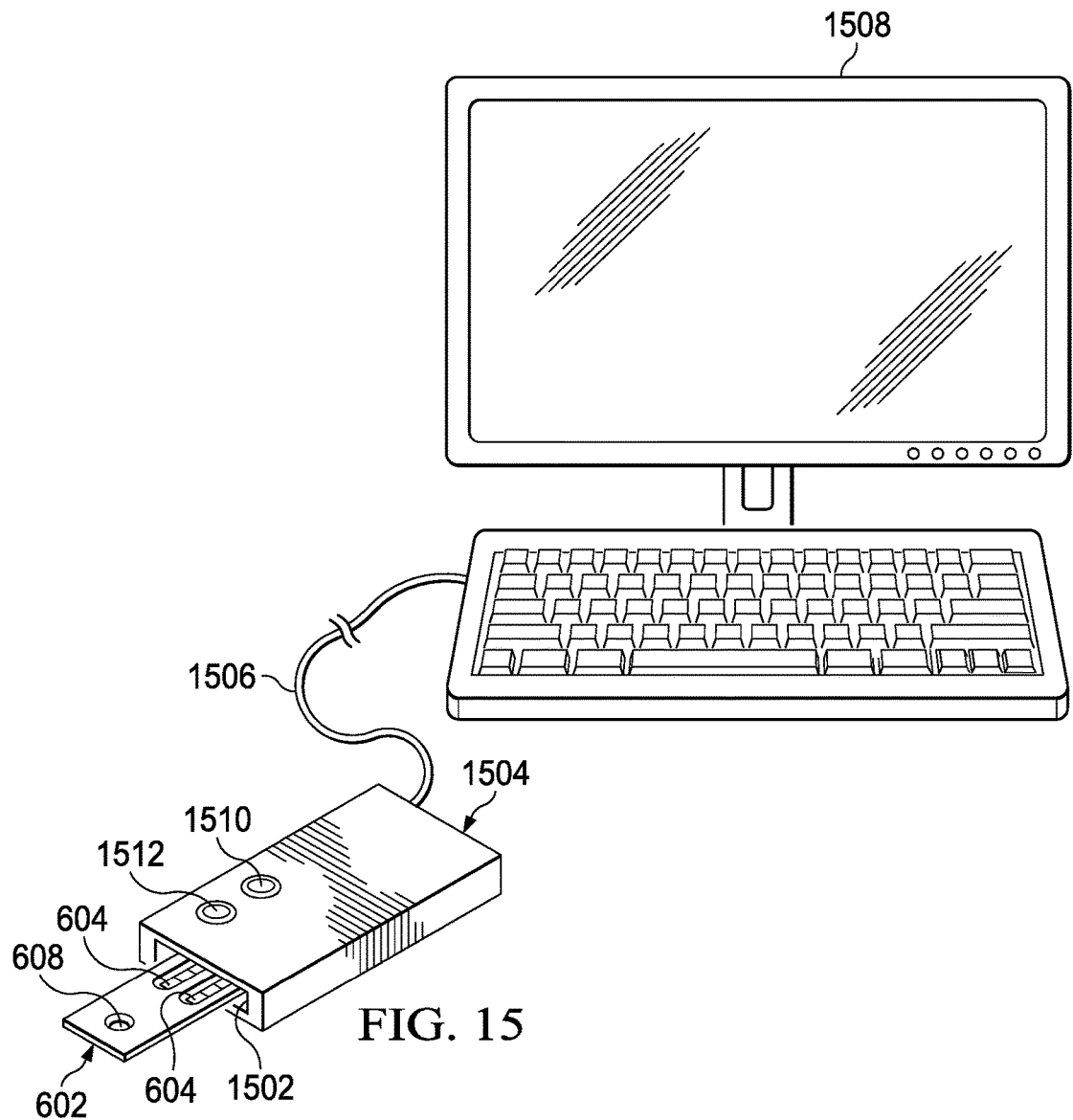
FIG. 15 illustrates a perspective view of a system for scanning test strips.

Referring now to FIG. 15, there is illustrated a perspective view of a system for scanning test strips. The housing 602, as described hereinabove with respect to FIG. 6, is illustrated as being disposed within a slot 1502 in a test housing 1504. The test housing 1504 is connected through a line 1506 to a PC 1508. When the housing 602 containing the test strips 604 after being subjected to the biologics is inserted within the slot 1502, the test housing 1504 will scan the test strips 604 and analyze the results with the PC 1508. The PC 1508 will run some type of algorithm that can analyze the results of both of the test strips 604. There can be provided to indicators 1510 and 1512 on the surface of the test housing 1504, one being, for example, a ready LED and one being a green LED. The PC 1508, after analyzing results, can then provide a warning indicator such as lighting up the green LED for a positive indication of pregnancy and the red LED for indicating that there is some issue. As an example, suppose that the second test strip tested for the Zika virus. If so, a warning would be appropriate to output and activate the red LED. There could be any other type of indicator associated with the second test at 604 that, in a combination with the test results of the first test strip, i.e. for testing for the presence of a pregnancy state, testing for such things as diabetes, etc. Further, although only two test strips 604 are illustrated, there could be multiple test strips testing for many different biological issues that may be present in an individual. In this embodiment, by inserting the housing 602 into the test housing 1504 and allowing the PC 1508 to analyze the results, the indicators associated with the test strips can be analyzed with the assumption that all of the test return results were associated with an individual and in proximate time to each other. That means that the individual patient applied biological specimens, such as urine, blood, etc., to the appropriate test strips and, since these were all contained within the same test strip housing 602, this provides an indication that they are associated with a single patient. Further, the test performed will typically be a test that will provide a very short-term response. Thus, the specimens can be applied to the test strips 604 in the test strip housing 602 and then inserted within the slot 1502 for testing by the PC 1508.

Figure 16:
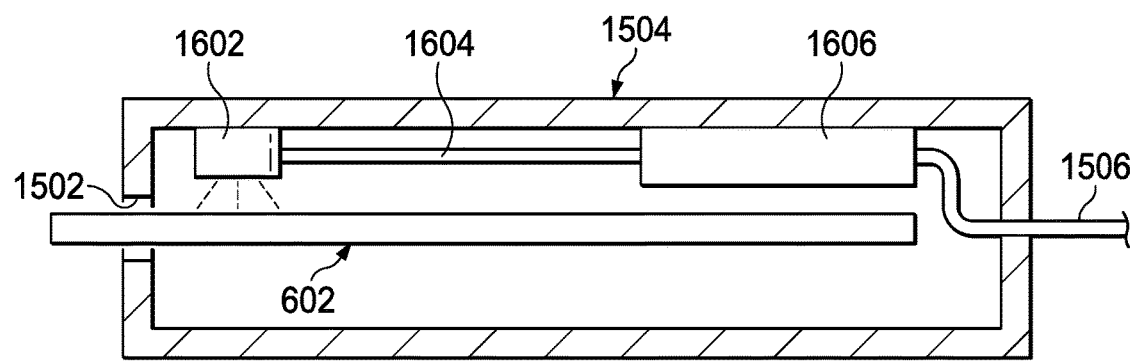
FIG. 16 illustrates a cross-sectional view of the system of FIG. 15.

Referring now to FIG. 16, there is illustrated a cross-section of the test housing 1504. It can be seen that the test strip housing 602 is passed in slot 1502 past the camera 1602. The camera 1602 is operable to scan a small cross-section of the test strips 604 on the surface thereof as the test strip housing 602 passes thereby. Of course, there could also be a much larger camera provided for taking an entire image of the test strips 604 after being inserted within the test housing 1504. The camera 1602 is connected via a wire 1604 two in electronics package 1606 to process the information and send it to the PC 1508. The electronics package 1606 will also drive the indicators 1510 and 1512.

Figure 17:
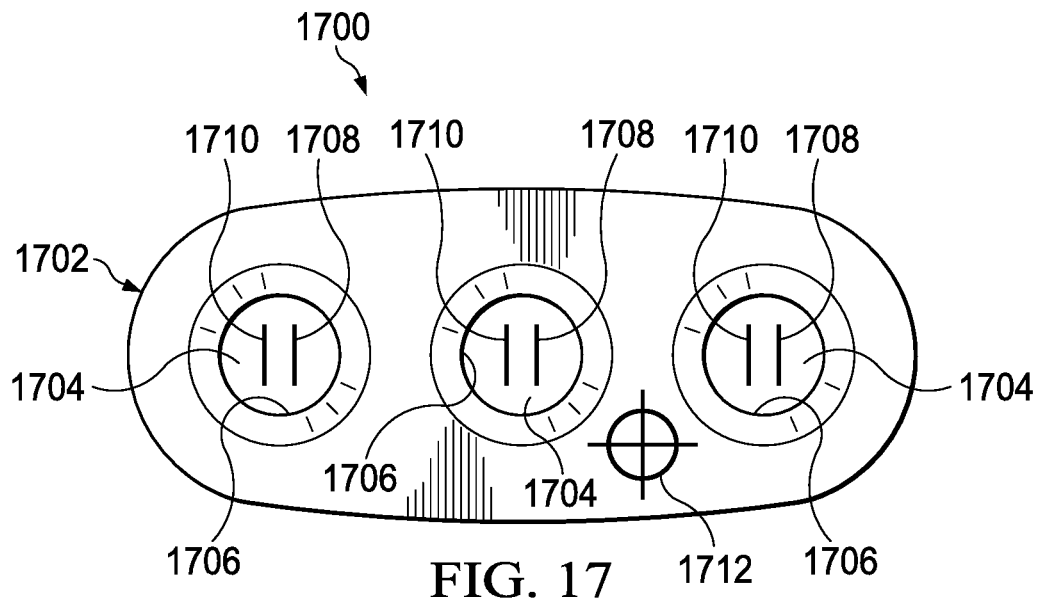
FIG. 17 illustrates one embodiment of a vertical flow immunoassay device.

Referring now to FIG. 17, there is illustrated one embodiment of a vertical flow immunoassay device 1700. It will be understood that testing device 300 and other embodiments herein illustrate a lateral flow immunoassay device. However, other types of immunoassay devices may be used. For example, vertical flow immunoassay devices may be used, a two-sided flow through assay, or even a sandwich ELISA test may be run.

The testing device 1700 includes a housing 1702 that forms the body of the testing device. The housing 1702 may be made of plastic, metal, or any material durable enough for shipping and subsequent handling by a user. The housing 1702 may be hollow so that a plurality of immunoassay test pads 1704 may be housed within and so that a biologic may be deposited within the housing 1702. The testing device 1700 may further have a plurality of sample wells 1706, each sample well having one of the plurality of immunoassay test pads 1704 disposed within, and allowing for a user to view at least a section of a nitrocellulose membrane of each of the immunoassay test pads 1704, the membrane having a test line 1708 and control line 1710. The testing device 1700 may also have disposed on the surface of the housing a crosshair symbol 1712, used as an alignment target. This symbol may be a graphic printed or adhered to the testing device 1700. The crosshair symbol 1712 is used to align the testing device 1700 for the taking of an image of the testing device 1700 using a camera on a mobile device, for use in a mobile device application described herein. In other embodiments, the crosshair symbol 1712 may be other types of symbols, such as a simple shape (circle, square, etc.), other images (such as a medical cross symbol, an arrow, etc.), or any other type of image. In other embodiments, the device 1700 may be configured in such a way as to allow a biologic sample to be deposited into a sample well, and to present the results of the test on the opposite side of the housing. Such a configuration would allow the biologic to flow through the testing pad within the housing, with the reaction occurring on a reactive membrane on the side of the device opposite the sample well, with the device having a window for viewing the results.

Figure 18:
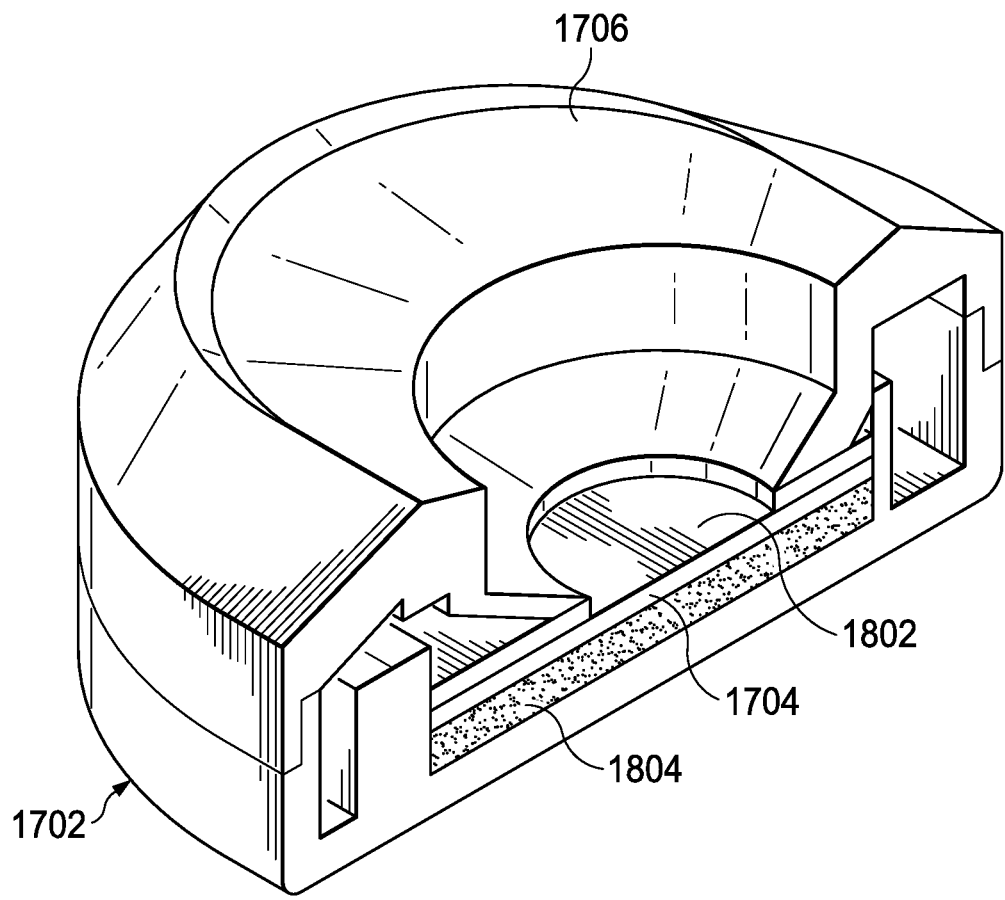
FIG. 18 illustrates a cross-sectional view of one embodiment of the vertical immunoassay device of FIG. 17.

Referring now to FIG. 18, there is illustrated a cross-sectional view of one embodiment of the vertical immunoassay device 1700. There is shown one of the plurality of immunoassay test pads 1704 residing within the housing 1702 below one of the plurality of sample wells 1706. The one of the plurality of immunoassay test pads 1704 includes a immunoreactive membrane 1802, such as the nitrocellulose membranes disclosed herein. The immunoreactive membrane 1802 may have particle conjugates disposed thereon that binds when a biologic sample is received onto the immunoreactive membrane 1802 via the sample well 1706, if the biologic sample contains the antigens or antibodies, or other indicators, for which the test is configured. The one of the plurality of immunoassay test pads 1704 also includes an absorbent pad 1804 for collection of excess biologic sample. It will be understood that the cross-sectional view illustrated in FIG. 18 shows one well of the plurality of sample wells 1706. The other wells included in the device 1700 would be configured in a similar manner as that shown in FIG. 18. There may also be included in the device 1700 an inner separating wall between each of the plurality of immunoassay test pads 1704, to ensure that excess biologic material that is not adequately absorbed by the absorbent pad 1804 does not contaminate neighboring immunoassay test pads.

Figure 19:
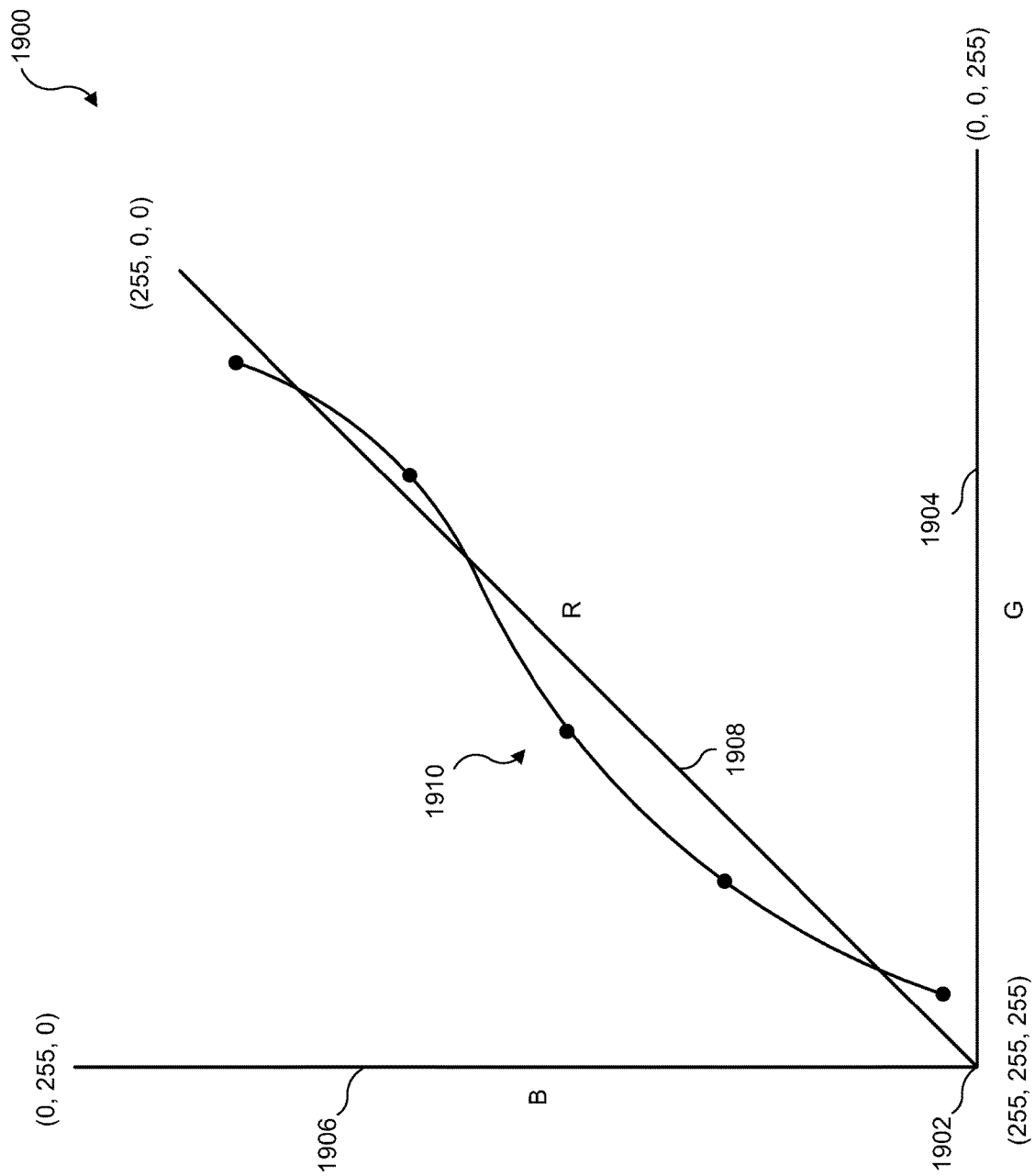
FIG. 19 illustrates a color gradient chart.

Referring now to FIG. 19, there is illustrated a color gradient chart 1900. When the mobile application described herein captures an image of the testing device, in some embodiments each pixel that makes up the test line captured in the image is processed to place it on a color gradient scale. In some embodiments, this placement may be done by examining the RGB values of the pixel. For any given test, there may be a visual color indicator (such as a test line) presented to the user of the test to indicate whether a reaction occurred. The color that is to be presented is known for the given test. Additionally, in some embodiments, the strength of the reaction will affect the strength of the color indicator. For example, if a test is supposed to produce a brown colored indicator, an image can be taken of the colored indicator to examine each pixel of the colored indicator to determine the strength of the color produced on the testing device, which indicates the strength of the reaction, and thus the risk level for the user.

The embodiment illustrated in FIG. 19 uses as an example a set of pixel RGB results for a test that produces a red colored indicator on the test strip when a reaction has occurred. There can be seen an origin point 1902 on the chart 1900, wherein the RGB value is (255, 255, 255) or white. This may represent a no reaction state for the test strip, since the test line on the strip may only appear as a white blank space if no reaction has occurred. An x axis 1904 represents the color green, wherein the amount of green in the pixel decreases as it moves away from the origin in relation to the x axis 1904. A y axis 1906 represents the color blue, wherein the amount of blue in the pixel decreases as it moves away from the origin in relation to the y axis 1906. A diagonal line 1908 running in between the x axis 1904 and the y axis 1906 represents the color red, wherein the diagonal line 1908 running through the center of the chart 1900 is a maximum red color all along the diagonal line 1908. If a pixel has less red than a 255 value, the pixel would be plotted away from the diagonal line 1908 in relation to whichever color is more predominant. For instance, if the pixel has RGB values of (127, 50, 205), a shade of purple, the pixel would be plotted somewhere in the lower right quadrant of the chart 1900. FIG. 19 further illustrates an example plurality of pixel plot points 1910, connected by a curved line, wherein the example plurality of pixel plot points 1910 shows tests results that likely indicate a positive reaction, as the plot points are all located near the diagonal line 1908, demonstrating that the colored indicator was a heavy red color for the most part.

Figure 20:
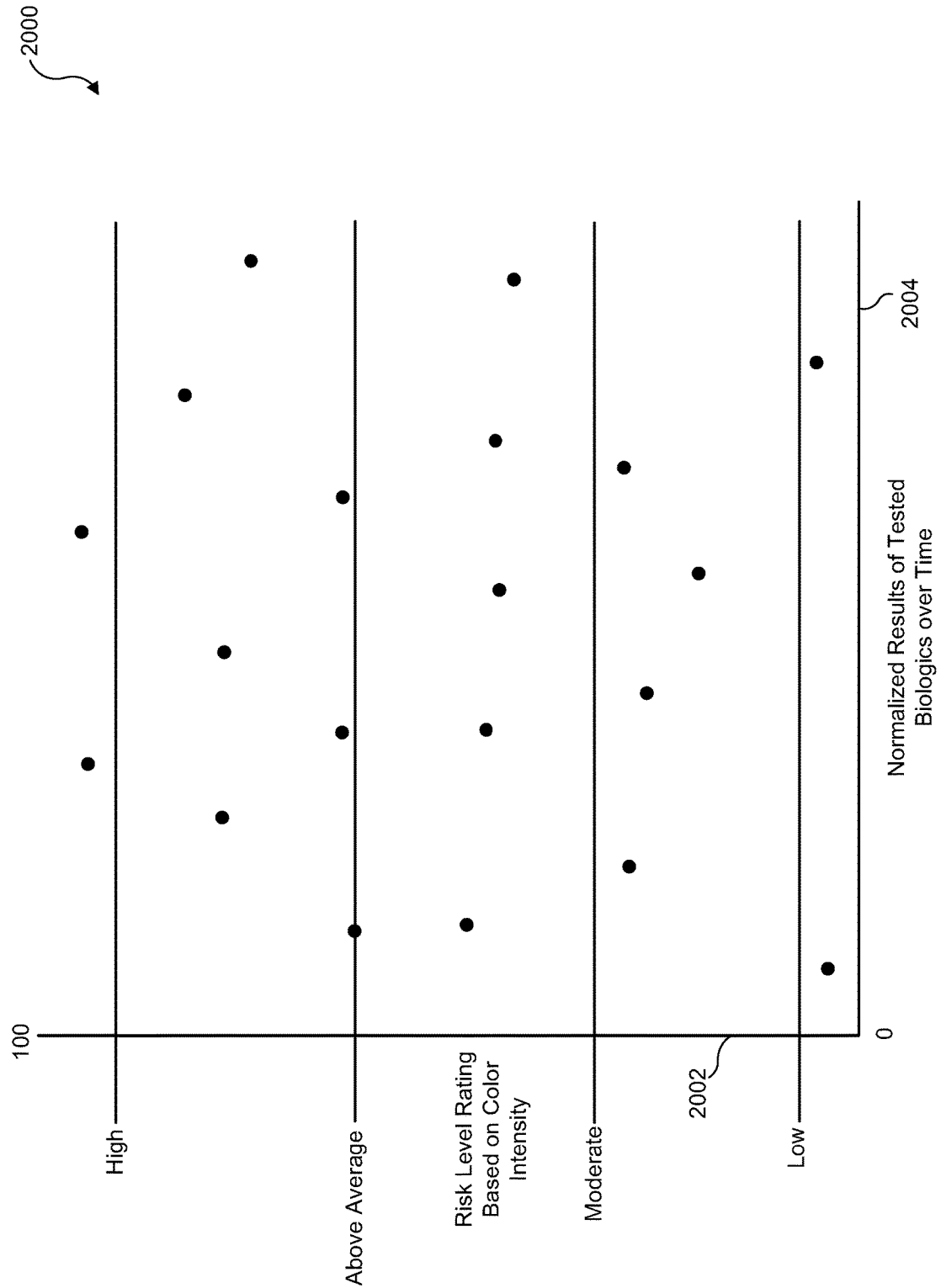
FIG. 20 illustrates a normalized past tests results rating chart.

Referring now to FIG. 20, there is illustrated a normalized past tests results chart 2000. The captured pixels may be normalized into a single value for determining whether there is a likelihood of infection, pregnancy, or whatever else the test is designed to detect. This may be done in various ways. For example, the shade of red in all the pixels may be averaged to reach a single RGB value. Outliers may be left out so that the average is not heavily skewed, especially when there are few outliers present. This RGB value may then be given a value, such as a risk rating, ranging from 0 to 100. For example, an RGB value of (255, 255, 255) would be given a rating of 0. An RGB value of (255, 0, 0) would be given a rating of 100. An RGB value of (205, 150, 75) may be given a rating of 70, and so on. This normalized value may then be used to compare the user of the test to users of past tests to determine a risk level. In some embodiments, the control line and the test line may be captured and the results compared, as well. In addition, the real results of risk levels may also be used to adjust the stored normalized value. For instance, if a particular RGB value that seems to indicate a strong reaction repeatedly was found to not indicate an infection, this value may be adjusted to provide a lower risk rating. For instance, if a physician who saw a patient who had a (205, 150, 75) RGB value later reported to the operator of the server 1206 that further testing showed no infection was present, and if this trend continued substantially as reported by other physicians or medical organizations, subsequent test results by other test users that were near the RGB value of (205, 150, 75) may be given a lower rating.

Chart 2000 illustrates how past tests results may be collected and used to determine the risk of a current test user. A y axis 2002 represents a risk level rating, ranging from 0 at the origin to 100. An x axis 2004 represents time, wherein a plurality of normalized test results is plotted on the chart 2000. The chart 2000 is further divided into sections across the y axis 2002, indicating various risk level thresholds. For instance, and as illustrated in the chart 2000, there may be at certain rating levels different thresholds of risk labeled as low, moderate, above average, and high risk levels. These thresholds may be moved over time as more data is accumulated via users conducting tests and the mobile application storing the data on the tests. When a user conducts a test, the user's normalized rating can be plotted similarly to past test results and weighed against them in order to provide a risk level for the user.

Figure 21:
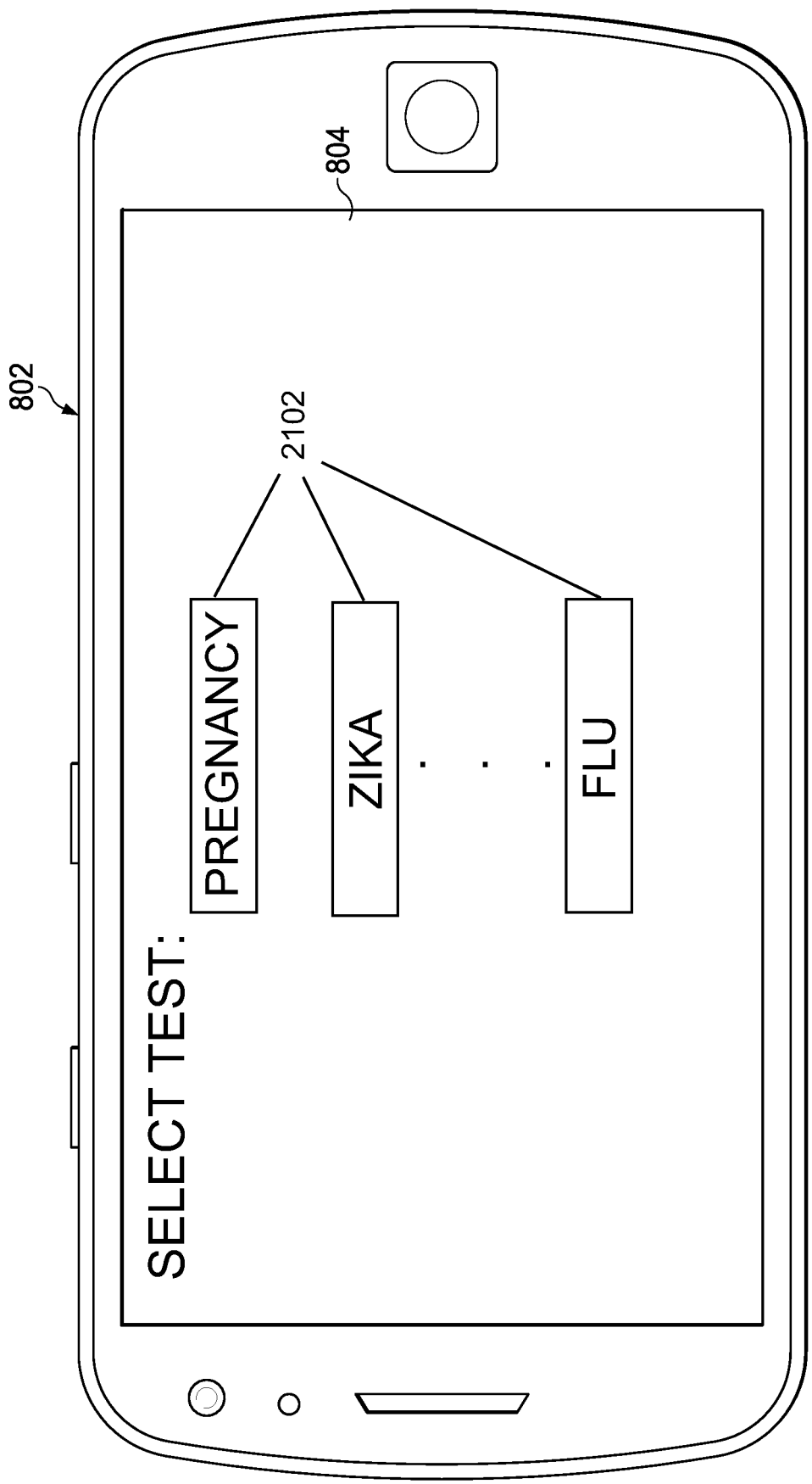
FIG. 21 illustrates a mobile device displaying on a screen a mobile application variable test functionality.

Referring now to FIG. 21, there is illustrated the mobile device 802 displaying on the screen 804 a mobile application variable test functionality. There is displayed on the screen 804 a plurality of test functions 2102. The plurality of test functions 2102 may be buttons that can be selected by a user to switch between tests within the mobile application. This allows for all test functions to be within the same mobile application. For each test run by the mobile application, data for the particular test chosen is utilized in performing the test, pulling the data from the remote server 1206.

Figure 22:
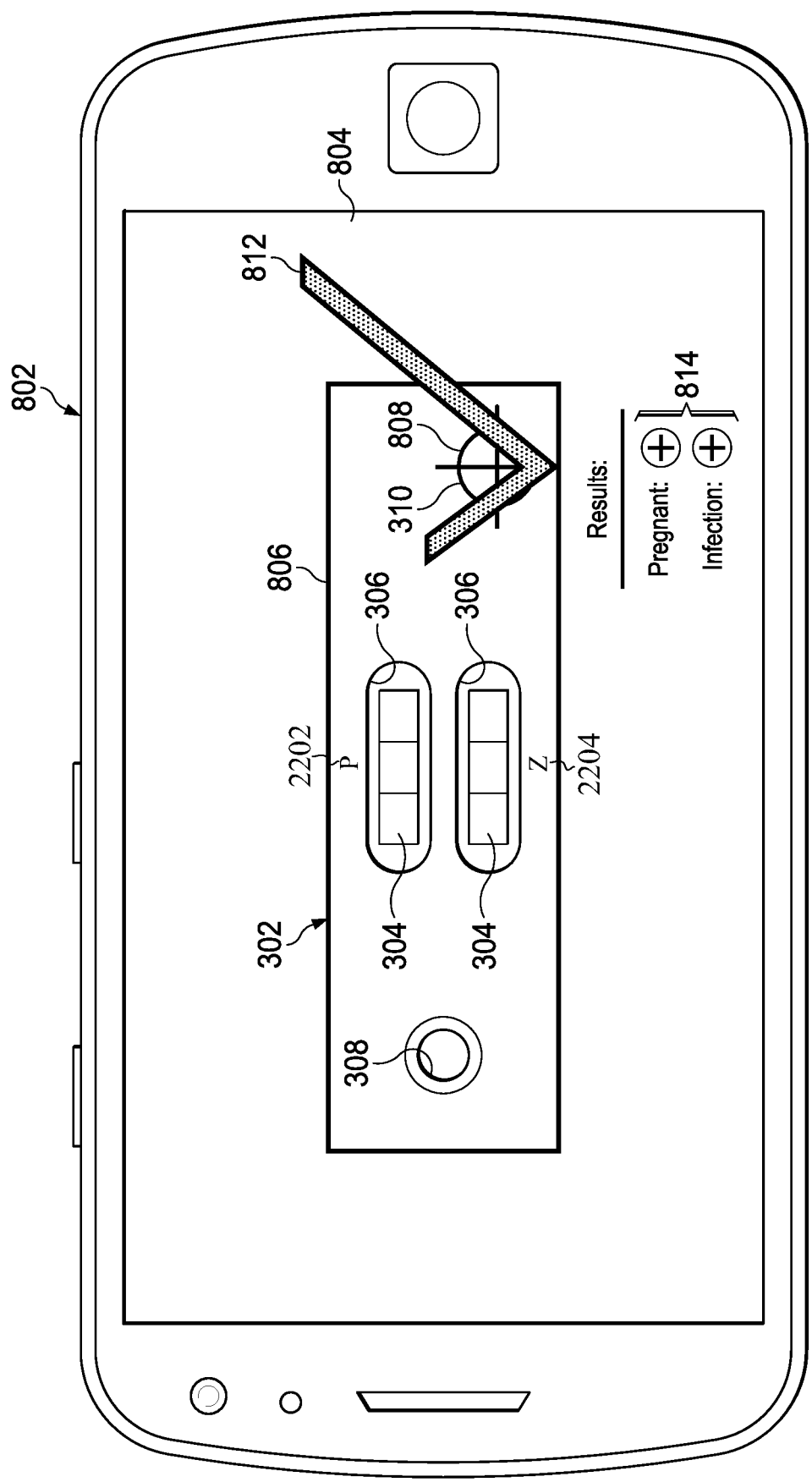
FIG. 22 illustrates the mobile device of FIG. 21, wherein a housing of a testing device also includes thereon test function indicators.

Referring now to FIG. 22, there is illustrated the mobile device 802 of FIG. 8B, wherein the housing 302 of the testing device 300 also includes thereon test function indicators 2202 and 2204. The test function indicators 2202 and 2204 are visual markers located on the housing 302 that identify to the mobile application the types of tests for which the testing device 300 is configured. These indicators may be any symbol, alphanumeric character, shape, etc. that can be added to the surface of the testing device 300. The mobile application is programmed to recognize the indicator and perform the test function associated with the indicator. For example, the embodiment illustrated in FIG. 22 shows a "P" symbol for test function indicator 2202 and a "Z" symbol for test function indicator 2204. In this embodiment, test function indicator 2202 indicates that one test strip in the testing device 300 is a pregnancy test, while test function indicator 2204 indicates that one test strip in the testing device 300 is a Zika test. This is used for merely illustrative purposes, and any recognizable symbol may be used for these two test functions, and any other type of test may have a symbol assigned in this way as well. Further, in some embodiments there may only be one indicator on the housing 302, even if there are multiple tests. This single indicator would be for the combined test. For example, if the testing device 300 of FIG. 22 had a single symbol of "PZ," this would indicate that the testing device 300 is a combined pregnancy and Zika testing device, allowing for the mobile application to recognize such and perform each test with knowledge of which strip is associated with which test based on the stored data on the testing device associated with the "PZ" symbol.

Figure 23:
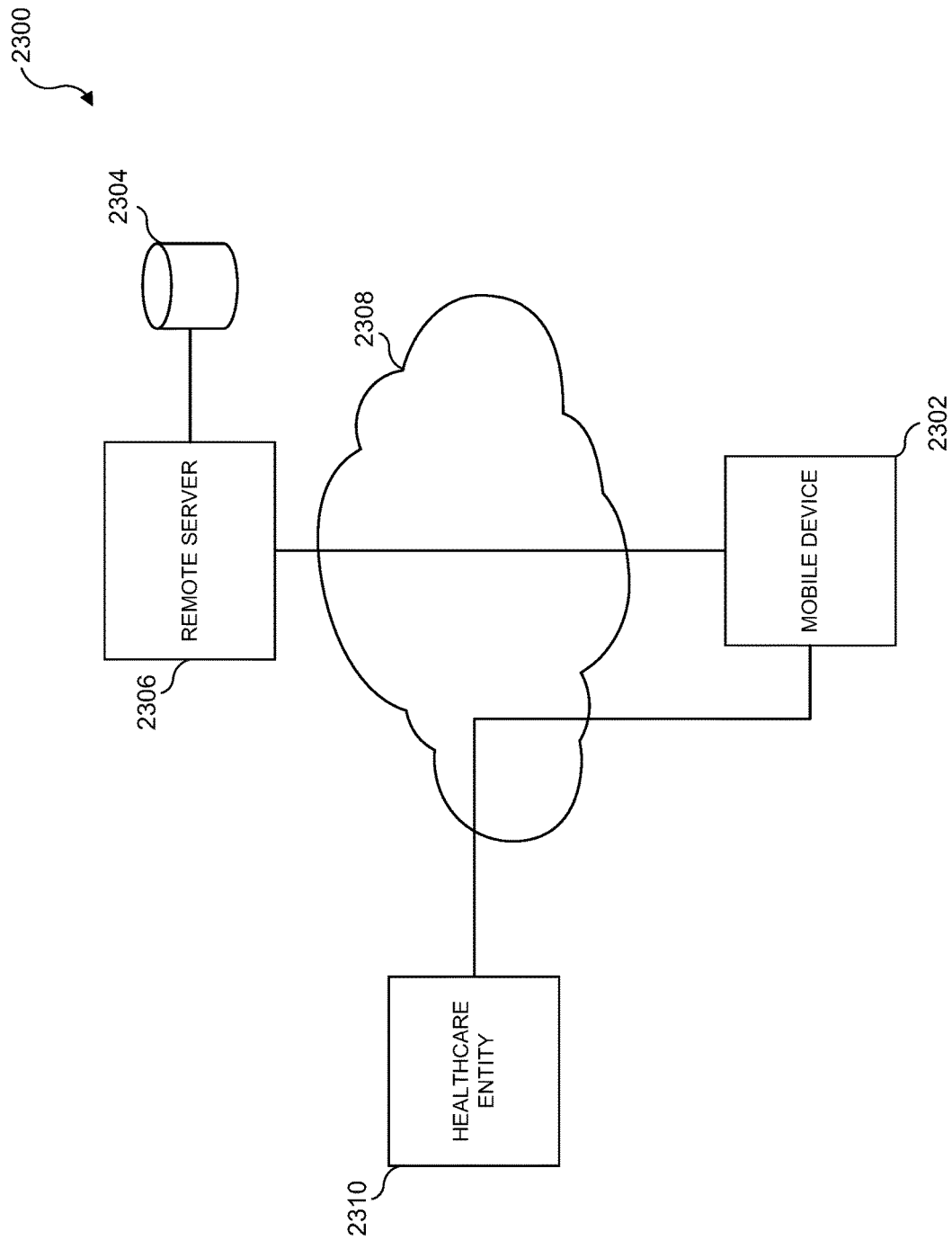
FIG. 23 illustrates one embodiment of a medical code correlation system.

Referring now to FIG. 23, there is illustrated a medical code correlation system 2300. The system 2300 includes a mobile device 2302, which is configured to run the mobile application described herein. The mobile device 2302 is connected to a database 2304 disposed on a server 2306, over a network 2308. To correlate a medical code, the mobile device first passes a diagnostic test identifier to the remote server. This identifier allows for the type of test being used by the user of the mobile device 2302 to be determined. The identifier may simply be the name of the test, may be a number associated with the test, or any other means of identifying the test being performed by the user of the mobile device 2302. This may be done when the phone capture the image of the testing device to process the results, or the user may enter the test to be performed before a test is conducted, at which time the mobile device 2302 may pass the identifier to the remote server. In other embodiments, the diagnostic test identifier may even be the medical code. For example, if the diagnostic test is a strep test, the identifier may be G0435, an HCPCS code for a rapid immunoassay test, or any other appropriate medical code.

Once the physical test results of the diagnostic test is captured, and once the results are processed by the mobile device 2302 or the server 2306, the results are also received by the server. Once the server 2306 has the diagnostic test identification and the results of the test, the server 2306 may then correlate the specific test and the results with appropriate medical codes stored within the database 2304. It will be understood that the database 2304 may be physically located with the server 2306, or the database 2304 may be a remote database, such as a centralized database that allows entities within the healthcare industry to retrieve the latest medical codes. The medical codes assigned may then be transferred from the mobile device 2302 to a healthcare entity 2310. In other embodiments, the medical codes may be transferred from the server 2306 to the healthcare entity 2310. The healthcare entity 2310 may be a physician, a hospital, a pharmacy, an insurance company, or any other entity that may provide the user with further assistance.

Figure 24:
FIG. 24 illustrates one embodiment of a strep home retail test codes table.

Referring now to FIG. 24, there is illustrated a strep home retail test codes table 2400. The table 2400 lists the various medical codes that may be associated with a home testing device that is used to test for a streptococcal infection. The table 2400 is representative of the types of codes that may be stored in the database 2304 in relation to a particular retail strep test device. The table 2400 lists a diagnosis code of J02.0, an ICD-10-CM code for streptococcal pharyngitis. The table 2400 also lists an HCPCS code of G0435, which is a code for a rapid antibody test. The table 2400 also lists an NDC code of 54569-5182-0, which is the NDC code for an amoxicillin prescription. Thus, when the server 2306 assigns the medical codes to the testing device or the test results, various codes may be produced. The example shown in table 2400 shows that the strep home retail testing device is assigned the HCPCS code of G0435 to indicate the type of test it is, a rapid antibody test. If the test results come back as positive, the server assigns the ICD-10-CM code to this event, indicating a streptococcal throat infection. In response to these positive test results, the server 2306 provides the NDC code for amoxicillin as a recommended prescription to give to the user to treat the infection.

In some embodiments, this prescription may be passed to a pharmacy so that the pharmacy may fill the prescription for the user to pick up, or to be delivered to the user. In some embodiments, the medical codes and other information may be passed to a physician for review. This physician may be the primary care physician of the user, allowing the user to set an appointment to go over the test results and get a prescription from the physician. In other embodiments, the physician may be a telemedicine physician that either the user contacts, the physician sets up a telemedicine conference, or the system described herein automatically initiates in response to the test results. The physician may alter the recommended prescription provided by the system, may conduct additional testing, or otherwise handle the situation as he or she sees fit as a physician. In addition, in some embodiments, the medical codes may be passed to an insurance company to seek reimbursement for the testing device, the prescription, the visit with the physician, or any other costs that arise from this testing event. To accomplish such, the user may have provided his or her insurance information when signing up to use the mobile application in conjunction with the various testing devices provided.

Figure 25:
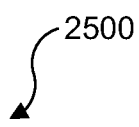
FIG. 25 illustrates one embodiment of a combined pregnancy and Zika home retail test codes table.

Referring now to FIG. 25, there is illustrated a combined pregnancy and Zika home retail test codes table 2500. The table 2500 lists the various medical codes that may be associated with a home testing device that is used to test for both pregnancy and a Zika infection. The table 2500 is representative of the types of codes that may be stored in the database 2304 in relation to a particular retail pregnancy/Zika testing device. The table 2500 has a pregnancy codes column and a Zika codes column. The pregnancy codes column lists a diagnosis code of Z33.1, an ICD-10-CM code for a pregnant state. The pregnancy codes column also lists an HCPCS code of G8802, which is a code for a pregnancy test. The pregnancy codes column also lists an NDC code of 42192-321-30, which is the NDC code for prenatal vitamins. The Zika codes column lists a diagnosis code of A92.5, an ICD-10-CM code for the Zika virus. The Zika codes column also lists an HCPCS code of G0435, which is a code for a rapid antibody test. The Zika codes column also lists an NDC code of 50580-501-30, which is the NDC code for prescription strength Tylenol. In some embodiments, instead of separate codes for each type of test performed, there may be a single code assigned to, for example, a combined pregnancy and Zika test, or even a single code for a pregnant with Zika infection state.

It will be understood that the codes listed in FIGS. 24-25 are examples of how the system may assign codes to a testing event. The use of the specific codes and the types of codes (ICD-10-CM, HCPCS, and NDC codes) are merely used for illustrative purposes; any type of codes may be used and the specific codes listed in FIGS. 24-25 may be other, more appropriate, codes for the particular testing device, diagnosis, etc. Different types of codes include, but are not limited to, ICD-9-CM, ICPC-2, NANDA, Read code, SNOMED, CCI, CDT, NIC, NMDS, NOC, CCAM, OPCS-4, or other codes.

Figure 26:
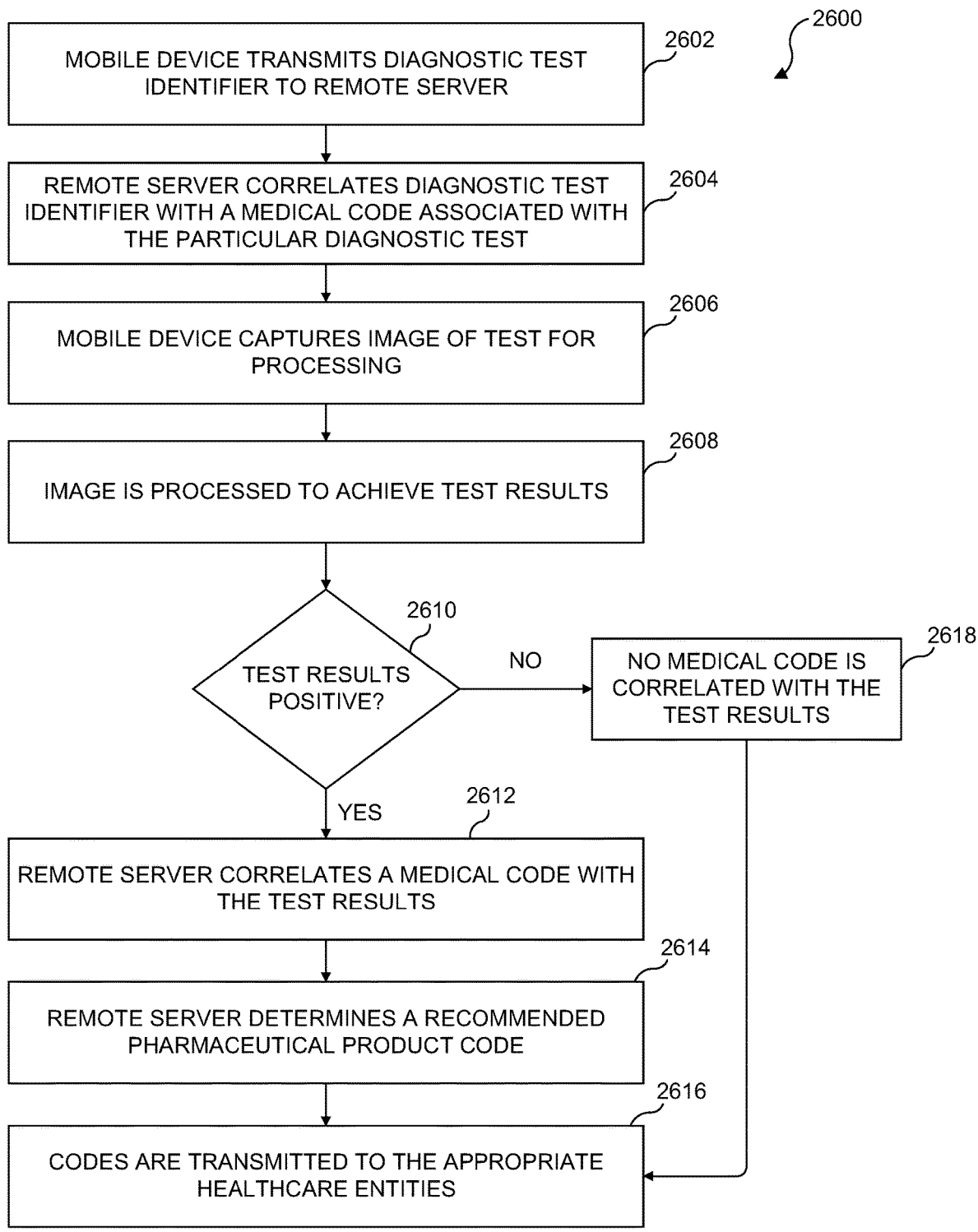
FIG. 26 illustrates flowchart of one embodiment of a medical code correlation process.

Referring now to FIG. 26, there is illustrated a flowchart of one embodiment of a medical code correlation process 2600. The process begins at step 2602 where the mobile device 2302 running the application described herein transmits a diagnostic test identifier to the remote server 2306. At step 2604, the remote server 2306 correlates the diagnostic test identifier with a medical code associated with the particular diagnostic test. This identifier allows for the type of test being used by the user of the mobile device 2302 to be determined. The identifier may simply be the name of the test, may be a number associated with the test, or any other means of identifying the test being performed by the user of the mobile device 2302. This may be done when the phone capture the image of the testing device to process the results, or the user may enter the test to be performed before a test is conducted, at which time the mobile device 2302 may pass the identifier to the remote server. In other embodiments, the diagnostic test identifier may even be the medical code. For example, if the diagnostic test is a strep test, the identifier may be G0435, an HCPCS code for a rapid immunoassay test, or any other appropriate medical code.

The process then flows to step 2606, where the mobile device 2302, as part of the overall operation of the system and mobile application described herein, capture an image of the testing device for processing. At step 2608, the image is processed to achieve the test results. Such processing may be performed on the mobile device 2302, on the remote server 2306, another server, or any other device that may be interfaced with the system disclosed herein. The process then flows to decision block 2610, where it is determined whether the test results indicated a positive result (positive infection, pregnancy, or other outcomes). If the test result is positive, the process flows to step 2612, where the remote server 2306 correlates a medical code with the test results. As described herein, components other than the remote server 2306 may correlate the test results with a medical code, such as a centralized server and database used in the healthcare industry to retrieve medical codes. The process then flows to step 2614 to assign a recommended pharmaceutical product based on the test results. This may be an NDC code for a product, and there may even be provided a prescription for such. At step 2616, the codes are transmitted to the appropriate healthcare entities, such as a physician, a pharmacy, or other entities.

If at decision block 2610 it is determined that the test results are negative, the process instead flows to step 2618, where no medical code is correlated with the test results. This provides that no diagnosis code if provided, since the test results indicate that the user is not positive for the condition being tested. However, a medical code for the test itself, determined at step 2604, may still be applicable in this scenario, because the user still used the diagnostic test, and therefore may still be reimbursed for the cost of the test, if the user's insurance company chooses to do so. The user's physician may also want to see the test results, even if they are negative, and the code for the test and the negative results may still be transmitted to the physician. Therefore, after step 2618, the process then flows to step 2616 to transmit the codes (in this case, the code for the testing device product) to the appropriate healthcare entities. The test results themselves may also be transmitted.

Figure 27:
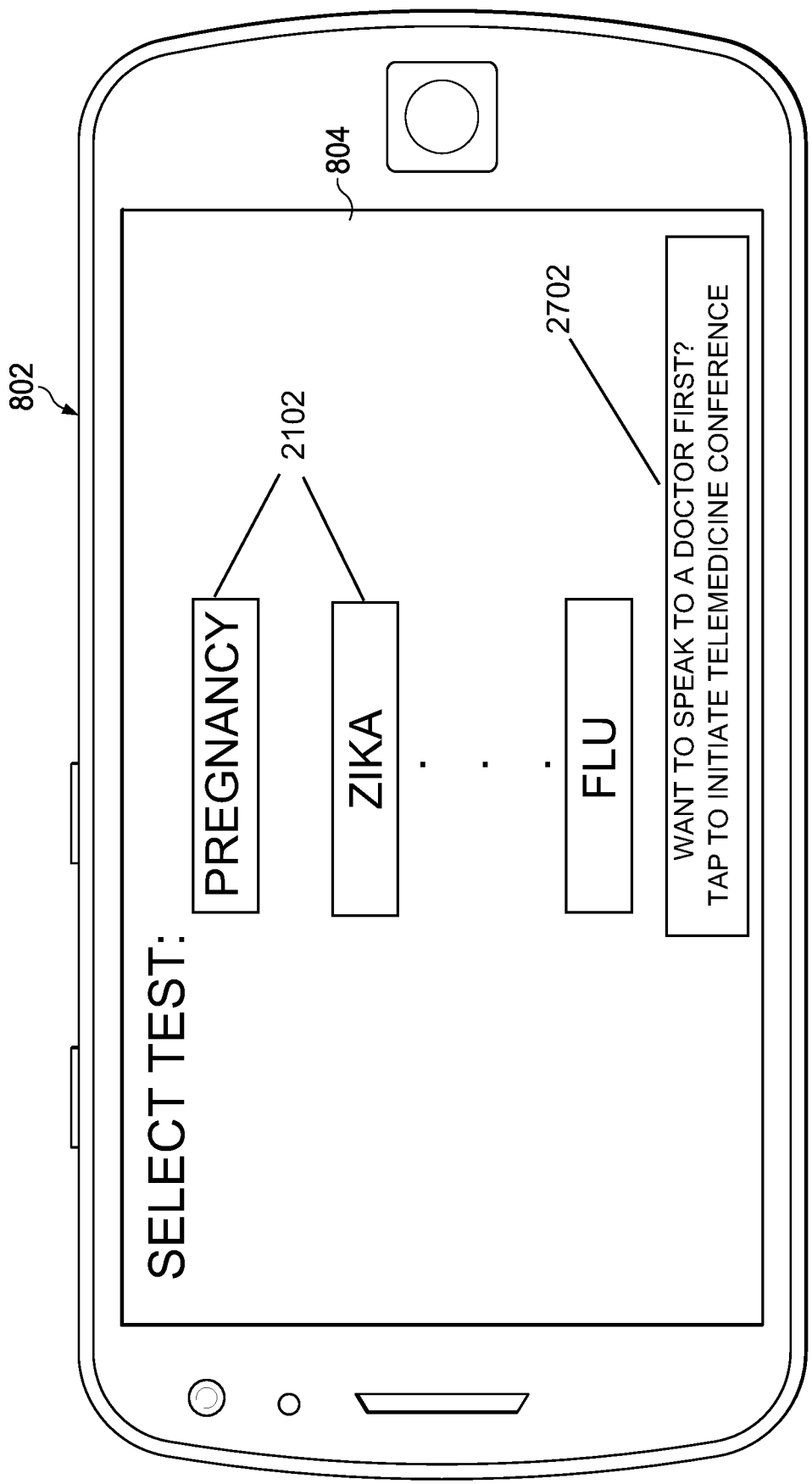
FIG. 27 illustrates one embodiment of a telemedicine initiation option within a mobile application.

Referring now to FIG. 27, there is illustrated one embodiment of a telemedicine initiation option within a mobile application. The mobile application and system described herein is predominantly meant to first test a patient for a medical condition, and then recommend an action, such as seeing a physician. However, the system allows for telemedicine conferences to be initiated, and therefore functionality may exist wherein a user can request a telemedicine conference with a physician at any time while using the mobile application, in order to receive a diagnosis or simply to ask questions. Thus, FIG. 27 again shows the plurality of test functions 2102 displayed on the screen 804. In addition to these options, an additional option is presented to the user. This option is a telemedicine conference button 2702 that allows a user to initiate a telemedicine conference with a qualified telemedicine provider. This button 2702 is shown on the screen where the user selects the type of test to be performed, but the button 2702 may be presented within the user interface on any screen of the mobile application.

Figure 28:
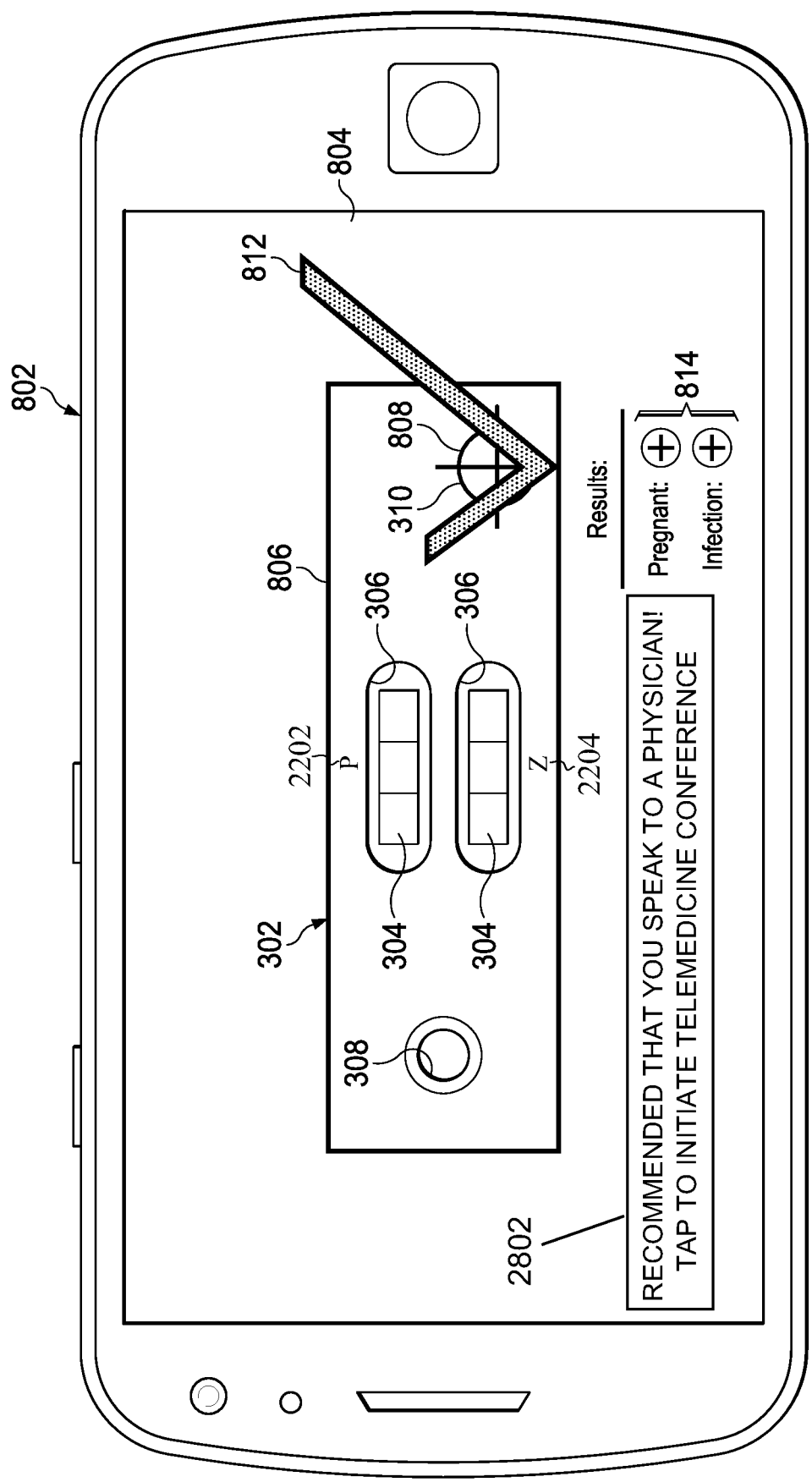
FIG. 28 illustrates another embodiment of a telemedicine initiation option within a mobile application.

Referring now to FIG. 28, there is illustrated another embodiment of a telemedicine initiation option within a mobile application. There is shown on the screen 804 the test results as previously shown on FIG. 22, which indicate positive pregnancy and Zika test results. In such a situation where the test results indicate a possible serious medical condition, a button 2802 may appear to the user on the screen 804. The button 2802 may have a warning message within, urging the user to seek a consultation with a physician to talk about the user's options in light of the positive test results, and inviting the user to tap the button 2802 to initiate a telemedicine conference with a physician. Tapping the button 2802 will initiate such a telemedicine conference. The physician that is connected with for the conference may be an on-call physician that has agreed to make his or her services available through the system described herein, the telemedicine conference may use an existed telemedicine conference platform and physician base, the user's primary care physician may be a user of the system and mobile application, allowing for them to be used as the default telemedicine contact for the user, or other methods of making physicians available for a conference with the users of the mobile application may be provided.

Figure 29:
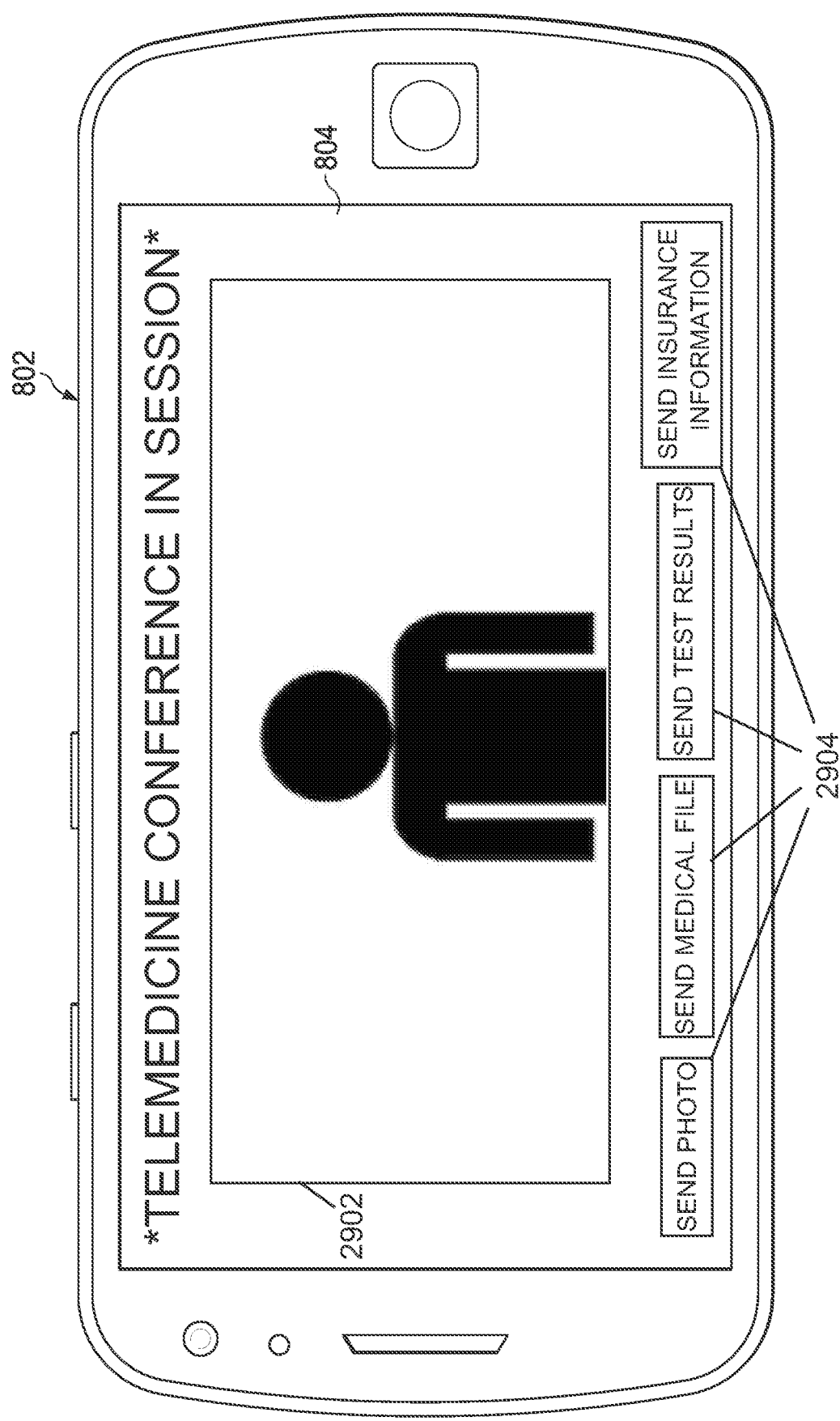
FIG. 29 illustrates one embodiment of a telemedicine conference session on a mobile device.

Referring now to FIG. 29, there is illustrated one embodiment of a telemedicine conference session on a mobile device. During a telemedicine conference that has been initiated as described herein, the user is presented with a video conference window 2902 on the screen 804. The video conference window 2902 allows for user to see the physician that is providing the telemedicine services to the user. It will be understood that the physician may have a similar video window on the device being used by the physician that allows the physician to see the user. This allows the physician to make some visual observations of the user's condition. In addition to the video conference window 2902, the user is presented with a plurality of actions 2904 on the screen 804. The plurality of action 2904 may be buttons that allow the user to provide the physician with further information. For example, one button may allow for the user to send a photograph to the physician, such as a photograph of the user's symptoms, or of the user's test results presented on the testing device. One button may also provide an option for sending the user's medical file to the physician, so that the physician can review the user's medical history or other important information. This medical file may include all the information accumulated from all tests performed by the user under the system described herein, and may also include all other medical history information. The user may have provided a copy of his or her medical history, or such may have been retrieved from a central electronic medical records system.

Other actions that may be provided in the plurality of actions 2904 may be a button to send test results to the physician. This would allow the user to send the test results of the latest test the user took before initiating the telemedicine conference, or it may allow for the user to choose the test. The plurality of actions 2904 may also include a button for sending the user's insurance information to the physician. The user may have provided this information within the mobile application and had it stored to the server, or this information may have been pulled via a confidential link from a centralized database for the user based on the user's identification information. This option allows the user to give the physician insurance information so that the physician can use the user's insurance for reimbursement of the telemedicine services, and may even set up reimbursement to the user for certain services or products, such as the testing device used for the test.

Figure 30:
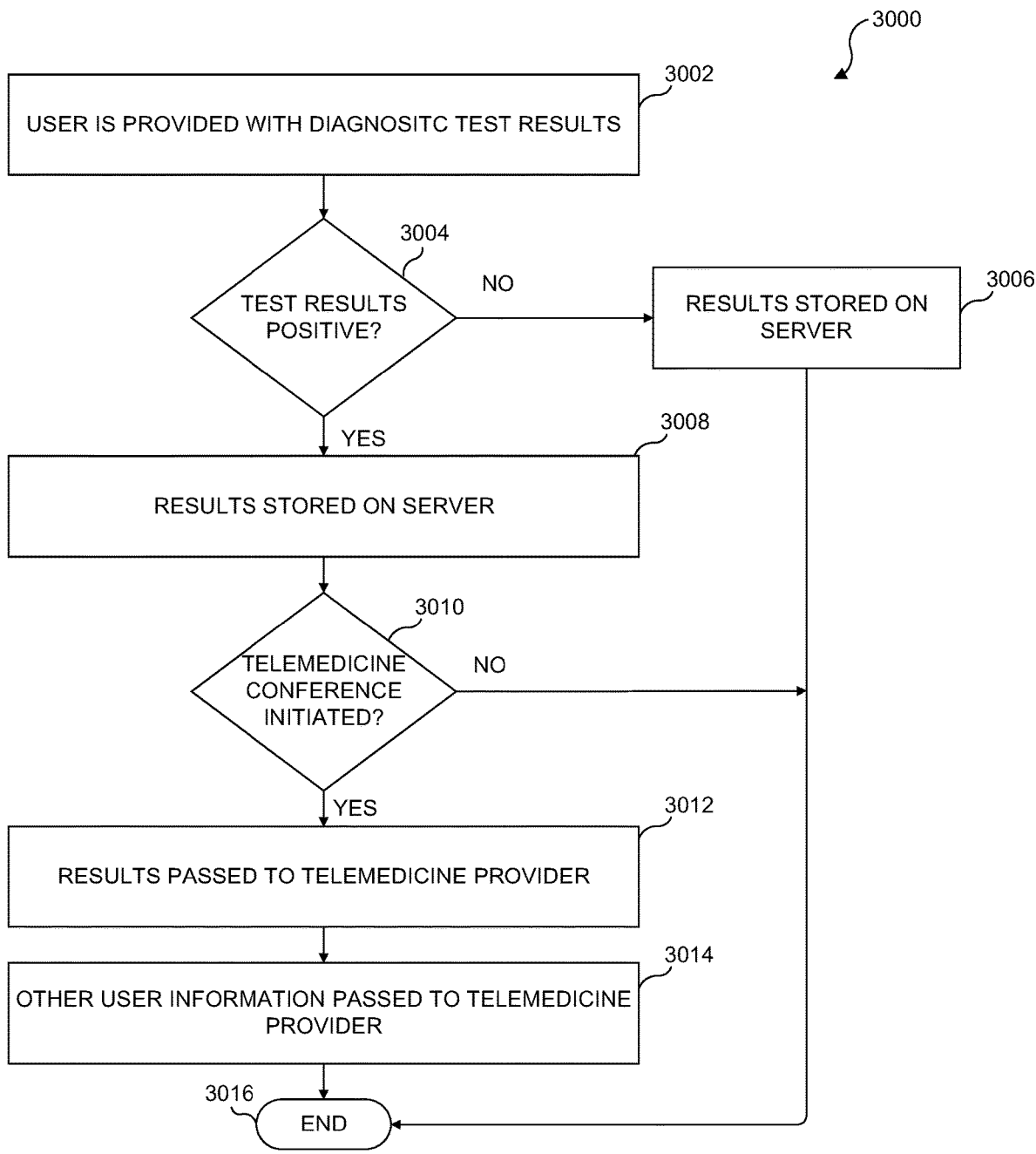
FIG. 30 illustrates a flowchart of one embodiment of a medical file handoff process.

Referring now to FIG. 30, there is illustrated a flowchart of one embodiment of a medical file handoff process 3000. The process 3000 starts at step 3002 where a user is provided with diagnostic test results at the conclusion of a performance of a test. At decision block 3004, it is determined whether the test results provide a positive result. If not, at step 3006 the results are stored on the server of the system described herein and the process ends at end block 3016. If the results are positive, the process flows to step 3008 where the results are stored on the server. At step 3010, it is determined whether a telemedicine conference has been initiated. This initiation may have been selected as described with respect to FIGS. 27 and 28, may have been initiated automatically due to the results provided, or may have been initiated in some other way. If the telemedicine conference was not initiated, the process ends at end block 3016. If the telemedicine conference was initiated, the process flows to step 3012 where the test results are passed to the telemedicine provider participating in the telemedicine conference. The process then flows to step 3014, where other user information is passed to the telemedicine provider. The process then ends at end block 3016.

The passing of the results to the telemedicine provider and other information at steps 3012 and 3014 may be performed by the user's mobile device, wherein the mobile device sends the files to the telemedicine provider. The passing may also be done by the server of the system described herein, wherein the results and other information were previously stored to the server and the server then passes the results and other information to the telemedicine provider as a result of the server being notified of a telemedicine conference initiation. The other user information of step 3014 may be any information needed by the telemedicine provider, such as past medical records and medical history of the user, past test results, insurance information, or any other information.

Figure 31:
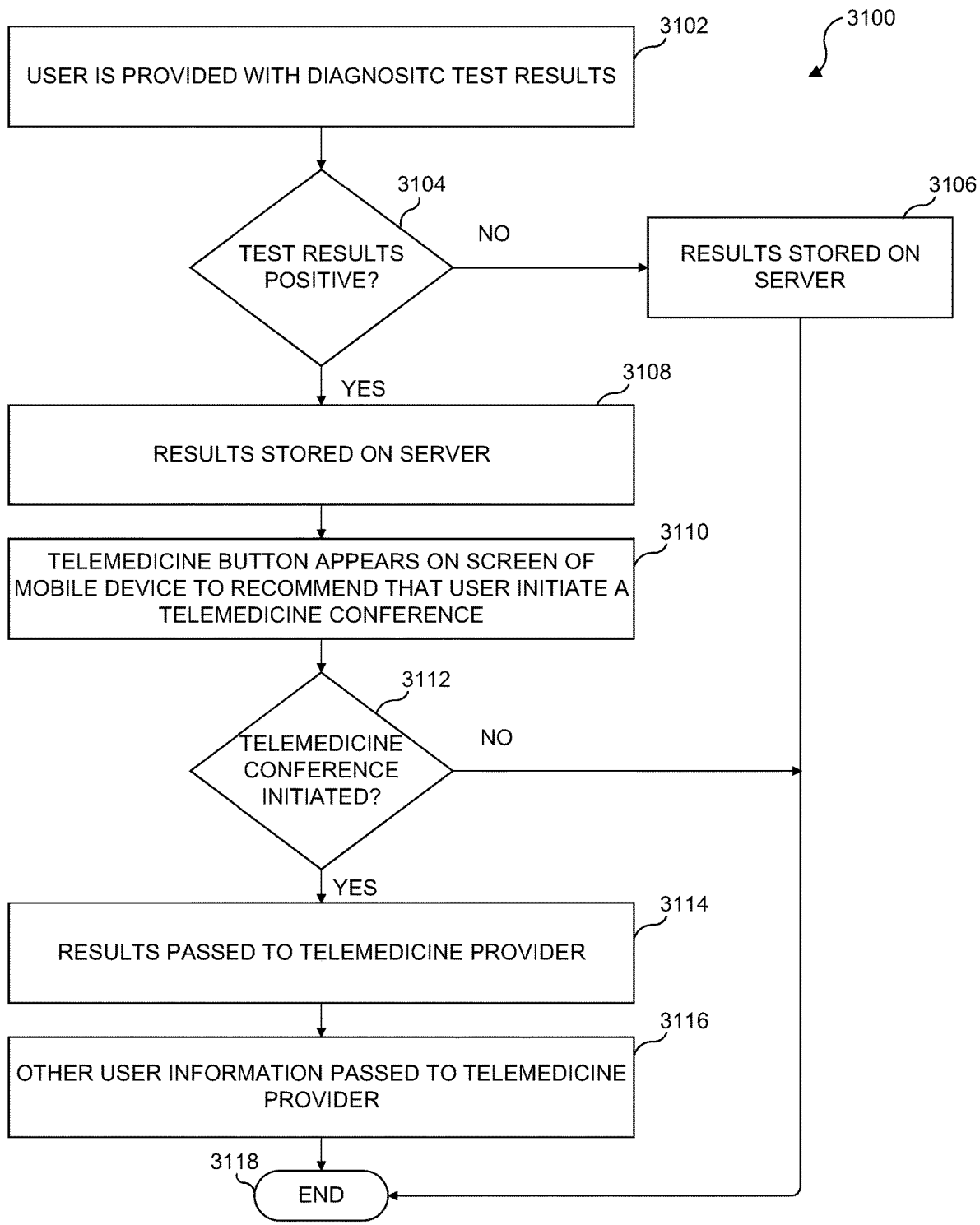
FIG. 31 illustrates a flowchart of one embodiment of a telemedicine conference initiation process.

Referring now to FIG. 31, there is illustrated a flowchart of one embodiment of a telemedicine conference initiation process 3100. The process 3100 starts at step 3102 where a user is provided with diagnostic test results at the conclusion of a performance of a test. At decision block 3104, it is determined whether the test results provide a positive result. If not, at step 3106 the results are stored on the server of the system described herein and the process ends at end block 3118. If the results are positive, the process flows to step 3108 where the results are stored on the server. At step 3110 a telemedicine button is presented to the user on the screen of the mobile device, similar to that shown in FIG. 28. This button recommends to the user that the user initiate a telemedicine conference, since the test results indicate a positive reaction. At step 3112, it is determined whether a telemedicine conference has been initiated. This initiation may have been selected as described with respect to FIGS. 27 and 28, may have been initiated automatically due to the results provided, or may have been initiated in some other way. If the telemedicine conference was not initiated, the process ends at end block 3118. If the telemedicine conference was initiated, the process flows to step 3114 where the test results are passed to the telemedicine provider participating in the telemedicine conference. The process then flows to step 3116, where other user information is passed to the telemedicine provider. The process then ends at end block 3118.

The passing of the results to the telemedicine provider and other information at steps 3114 and 3116 may be performed by the user's mobile device, wherein the mobile device sends the files to the telemedicine provider. The passing may also be done by the server of the system described herein, wherein the results and other information was previously stored to the server and the server then passes the results and other information to the telemedicine provider as a result of the server being notified of a telemedicine conference initiation. The other user information of step 3116 may be any information needed by the telemedicine provider, such as past medical records and history of the user, past test results, insurance information, or any other information.

Figure 32A:
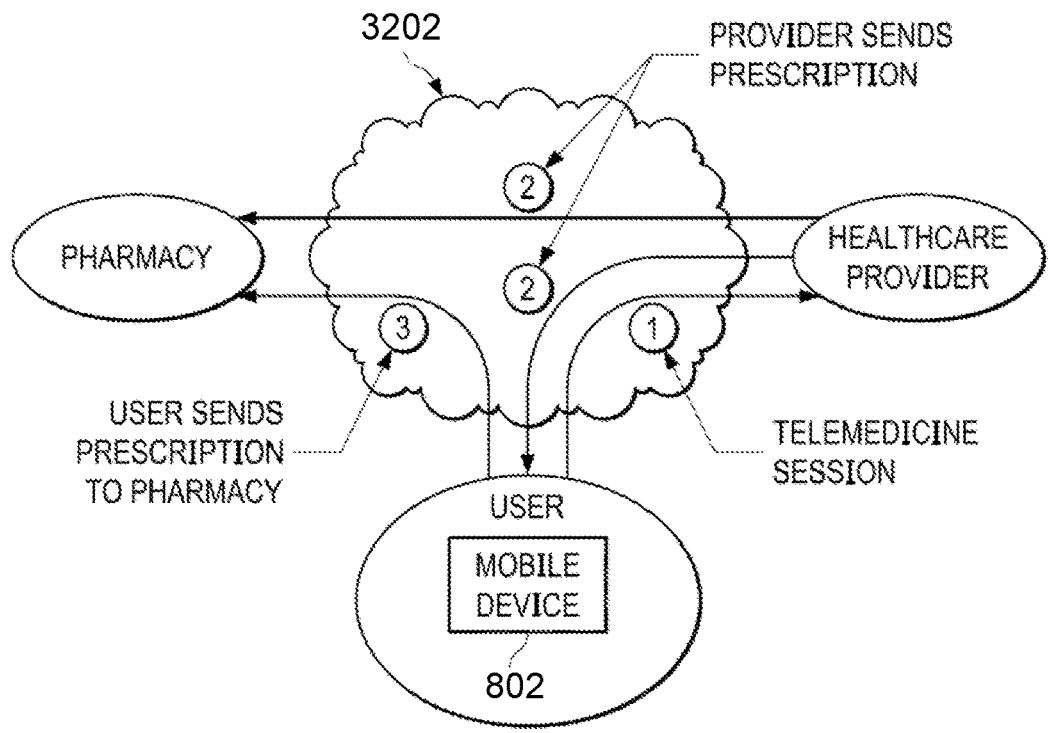
FIGS. 32A-B illustrated systems for transmitting prescriptions to a pharmacy using telemedicine.

Turning now to FIG. 32A, there is illustrated an embodiment of a system in which a prescription is transmitted to a pharmacy using a self-diagnostic test and telemedicine. In these embodiments, rather than the patient needing to physically travel to a pharmacy to drop off a prescription to be filled, the user uses a mobile application to electronically transmit the prescription information to the pharmacy. These embodiments improve upon embodiments which use self-diagnostic tests and telemedicine and take advantage of the fact that the user is already engaged in a telemedicine session with the user's healthcare provider through a network 3202 such as the internet. In these embodiments, the user engages in a telemedicine session with a healthcare provider as described hereinabove, via Path (1). When the user and the healthcare provider complete the telemedicine session, the healthcare provider can prescribe necessary medicine to the mobile application user. However, since the user is not physically present with the healthcare provider, the user does not pick up a physical prescription slip. Instead, the healthcare provider transmits via Path (2) the prescription in electronic form either to the user's mobile application, or to the pharmacy of the user's choice. If the healthcare provider transmits the "electronic prescription" to the user's mobile application, then the user can then store the electronic prescription on his mobile device 802 in the mobile application until he is ready to get the prescription filled. The user then uses the mobile application to send the electronic prescription to the pharmacy via Path (3). The pharmacy then fills the prescription as normal.

Figure 32B:
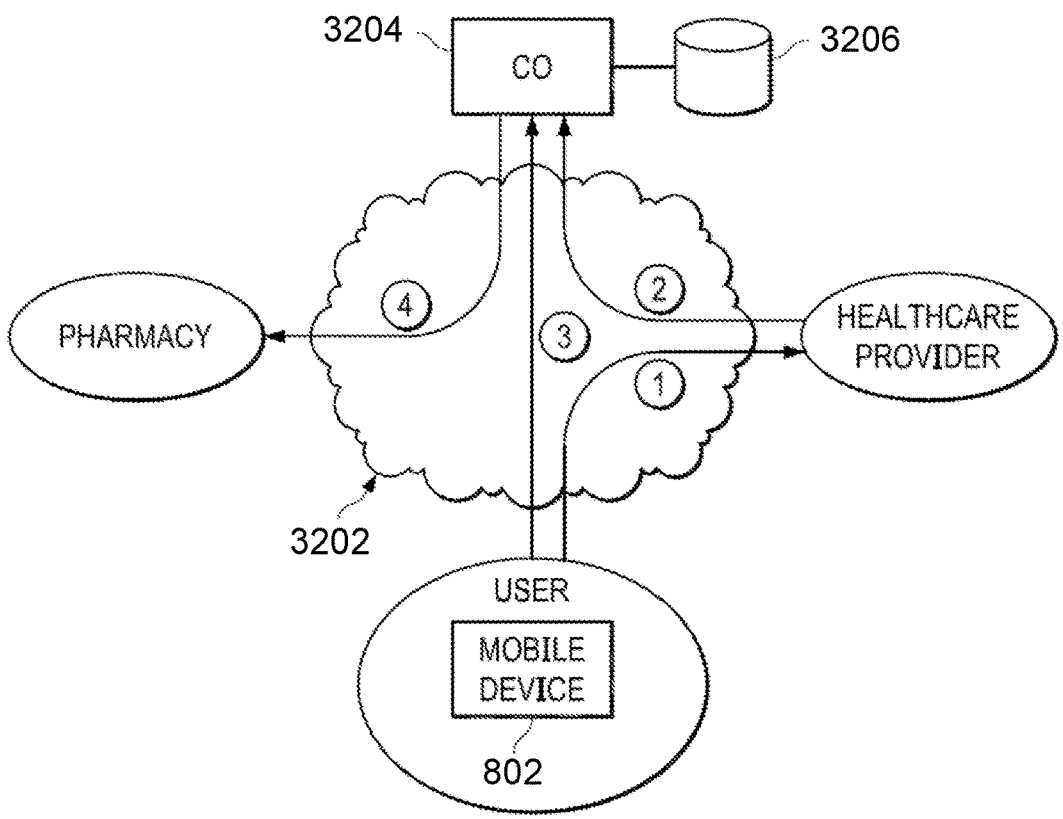

Turning now to FIG. 32B, there is illustrated another embodiment of a system in which a prescription is transmitted to a pharmacy using a self-diagnostic test and telemedicine. These embodiments are similar to those described hereinabove with respect to FIG. 32A. The system includes a user with a mobile device 802 running a mobile application, a healthcare provider, a pharmacy, and a remote server or central office with a records database. In these embodiments, the user participates in a telemedicine session with a healthcare provider via Path (1) as described hereinabove with respect to FIGS. 29-31. Next, if the healthcare provider decides that a prescription is needed, the healthcare provider creates a prescription record and transmits the record through a network 3202 such as the internet to a central office 3204 or remote server via Path (2). The central office 3204 then stores the record in a records database 3206. When the user is ready to have their prescription filled, they use the mobile application on the mobile device 802 to contact the central office 3204 via Path (3). The central office 3204 then retrieves the prescription record from the database 3206 and sends the prescription record to the pharmacy via Path (4) to have the prescription filled. With this method, the healthcare provider does not have to worry about which pharmacy to send the prescription to, and the fact that the prescription record does not have to be stored on the mobile device 802 means that the user could potentially access the prescription record from another mobile device or any other compatible device with network access.

Figure 33:
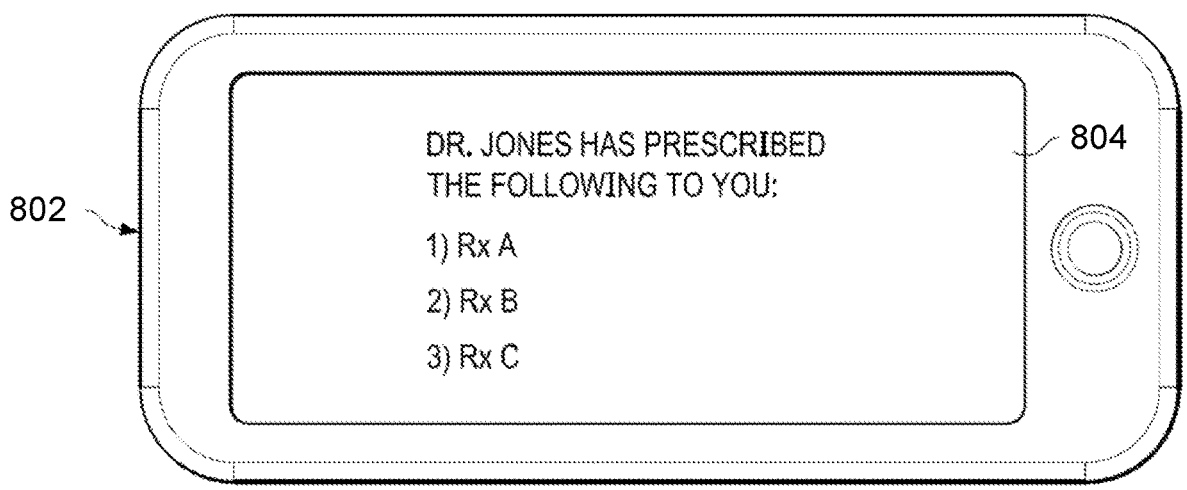
FIG. 33 illustrates an embodiment which uses a mobile application to inform the user which prescriptions have been prescribed

Turning now to FIG. 33, there is illustrated an embodiment in which the mobile application running on the mobile device 802 displays what prescriptions have been prescribed by the healthcare provider to the user. In these embodiments, the mobile application informs the user what prescriptions have been issued or "written" for him by the healthcare provider without the need of physical records. The user receives a notification from the mobile application when the healthcare provider has given the prescription. For example, if the healthcare provider issues ("writes") the prescription during the telemedicine session, the screen illustrated in FIG. 33 will be presented at that time. Or, if the healthcare provider writes the prescription after the telemedicine session has ended, the user will be notified by the mobile application at that time.

Figure 34:
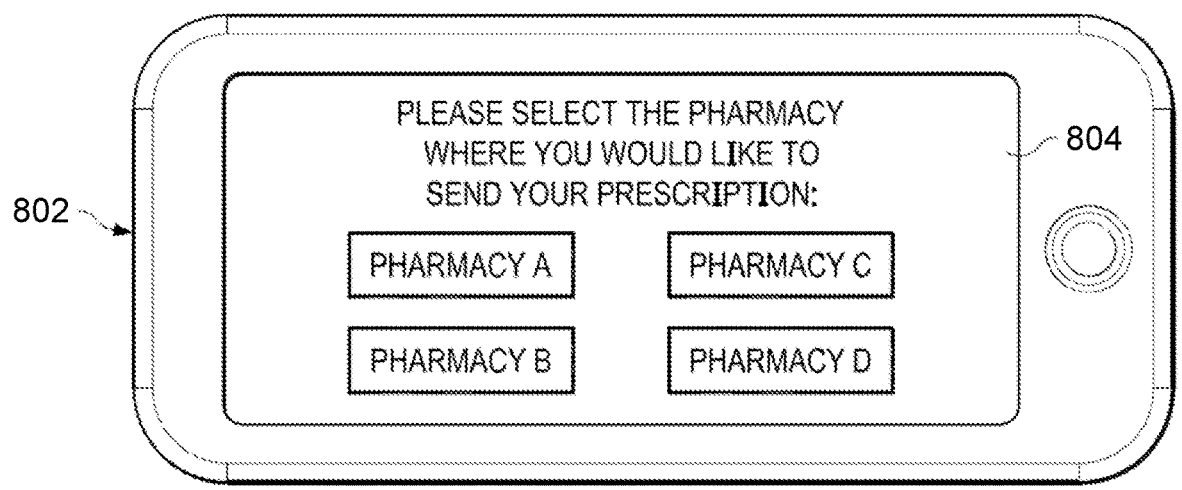
FIG. 34 illustrates an embodiment which uses a mobile application to let a user decide which pharmacy will fill a prescription.

Turning now to FIG. 34, there is illustrated a mobile device 802 from an embodiment in which the user can select which pharmacy to send the prescription to. In these embodiments, a menu displays a choice of pharmacies. These choices can be based on geographic location, on which pharmacies accept the user's insurance, or any other factor which might influence a user's choice of pharmacy. Once the user selects which pharmacy will fill the prescription, the prescription record is transmitted to that pharmacy so that it can be filled. In some embodiments, a preferred pharmacy is selected ahead of time, so that the user does not have to select a pharmacy each time the user receives a prescription from a healthcare provider. In these embodiments, the user is presented instead with a confirmation screen which user will use to send the prescription to the previously-chosen pharmacy to be filled.

Figure 35:
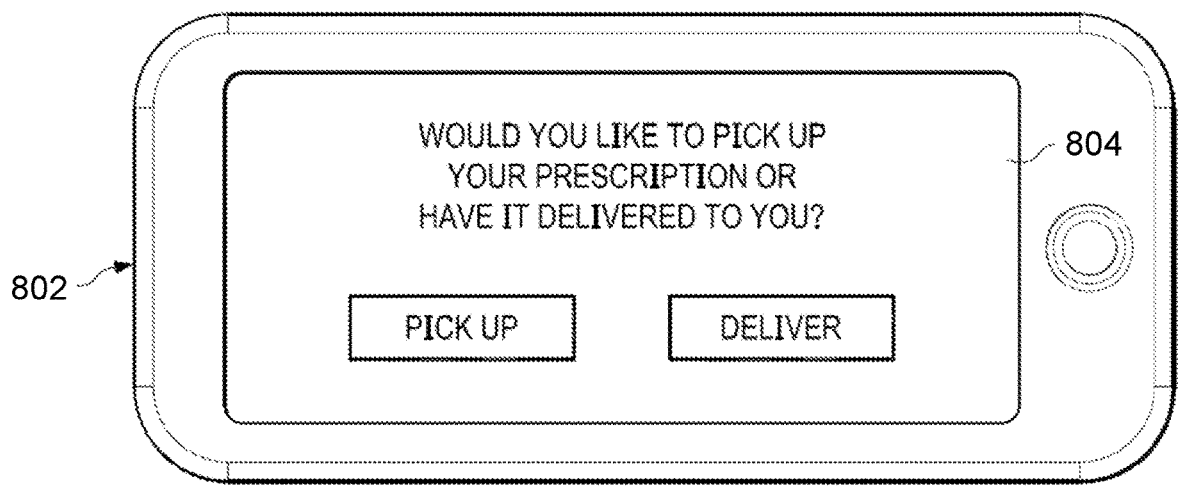
FIG. 35 illustrates an embodiment in which the user can select on a mobile application whether to pick up a prescription or have the prescription delivered.

Turning now to FIG. 35, there is illustrated a mobile device 802 from an embodiment of the system which allows for the prescription to either be picked up or delivered. In some embodiments of the system, the user is offered the convenience of having the prescription delivered to the user's home or place of work. In these embodiments, when a prescription is sent to a pharmacy to be filled, the user is presented with a menu in the mobile application which gives him the option of choosing to pick up the prescription himself, or of having the prescription delivered. If the user selects to have the prescription delivered, the user will then be presented with a screen in the mobile application where he or she enters the delivery address. Some embodiments will allow for addresses to be pre-entered into the mobile application and saved. This will speed up future prescription fillings, as the user will not have to enter the delivery address every time he selects to have a prescription delivered. In some embodiments, if the user selects to pick up the prescription, the user will be given an estimated ready time for the prescription or a notification through the mobile application when the prescription is ready to be picked up.

Figure 36:
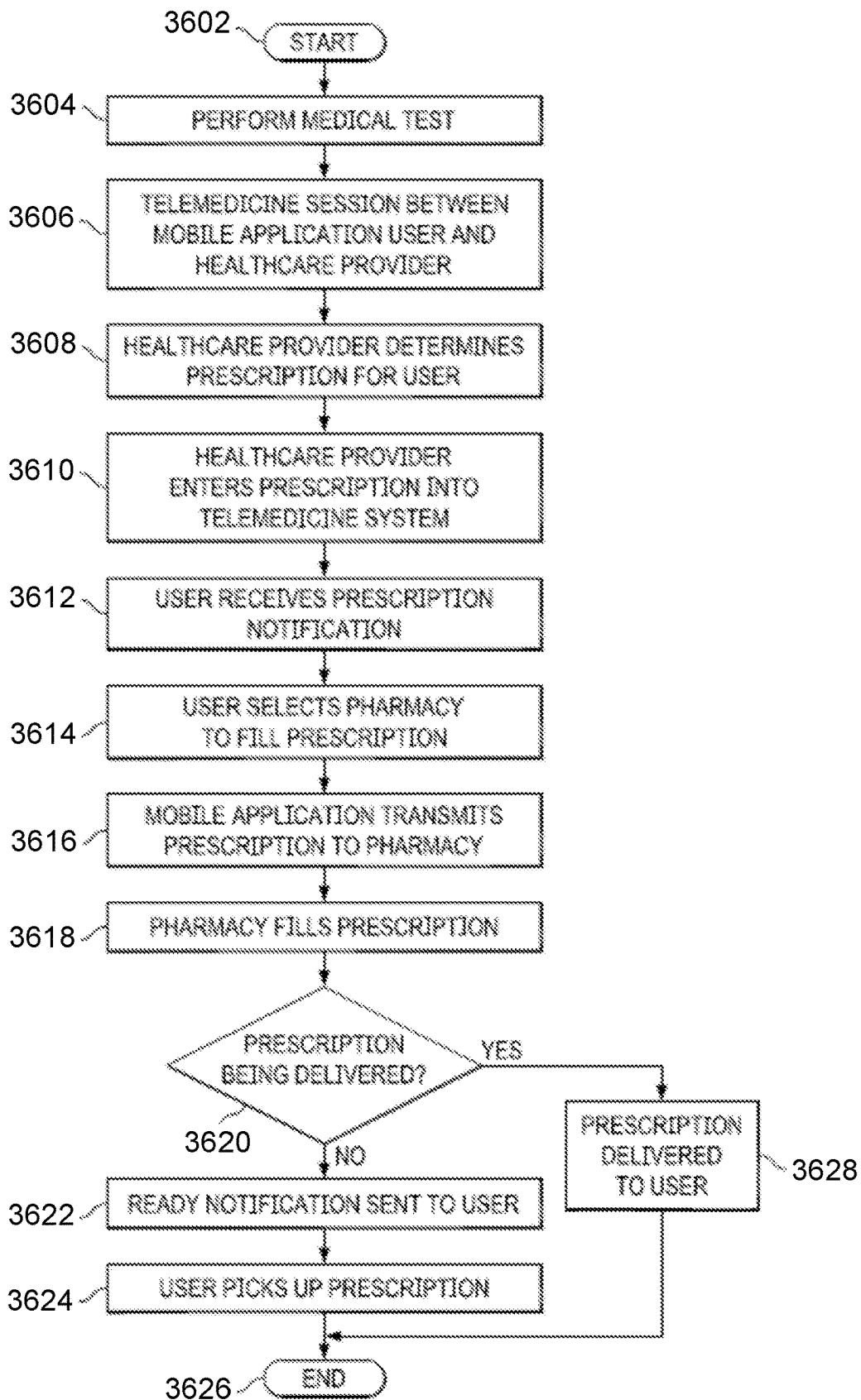
FIG. 36 illustrates a flowchart depicting a process for filling a prescription using a self-diagnostic test and a telemedicine session.

Turning now to FIG. 36, there is illustrated a flowchart of the process for using a self-diagnostic test and telemedicine to obtain a prescription. The process starts at Start block 3602 and proceeds to block 3604. At block 3604, the user performs a self-diagnostic test such as is described hereinabove with respect to FIGS. 9 and 11. Next, at block 3606, a telemedicine session is established and occurs between the user and a healthcare provider as described hereinabove with respect to FIGS. 29-31. Next, the process moves to block 3608, where the healthcare provider determines that the user needs a prescription. In some embodiments, this step takes place during the telemedicine session. Next, the process moves to block 3610, where the healthcare provider issues a prescription for the user and enters the prescription information into the telemedicine system. Next, at block 3612, the user is notified through the mobile application that they have been prescribed medication. The process then moves to block 3614, where the user selects a pharmacy to fill the prescription. As discussed hereinabove with respect to FIG. 34, this step may not take place if the user has a pharmacy pre-selected. Next, at block 3616, the mobile application causes the prescription to be sent to the pharmacy to be filled. The process then moves to block 3618, where the pharmacy fills the prescription. The block then moves to decision block 3620, where the user chooses whether the prescription will be picked up or delivered. If the user chooses to pick up the prescription, the process moves to function block 3622, where the system sends the user a notification that the prescription is ready for pick-up. The process moves to block 3624, where the user picks up the prescription and then ends at block 3626. If the user chooses to have the prescription delivered, then the process moves to block 3628, where the prescription is delivered to the user at his selected address. The process then ends at block 3626.

Figure 37:
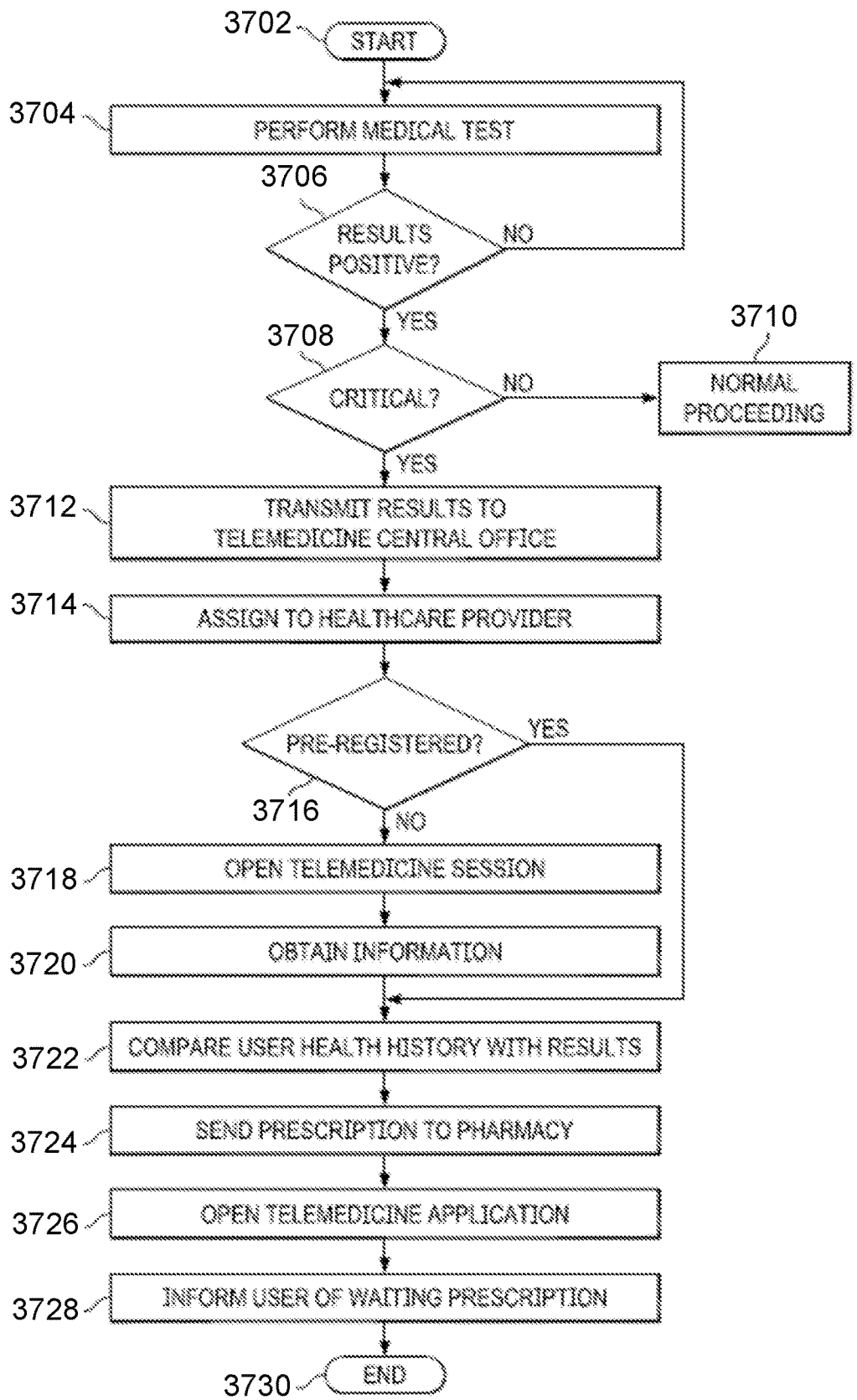
FIG. 37 illustrates an embodiment in which a telemedicine mobile application is used to automatically fill a prescription.

Turning now to FIG. 37, there is illustrated an embodiment in which a telemedicine mobile application is used to automatically fill a prescription. In some cases, when a patient is diagnosed with a particular ailment, the prescription is likely to be a predetermined medication or set of medications. In these cases, a healthcare provider can often issue a prescription for the user without having to actually see or talk to the user. Having a user's health history and the results of a diagnostic test are often enough for a healthcare provider to issue a prescription for a user. Some embodiments take advantage of these situations and improve the efficiency of the telemedicine and prescription-filling process by allowing prescriptions to be issued and filled automatically, without significant interaction between the user and the healthcare provider. The process starts at Start block 3702 and proceeds to function block 3704, where the user performs a self-diagnostic test. The process then moves to decision block 3706. If the self-diagnostic test returns negative results, the process loops back to block 3704 until the user performs another self-diagnostic test sometime in the future. If the test results are positive, the process moves to decision block 3708. If the positive result from the test does not indicate a "critical" or urgent situation, the process movies to block 3710, where a normal telemedicine proceeding occurs, as described hereinabove with respect to FIGS. 27-31. If, however, the results indicate an urgent or critical situation which can be resolved without significant user interaction with a healthcare provider, the process moves to function block 3712. At block 3712, the mobile application transmits the self-diagnostic test results to a central office or remote server for the telemedicine system. The process moves to block 3714, where a healthcare provider is assigned to the user's test results, which are transmitted by the central office to the healthcare provider. The process then moves to decision block 3716, where, if the user has pre-registered, that is, has supplied their health history and pharmacy preferences to the telemedicine system, the process moves to block 3722, where the healthcare provider compares the user's health history with the self-diagnostic test results to determine if a prescription should (can) be issued to the user.

If, at block 3716, the user has not pre-registered, the process moves to block 3718, where a session of the telemedicine application is opened on the user's mobile device. This session is simply for the user to provide the information necessary for the healthcare provider to issue the proper prescription. The process moves to block 3720, where the user provides their health history and their pharmacy preferences to the telemedicine system through the mobile application. Next, the process move to block 3722, where the healthcare provider compares the user's health history and the test results to determine if a prescription should be issued. The process then moves to block 3724, where the healthcare provider issues a prescription and sends it to the pharmacy. The process moves next to block 3726, where the telemedicine application opens on the user's mobile device. At block 3728, the telemedicine mobile application informs the user that the prescription has been filled by the pharmacy and is ready for pick-up or delivery. The process then ends at End block 3730.

Figures 38, 39:
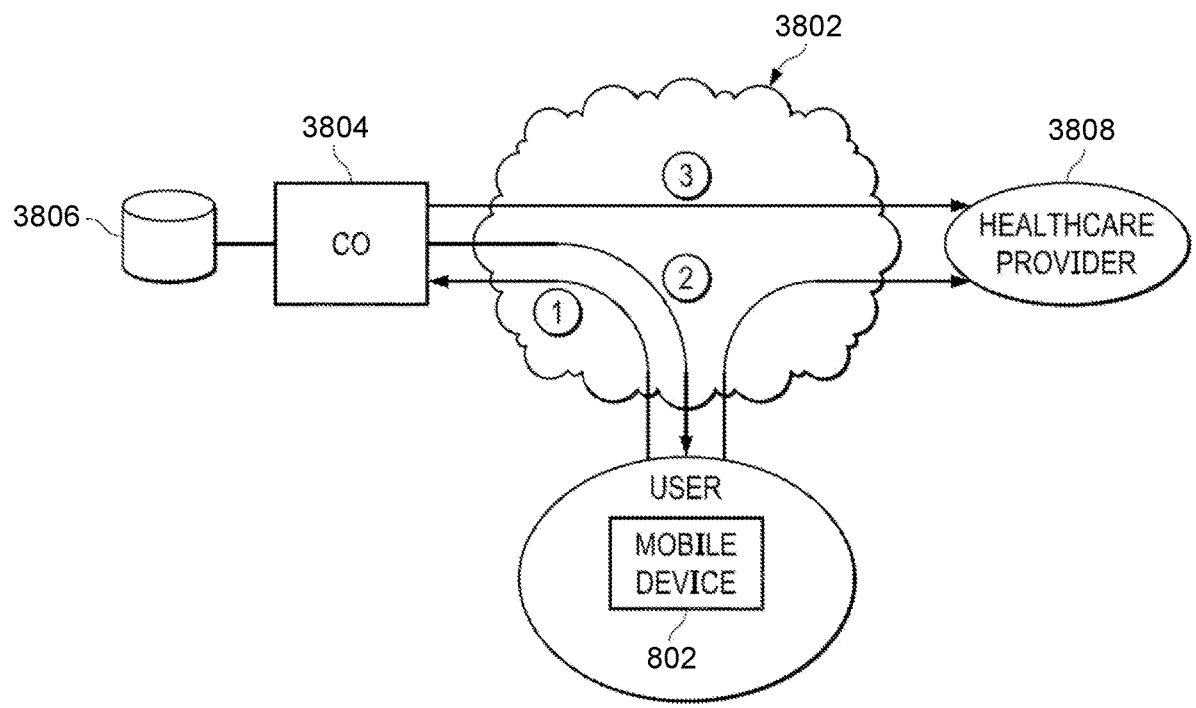
FIG. 38 illustrates an embodiment of a system which utilizes a remote diagnostic test to initiate a medical escalation and intervention.
FIG. 39 illustrates an example of a table which would be found in the database of a central office and which contains criteria for when to initiate a medical intervention based on the results of a remote diagnostic test.

Turning now to FIG. 38, there is illustrated an embodiment of a system which utilizes a remote diagnostic test to initiate a medical escalation and intervention. In some situations, the result of a medical diagnostic test will indicate that immediate or urgent medical attention is needed for the patient. In some embodiments, medical attention will be summoned automatically in these situations. In these embodiments, the user performs a self-diagnostic medical test and uses a mobile application running on a mobile device 802 to capture an image of the test product, as described hereinabove with respect to FIGS. 9-11. The mobile application then transmits, via Path ①, the test information through a network 3802 to a remote server or central office 3804. The central office 3804 accesses a database 3806 for the necessary information to generate a result for the self-diagnostic test. Again, the process up to this point is analogous to the embodiments described hereinabove with respect to FIGS. 9-11. However, in embodiments such as illustrated in FIG. 38, the central office 3804 also retrieves from the database 3806 criteria for determining whether or not a medical escalation or intervention is warranted on the basis of the test results. The central office 3804 generates a test result and checks the criteria to determine if medical escalation is needed. If no medical escalation is needed, the central office 3804 simply returns, via Path ②, the test results to the mobile device 802 through the network 3802. If, however, the central office 3804 determines that some type of medical escalation is warranted, then the central office transmits, though the network 3802 via Path ③, the test and test result information, along with information about the user (such as any relevant personal, demographic and/or contact information collected from the user) to a healthcare provider 3808. Alternatively, instead of the healthcare provider 3808 being contacted by the central office 3804, in some embodiments, the fact that a medical escalation is needed is transmitted along with the test results from the central office 3804 through the network 3802 via Path ② to the mobile device 802 running the mobile application. The mobile device 802 then transmits the test and test result information to a healthcare provider 3808 through the network 3802 via Path ④.

The manner of the medical escalation or intervention varies depending on the embodiment, and may vary depending on the type of test and/or the test results. In some embodiments, the escalation takes the form of notifying emergency medical personnel, rather than a healthcare provider 3808, of an urgent medical situation. In these embodiments, the central office may call 911 or in some other way notify emergency services These embodiments would be useful, for example, if a blood test shows that the self-diagnostic test user has near fatal levels blood sugar or that the user is having a heart attack or stroke. In other embodiments, the medical escalation takes the form of the mobile application on the mobile device automatically initiating a telemedicine session with a healthcare provider 3808. These embodiments are useful, for example, in urgent, but not quite emergency, situations. For example, elevated blood sugar or high blood pressure might not be immanently deadly to a patient, but should still be addressed and brought to the attention of a healthcare provider 3808 provider quickly. In other embodiments which are most useful for urgent—but not quite emergency—situations, the central office 3804 notifies the healthcare provider 3808 of the test results, and leaves it up to the healthcare provider to determine the best next course of action to take with respect to the patient.

Turning now to FIG. 39, there is illustrated an example of a table which would be found in the database of a central office 3804 and which contains criteria for when to initiate a medical intervention based on the results of a remote diagnostic test. The table 3902 includes several columns of information. In the example embodiment depicted in FIG. 39, the diagnostic test is a quantitative one which produces a numerical rating as part of the test result, similar to the embodiments described hereinabove with respect to FIGS. 9-13. An example of such a test could be a blood glucose test, wherein a certain risk is generally associated with a range of glucose levels. In this example, a low test result "rating" indicates a low health risk for the condition being tested, while a higher "rating" indicates a higher risk. In the some embodiments which use a table such as table 3902, different types of medical intervention are used for different test results. The first column 3904 of table 3902 specifies a range of test result "ratings," while the rest of the columns 3904, 3906, and 3908 specify information correlating to that rating range. Column 3906 specifies the health risk associated with a particular test result rating from column 3904, and column 3908 specifies what type of medical intervention will be initiated for a test result within a given range. For example, if a user conducts the example self-diagnostic test, and the central office 3804 generates a test result rating of 57 (which indicates a dangerous health risk), then the central office will not only return the test result to the user, it will also initiate an urgent medical intervention, such as initiating a telemedicine session between the user and a healthcare provider. If the central office 3804 generates a test result rating of 93 (which would indicate a deadly health risk), then the central office will initiate an emergency health intervention, such as notifying emergency medical services of the user's condition. On the other hand, if the test result rating is in the "NORMAL" or "ELEVATED" range, then no medical intervention will be initiated, and the central office 3804 will simply return the test results to the user and the mobile device 802. Naturally, other embodiments will have different styles of tables in the central office 3804 database. Some embodiments which have qualitative rather than quantitative tests (for example, testing simply "positive" or "negative" for a disease) will not have various multiple different types of medical intervention.

Figure 40:
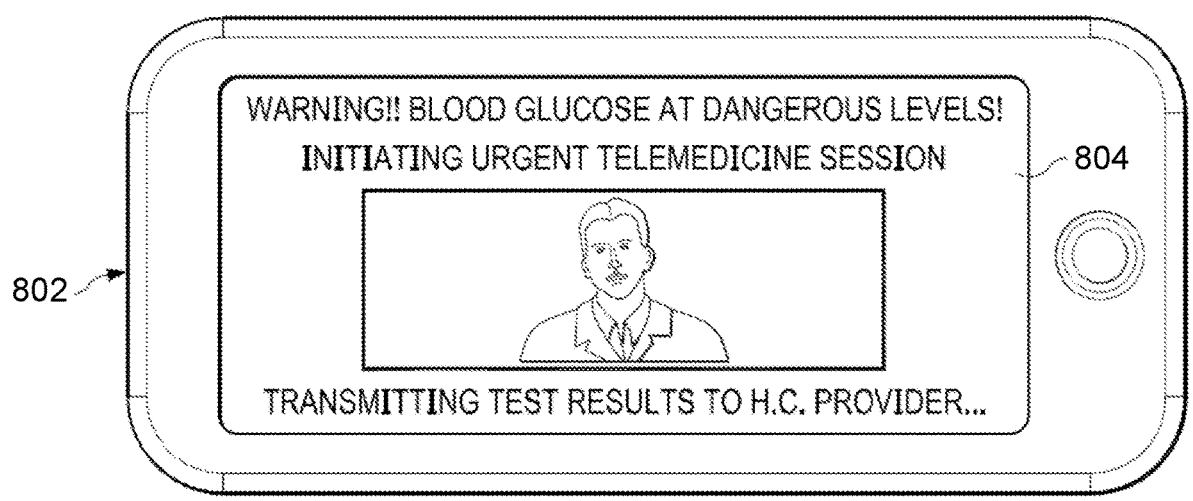
FIG. 40 illustrates a mobile device from an embodiment in which a medical intervention in the form of a telemedicine session is initiated on a mobile device in response to a diagnostic test.

Turning now to FIG. 40, there is illustrated a mobile device 802 from an embodiment in which a medical intervention in the form of a telemedicine session is initiated on a mobile device in response to a diagnostic test. In the example illustrated in FIG. 40, the mobile application running on the mobile device 802 displays that a self-diagnostic test performed by a user has returned a result showing the user has dangerous levels of blood glucose. As described hereinabove with respect to FIGS. 38-39, different embodiments will have different types of medical intervention. In the example of FIG. 40, the mobile application automatically initiates a telemedicine session in response to the high blood glucose test result. The mobile application informs the user that the test results indicated a dangerous glucose level, initiates the telemedicine session, and transmits the test results to the healthcare provider (some embodiments transmit the test results to the healthcare provider directly from the central office 3804).

Figure 41:
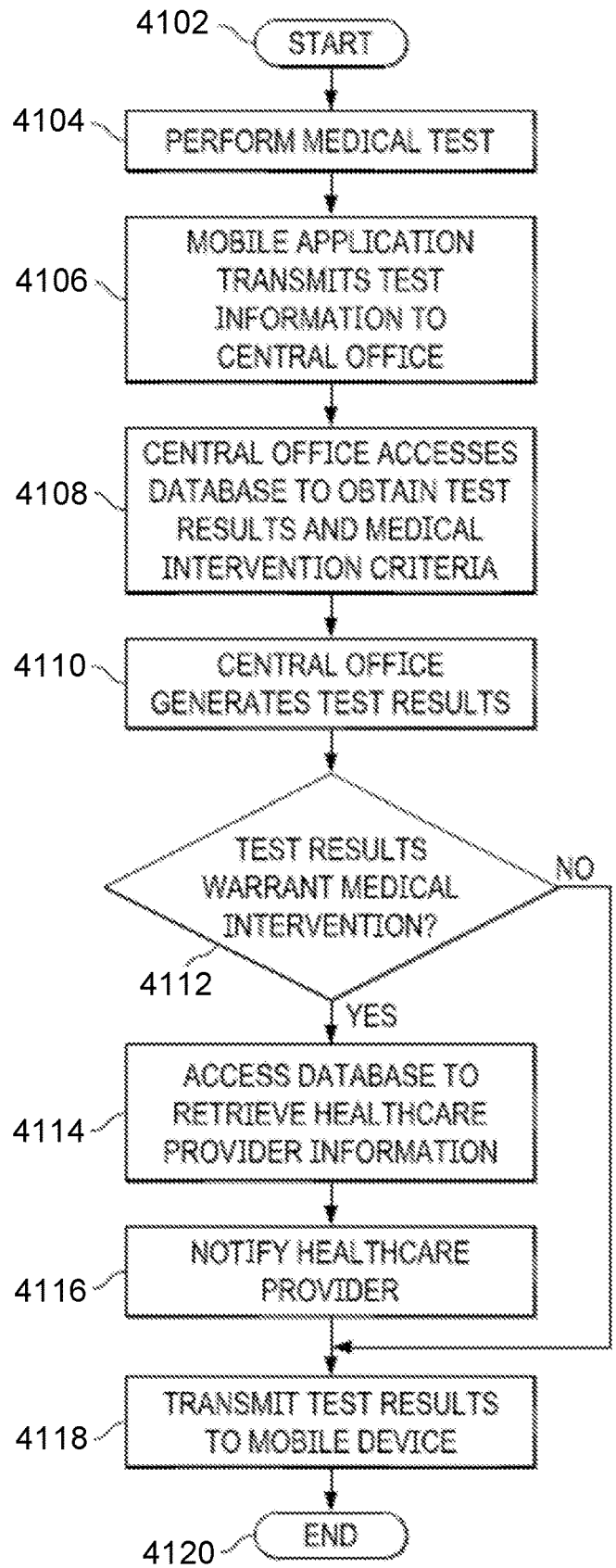
FIG. 41 illustrates a flowchart for an embodiment which initiates a medical escalation or intervention as a result of a remote diagnostic test.

Turning now to FIG. 41, there is illustrated a flowchart for an embodiment which initiates a medical escalation or intervention as a result of a remote diagnostic test. The process starts at START block 4102. Next, the process moves to function block 4104, where the user performs a self-diagnostic medical test and reads the testing equipment with a mobile device, such as is described hereinabove with respect to FIGS. 1-8. Next, at block 4106, a mobile application on the mobile device transmits the test information, including the image or images of the captured by the mobile device, to a central office over a network 3802. The process flows to block 4108, where the central office 3804 accesses a connected database 3806 to obtain information for generating a test result, as well as information detailing the criteria for initiating a medical intervention. Next, at block 4110, the central office 3804 generates test results based on the information transmitted from the mobile device 802 and the information obtained from the database 3806. At decision block 4112, the central office 3804 determines whether or not, based on test results, a medical intervention is warranted. If a medical intervention is warranted, the process flows to block 4114, where the central office accesses the database 3806 to retrieve healthcare provider information for the user. The process then proceeds to block 4116, where the central office 3804 notifies the healthcare provider 3808 of the test results. Next, the process moves to block 4118, where the central office 3804 transmits the test results to the mobile device 802 through the network 3802. The process then ends at END block 4120. If, at decision block 4112, no medical intervention is warranted, then the process instead moves to block 4118 and block 4120, as described hereinabove.

It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A system, comprising:
    a database containing criteria for initiating a medical intervention, the database including in association with at least one type of diagnostic test a plurality of diagnostic test result levels, each test result level indicating a different severity of the diagnostic test result, each test result level defining a particular medical intervention response associated with the particular diagnostic test result level;
    a server disposed on a network, the server configured to:
        receive, from a mobile device, an image of an immunoassay test strip and user information associated with the immunoassay test strip;
        determine diagnostic test results based on the image of the immunoassay test strip, wherein the server is further configured to:
            identify RGB color values for a plurality of pixels in a region of the image of the immunoassay test strip, the RGB color values consisting of Red, Blue and Green individual color values, and
            create a normalized color value from the RGB color values, wherein the normalized color value is created relative to a particular color of the RGB color values associated with the plurality of pixels in the region of the image of the immunoassay test strip, wherein the normalized color value is a single value indicative of a weight of the particular one of the individual Red, Blue and Green individual color values of the RGB color values as compared to other individual Red, Blue and Green individual color values of the RGB color values within the region of the image of the immunoassay test strip;
        determine the diagnostic test result level responsive to the normalized color value by:
            assigning a health risk rating for the created normalized color value that defines a health risk associated with the diagnostic test from a maximum risk for a high normalized color value for the particular one of the individual Red, Blue and Green individual color values maximum risk for a zero normalized color value for the particular one of the individual Red, Blue and Green individual color values,
            adjusting the created normalized value when at a value between zero and maximum based upon actual experience of medical professionals;
        store the diagnostic test result level including the normalized color value and the user information in association with the server;
        access the database to determine a medical intervention response associated with the determined diagnostic test result level; and
        perform the medical intervention response associated with the determined diagnostic test result level within the database.

2. The system of claim 1, wherein a test line of one of the plurality of immunoassay test strips includes Zika virus antigen and a test line of another one of the plurality of immunoassay test strips includes an antibody suitable for binding with hCG.

3. The system of claim 1, wherein the mobile device includes a camera, a viewing screen, and a software application stored thereon, wherein the software application provides executable instructions that, when executed, cause the mobile device to:
    initiate operation of the camera of the mobile device;
    present on the viewing screen of the mobile device an alignment graphic to be aligned with an alignment target of the immunoassay test strip;
    detect when an alignment of the alignment graphic and the alignment target has taken place;
    capture the image of the immunoassay test strip in response to the detected alignment;
    process the image to determine pixel count and line intensity of a test line of each of the plurality of immunoassay test strip;
    compare one or more results of processing the image to a control for a test line of immunoassay test strip; and
    present the diagnostic test result on the viewing screen.

4. The system of claim 3, wherein the server is further configured to:
    transmit a medical intervention warning to the mobile device responsive to the determined diagnostic test result level,
    wherein the medical intervention warning indicates a detected medical issue and includes a healthcare recommendation message to be displayed on the viewing screen of the mobile device.

5. The system of claim 3, wherein the control is a dataset from previously conducted tests stored on a database and accessed by the software application.

6. The system of claim 1, wherein the diagnostic test level include a quantitative result level.

7. The system of claim 6, wherein the quantitative result level includes a numerical rating.

8. The system of claim 1, wherein the server is further configured to:
    determine if the diagnostic test result level comprises a positive result;
    present, if the diagnostic test level comprises the positive result, a telemedicine initiation option on a screen of the mobile device;
    determine whether the telemedicine initiation option is selected;
    send the diagnostic test result level from the server to a telemedicine provider;
    send additional medical history information to the telemedicine provider; and
    initiate a telemedicine conference with the telemedicine provider.

9. The system of claim 8, wherein the server is further configured to:
   receive, over a network, a notification relating to an issued prescription; and
   communicate information relating to the issued prescription over a network to a pharmacy.

\* \* \* \* \*